(12) United States Patent
Fujita et al.

(10) Patent No.: US 7,785,533 B2
(45) Date of Patent: Aug. 31, 2010

(54) CHIP, DEVICE USING THE CHIP, AND METHOD OF USING THE SAME

(75) Inventors: Machiko Fujita, Tokyo (JP); Toru Sano, Tokyo (JP); Kazuhiro Iida, Tokyo (JP); Hisao Kawaura, Tokyo (JP); Wataru Hattori, Tokyo (JP); Masakazu Baba, Tokyo (JP); Noriyuki Iguchi, Tokyo (JP)

(73) Assignee: NEC Corporation, Tokyo (JP)

( * ) Notice: Subject to any disclaimer, the term of this patent is extended or adjusted under 35 U.S.C. 154(b) by 1149 days.

(21) Appl. No.: 10/571,585

(22) PCT Filed: Sep. 13, 2004

(86) PCT No.: PCT/JP2004/013335

§ 371 (c)(1), (2), (4) Date: Mar. 10, 2006

(87) PCT Pub. No.: WO2005/026742

PCT Pub. Date: Mar. 24, 2005

(65) Prior Publication Data

US 2007/0048179 A1  Mar. 1, 2007

(30) Foreign Application Priority Data

Sep. 12, 2003 (JP) .............................. 2003-321894

(51) Int. Cl.
*G01N 21/01* (2006.01)
(52) U.S. Cl. .......................................... 422/55; 422/57
(58) Field of Classification Search .................. 422/50, 422/55, 57, 99, 100
See application file for complete search history.

(56) References Cited

U.S. PATENT DOCUMENTS

| | | | | |
|---|---|---|---|---|
| 6,254,754 | B1 * | 7/2001 | Ross et al. | 204/600 |
| 6,729,352 | B2 * | 5/2004 | O'Connor et al. | 204/601 |
| 2006/0246573 | A1 * | 11/2006 | Kurane et al. | 435/287.2 |

FOREIGN PATENT DOCUMENTS

| | | |
|---|---|---|
| JP | 53-171708 | 6/1980 |
| JP | 61-59558 U | 4/1986 |
| JP | 3-129279 U | 12/1991 |
| JP | 9-504362 A | 4/1997 |
| JP | 9-165063 A | 6/1997 |
| JP | 11-72999 A | 3/1999 |
| JP | 2000-314719 A | 11/2000 |
| JP | 2001-264297 A | 9/2001 |
| JP | 2001-304440 A | 10/2001 |
| JP | 2002-48752 A | 2/2002 |
| JP | 2002-544523 A | 12/2002 |
| JP | 2003-4700 A | 1/2003 |
| WO | 2002/84291 A1 | 10/2002 |
| WO | WO 2005003769 A1 * | 1/2005 |

OTHER PUBLICATIONS

Daria Petersen, et al. "A New Approach for Fabricating A Zero Dead Volume Electrospray Tip for Non-Aqueous Microship CE-MS," Micro Total Analysis Sysytems 2002, vol. 2, 691-693.
M. Baba, et al. "DNA Size Separation Using Artificially Nanostructured Matrix," Applied Physics Letters, vol. 83, No. 7, Aug. 18, 2003.
Shuichi Shoji, Chemistry 1999, vol. 54, No. 10, pp. 36 to 38, Fig. 3e.

* cited by examiner

*Primary Examiner*—Glenn Caldarola
*Assistant Examiner*—Randy Boyer
(74) *Attorney, Agent, or Firm*—Sughrue Mion, PLLC

(57) ABSTRACT

A channel formed on a chip is opened without contaminating contents of the channel. Channels (107a) and (107b) provided on a substrate (103) are covered by pressing a lid (113) composed of a resin layer (102) and a plate-like lid (101) to a surface of the substrate (103). A fixing device has a retainer plate (104), which retains the plate-like lid (101) of a chip (112), a board (108) on which the substrate (103) is placed, and a screw (106). When covering the channels (107a) and (107b), the screw (106) is fastened and the lid (113) is pressed to the substrate (103) to be fixed. And, when opening an upper portion of the channels (107a) and (107b), the screw (106) is turned upward and a pressure is released, and the lid (113) is removed from the upper potion of the substrate (103).

37 Claims, 49 Drawing Sheets

701  707
     703

(a)

(b)

(a)

(b)

(a)

(b)

CHIP, DEVICE USING THE CHIP, AND METHOD OF USING THE SAME

This application claims priority from PCT Application No. PCT/JP2004/013335 filed Sep. 13, 2004 and from Japanese Application No. 2003-321894 filed Sep. 12, 2003, which applications are incorporated herein by reference.

TECHNICAL FIELD

The present invention relates to a chip, which performs a predetermined operation to a sample, a device using the chip, and a method of using the same.

BACKGROUND ART

Recently, a micro-chemical analysis (μ-TAS), in which a chemical operation such as pretreatment, reaction, separation, and detection of the sample is performed on a microchip, has been rapidly developed. The micro-chemical analysis uses only a small amount of sample, thereby allowing a high-sensitive analysis with a small environmental load.

Although the chip used in the chemical analysis including μ-TAS and in a biochemical analysis is structured so as to perform a predetermined operation to the sample in a channel formed on a substrate and in a channel such as a reaction reservoir, the sample is easily leaked from and dried in the channel, therefore, loss of the sample and deterioration of analytical sensitivity are easily occurred.

In the Patent Document 1, it is disclosed the chip, in which a minute tube for capillary electrophoresis is formed by joining a seal member made of a plastic film on a surface of a plastic plate-like member on which a groove is formed. In this manner, when the chip is structured such that the channel thereof is covered except a portion of an opening and may not be opened, it is considered to be effective with regard to above-described drying and leakage.

However, when the channel provided on the chip is covered and may not be opened, it becomes difficult to directly operate a liquid and components in the channel. Therefore, choices of operation has tended to be limited. And, an operation for transferring the liquid and the components in the channel to other region on the chip has been required.

For example, in order to realize a mass spectrometry of the components included in the sample, it is required to expose separated components in vacuum or in the air, and to vaporize by irradiating the same with a laser beam or the like. However, when separation has been performed by using a covered chip for separating, it has been difficult to directly vaporize the separated components because of an impeditive covering. Therefore, when performing the mass spectrometry of the material existing in the channel of the chip, it has been required to take the material to be measured out of the chip by using a driving mechanism such as a pump (Non-Patent Document 1).

Also, if the channel provided on the chip was covered, it has been difficult to replace the sample in the channel with another sample, and to directly operate the components of the sample from outside.

In the Patent Document 2, the electrophoresis chip, in which the reservoir filled with the migration buffer is sealed with the detachable seal, is suggested. The chip of the Patent Document 2 is aimed to speed up the operation by omitting the time-consuming process, in which the reservoir and the channel for migration are filled with the migration buffer without a space therein when operating. That is to say, the chip, in which the migration buffer is filled in the reservoir and the channel for migration in advance, and the reservoir is further sealed by the seal, is provided. In this chip, a portion thereof not being bonded is provided on a film such that the portion may be manually stripped from the substrate. And, the film covering the reservoir when using the chip is stripped from the portion being not bonded to expose the reservoir, and the migration buffer filling the reservoir is directly removed by using a pipette to replace the same with the sample liquid which is desired to be migrated, thereby allowing the filling of the sample.

[Patent Document 1]
  Japanese Laid-Open patent publication NO. 2003-4700

[Patent Document 2]
  Japanese Laid-Open patent publication NO. 2000-314719

[Non-Patent Document 1]
  Daria Peterson, and four others, "A New Approach for Fabricating a Zero Dead Volume Electrospray Tip for Non-Aqueous Microchip CE-MS", Micro Total Analysis Systems 2002, 2002, Vol. 2, pp. 691-693

[Non-Patent Document 2]
  M. Baba, and five others, "DNA size separation using artificially nanostructured matrix", Applied Physics Letters, 2003, Vol. 83, p. 1468

DISCLOSURE OF THE INVENTION

However, the conventional chip has been required to be modified in the following points. First, it has been difficult to open the channel provided on the chip. Therefore, when the sample in the channel is served to other operation, it was required a driving mechanism to transfer the sample in the channel to a predetermined position in and out of the chip. Therefore, a device structure including the chip was complicated and a production cost thereof may have been high. And, a time required to finish an entire process to the sample has been long.

And in the case of the chip as disclosed in the Patent Document 2, since this chip is structured so as to open the reservoir by stripping the film off, the sample in the reservoir may be mixed and contaminated when opening the reservoir, in a case in which the reservoirs are close to each other. Therefore, it has been difficult to integrate the reservoirs.

That is to say, when stripping off the film, a minute clearance is necessarily generated between the film being stripped and the substrate. By a capillary effect caused by the clearance, the sample in the channel leaks along an interface between the film and the substrate. Further, when stripping off the film solidly bonded by heat-sealing or by using the adhesive, an oscillation is generated. A solution in the channel is dispersed by the oscillation, the sample in the adjacent channels are mixed and contaminated. Therefore, in case of opening the channels of a highly integrated chip, in which a plurality of channels are close to each other, it has been difficult to apply the structure disclosed in the Patent Document 2.

The present invention has been achieved in order to solve the above-described problems. An object of the present invention is to provide a technology to open the channel without contaminating the sample in the channel formed on the chip.

According to the present invention, there is provided a chip having a groove-like channel formed on the surface of the substrate and a removable lid covering the channel, a device using the chip, and a method of using the same.

In the present invention, "chip" means the substrate and the lid, to which a function to perform a predetermined operation to an introduced sample is provided. The sample means contents of the channel if this is in the channel. The sample may be a liquid or a solution, and one or more component may be included in the sample. And, the channel may be formed in a stripe shape, for example. The chip of the present invention may be structured such that a channel groove is provided on the surface of the substrate, and the liquid may flow the channel groove, for example. The sample may transfer through the channel by means of a capillary phenomenon or the like, or by applying an external force such as an electrical field and a pressure. By transferring the sample, a predetermined operation such as separation and analysis may be performed to the sample.

The chip of the present invention has the removable lid. Therefore, before removing the lid, the lid forms the upper surface of the channel, so that the channel and an outer portion of the channel may be partitioned. Therefore, it becomes possible to perform a predetermined process to the sample while inhibiting evaporation and drying of the sample in the channel, leakage of the sample, and penetration of foreign material. And after usage, the lid may be removed to open the upper portion of the channel while stably maintaining the sample in the channel. So that, it is possible to prevent the sample in the channel from leaking out of the channel by means of the capillary phenomenon or the like, and from being contaminated by mixing, when opening the channel.

Meanwhile, in the specification of the present application, "contamination" of the channel includes, for example, the drying and the evaporation of the contents of the channel, the leakage of the sample, the penetration of the foreign material to the channel, the mixing of the components included in the samples of different channels, and the mixing of the components spatially separated in one channel by electrophoresis or the like.

And, as the contamination of the sample in the channel generated when opening the channel, there is a case in which the sample stayed in a predetermined range of one channel greatly transfers in the channel and the separated components are mixed, or a case in which the samples in the plurality of channels provided on the substrate are mixed to each other. The chip of the present invention is capable of inhibiting such contamination. According to the chip of the present invention, it is possible to open the channel without contaminating the sample, so that it becomes possible to directly operate the sample existing in an optional region in a minute space in the channel. Thereby, a speedy and certain operation becomes possible.

And the chip of the present invention includes the groove-like channel formed on the surface of the substrate and the lid covering the channel. By providing the lid covering the groove-like channel, it becomes possible to stably perform a predetermined operation to the sample in the channel. And, this prevents the sample in the channel from transferring through a clearance between the substrate and the lid by the capillary phenomenon, thereby preventing the separated components of the sample in the channel from being mixed, when removing the lid from the surface of the substrate. And, it is not required to sequentially transfer the sample in the channel from an outlet of the channel to other processing place, and it becomes possible to perform a predetermined operation to the sample existing in the predetermined region in the channel. Also a sequential processing to the sample becomes possible.

In the chip of the present invention, the lid may be formed by a plate-like member. And, the lid may be a plate-like lid. By doing so, the upper potion of the channel is surely covered and the sample is prevented from drying and leaking.

According to the present invention, there is provided a method of using the chip, in which a pressure is added in a perpendicular direction to the surface of the lid in a state in which the substrate abuts the lid. According to the method, the groove-like channel formed on the surface of the substrate may be more surely covered with the lid. And, when opening the upper portion of the channel, the lid may be easily removed from the substrate by releasing the pressure. Meanwhile, as a unit to pressure-weld the lid to the surface of the substrate, a screw, an hydraulic equipment, a water pressure equipment, or an air pressure device may be used. By doing so, it is possible to fix the substrate and the lid in an adhesion state.

In the chip of the present invention, the surface of the lid contacting with the substrate may be composed of a hydrophobic or water-repellent material. And in the chip of the present invention, either of a wall surface of the groove forming the channel and the surface of the lid, or both of the wall surface and the surface of the lid may be hydrophobic or water-repellent. By doing so, the sample in the channel is prevented from transferring to the surface of the lid. Therefore, the contamination of the sample in the channel when removing the lid may be surely inhibited.

In the chip of the present invention, the surface of the substrate on which the channel is formed may be hydrophobic or water-repellent. By doing so, the sample in the channel is prevented from transferring to the surface of the substrate. Therefore, the contamination of the sample in the channel when removing the lid may be surely inhibited.

In the chip of the present invention, at least a portion of the lid may be composed of an elastic material. By doing so, the lid may be more surely adhered to the surface of the substrate. Therefore, the channel may be more surely covered. In this structure, the elastic material may be adhered to the substrate and may be provided with viscoelasticy. By doing so, adhesion of the lid and the substrate may be further improved.

In the chip of the present invention, the substrate may include a plurality of the channels, and the substrate or the lid may be provided with an anticontamination agent. By doing so, it is possible to prevent an aqueous solvent from flowing through the clearance between the substrate and the lid from transferring from one channel by the capillary phenomenon and mixing in other channel, when detaching the lid from the substrate. Thereby, the samples in the plurality of channels may be prevented from being mixed. Therefore, the contamination of the channels is inhibited. For example, in the chip of the present invention, a groove portion to hold the anticontamination agent may be provided on the substrate or the surface of the lid.

In the chip of the present invention, the anticontamination agent may be oil. By doing so, an aqueous sample may be prevented from being mixed in other channel from the channel through the clearance between the substrate and the lid.

In the chip of the present invention, the lid may have a sucker portion which adsorbs to the surface of the substrate. By adsorbing the lid having the sucker portion to the surface of the substrate, the channel may be more surely covered. And, the lid may be easily removed at a desired timing.

In the chip of the present invention, a hydrophobic or water-repellent adhesive may be provided on the surface of the lid contacting with the substrate. By doing so, the channel may be more surely covered.

The chip of the present invention may have a strip portion, which opens a predetermined position of the channel. By doing so, the contamination of the sample in the channel may be more surely inhibited. Therefore, it becomes possible to highly integrate and form the channels in the chip. In the present invention, the strip portion may be formed in a tape shape. By doing so, the channel may be opened more easily. And, the strip portion may include a region, which is not joined to the substrate.

And, the strip portion may be a region, in which a plurality of cuts in the sheet are made an outer circumference thereof. And in the structure, the sheet may be formed by an oriented macromolecule film, and the cuts may be provided along an oriented direction of the oriented macromolecule. By doing so, the strip portion may be stripped from the substrate more easily.

In the chip of the present invention, the strip portion may be structured so as to include the film for removing joined to the surface of the lid and to open the opening portion by stripping the film for removing. By doing so, the predetermined position of the channel may be opened easily. In the present invention, the cuts may be provided on the lid along a longitudinal direction of the outer circumference of the film for removing. By doing so, the strip portion may be stripped from the substrate more easily.

In the chip of the present invention, the strip portion may be provided in the lid in the vicinity of the channel, and the strip portion may be composed of a material having a larger coefficient of heat shrinkage than that of the substrate. By doing so, it is possible to open the channel by heating the strip portion to fracture the lid. And the position of the channel to be opened may be selected by heating the predetermined position of the strip portion.

And according to the present invention, there is provided a method of using the chip, in which the channel is opened by irradiating the strip portion with a laser light. According to the present invention, a predetermined position of the surface of the substrate is selectively heated by irradiating the same with the laser light. Therefore, it becomes possible to remove the lid provided on the upper portion of the channel by surely heating the strip portion.

In the chip of the present invention, the substrate or the lid may be formed by a silicone resin. By doing so, the substrate and the lid may be more surely adhered. Therefore, the sample in the channel may be more surely prevented from drying and leaking. And, the sample in the channel may be prevented from leaking on the substrate or on the surface of the lid, when removing the lid. Therefore, the contamination of the sample in the lid may be more surely inhibited.

In the chip of the present invention, the lid is a seal including the silicone resin, and an operating temperature range of the chip, in which a deterioration of adhesion of the silicone resin is within 20% of a maximum value of adhesion in the temperature range not lower than −20° C. and not higher than 30° C., includes a temperature range not lower than −20° C. and not higher than 30° C. By doing so, the substrate and the lid may be more surely adhered to each other in the aforementioned temperature range, and the lid may be removed more easily under the aforementioned temperature range.

In the chip of the present invention, the substrate or the lid may be formed by an acrylic resin. By doing so, the substrate and the lid may be more surely adhered to each other. Therefore, the sample in the channel may be more surely prevented from drying and leaking. And, the sample in the channel may be prevented from leaking on the substrate or the surface of the lid when removing the lid. Therefore, the contamination of the sample in the channel may be more surely inhibited.

In the chip of the present invention, the lid is a seal including the acrylic resin, and an operating temperature range or the chip, in which a deterioration of adhesion of the acrylic resin is within 20% of a maximum value of adhesion in the temperature range not lower than −20° C. and not higher than 30° C., includes a temperature range not lower than −20° C. and not higher than 30° C. By doing so, the substrate and the lid may be more surely adhered to each other in the aforementioned temperature range, and the lid may be removed more easily under the aforementioned temperature range.

In the chip of the present invention, a gas-introducing groove may be formed on the surface of the substrate contacting with the lid or the surface of the lid contacting with the substrate. And the chip of the present invention may be structured so as to have the gas-introducing groove, at least a portion of which is exposed to the outside air, on the surface of the substrate. By doing so, it becomes possible to introduce gas into the gas-introducing groove to allow the gas to circulate on an interface between the substrate and the lid. Therefore, the lid may be easily detached from the surface of the substrate by the pressure of the gas, and the contamination of the sample in the channel at this time may be inhibited. And, when adhering the lid to the substrate, this serves as a hole to release air, thereby preventing an air bubble from remaining between the lid and the substrate.

The chip of the present invention may provide a convex structure on a portion, having at least the lid, in the channel of the substrate. By doing so, the channel may be prevented from being crushed by a deflection of the lid. And by doing so, the sample may be held in the channel when removing the lid or in an experimental procedure that follows.

The chip of the present invention may be structured such that one or more of the convex structure is formed at intervals of not larger than 80 µm in a width direction of the channel, and one or more of the convex structure may be formed at intervals of not larger than 80 µm in a longitudinal direction of the channel, and an upper surface of the convex structure may contact with the lid. Thereby, it becomes possible to surely prevent the channel from being crushed by the deflection of the lid.

In the chip of the present invention, the convex structures may especially be formed such that distance between centers thereof is not larger than 20 µm. Thereby, it becomes possible to more surely prevent the channel from being crushed by the deflection of the lid. And, it becomes possible to increase a contact area, consequently friction resistance between the sample in the channel and the convex structures. Therefore, it becomes possible to hold the sample in the channel when removing the lid or in the experimental procedure that follows.

The chip of the present invention may be a chip in which the convex structure is such that a sum in an entire circumference of an projected area thereof to a surface perpendicular to the upper surface of the channel is not less than a half of a surface area in which the lid contacts with the sample in the channel. The sum in the entire circumference of the projected area of the convex structure to the surface perpendicular to the upper surface of the channel means for example, an area obtained by integrating the projected area obtained by projecting the convex structure to the surface perpendicular to the upper surface of the channel, along the circumference of the convex structure, when the side surface of the convex structure is an inclined surface or the perpendicular surface relative to the upper surface thereof. Thereby, it becomes possible to more surely prevent the channel from being crushed by the deflection of the lid. And, it becomes possible to increase the contact area, consequently the friction resistance between the sample in the channel and the convex structure. Therefore, it becomes possible to hold the sample in the channel when removing the lid or in the experimental procedure that follows.

The chip of the present invention may be the chip in which the area of the upper surface of the convex structure is larger than 0.06% of the area of the upper surface of the channel. Thereby, it becomes possible to more surely prevent the channel from being crushed by the deflection of the lid, when the convex structure is in a columnar structure easy to be fabricated. And, it is possible to increase the contact area, consequently the friction resistance between the sample in the channel and the convex structure. Therefore, it becomes possible to hold the sample in the channel when removing the lid or in the experimental procedure that follows.

The chip of the present invention may have a structure such that the area of the upper surface of the convex structure is larger than the area of the bottom surface of the convex structure. The structure in which the area of the upper surface of the convex structure is larger than the area of the bottom surface of the convex structure includes an inverse tapered shape or a hammerhead shape. By doing so, the sample may be held in the channel when removing the lid or in the experimental procedure that follows.

The chip of the present invention may be such that the side surface of the channel is a concave structure. By doing so, the sample may be held in the channel when removing the lid or in the experimental procedure that follows.

The chip of the present invention may have a property that the lid loses an adhesive state of the same to the lid by cooling. By doing so, it becomes possible to easily remove the lid by cooling the lid when removing the lid from the substrate. Further, the contamination occurred by the component of the lid remained in the channel and the sample in the channel may be inhibited. And when the sample in the channel is frozen by the cooling, it becomes possible to fix the sample in a state in which the components of the sample are separated. Therefore, it is possible to easily remove the lid while preventing the sample in the channel from being contaminated.

In the chip of the present invention, the lid may include a partition wall structured so as to cover the channel and a liquid filling a space formed between the sample in the channel and the partition wall. By doing so, it is possible to prevent a clearance from generating between the sample in the channel and the lid. Therefore, the sample may be more surely prevented from leaking and drying.

In the chip of the present invention, a gravity of the liquid may be smaller than a gravity of the sample in the channel. By doing so, mixture of the liquid and the sample may be inhibited and the sample may be surely covered with the liquid.

In the chip of the present invention, a coagulation point of the liquid may be lower than a coagulation point of the sample in the channel. By doing so, only the sample may be selectively coagulated. Therefore, it becomes possible that the liquid is removed and the upper portion of the channel is opened in a state in which the sample is fixed.

According to the present invention, there is provided the chip structured such that the channel is formed inside thereof, the groove is provided on the surface thereof, and a portion of the channel is opened when fractured along the groove.

Since the chip of the present invention is structured such that a portion of the channel is opened when fractured along the groove, the channel may be opened by fracturing the chip at a desired timing. Therefore, it becomes possible to directly operate the sample in the channel. And the sample may be prevented from being contaminated when opening the channel. Meanwhile, a position and a direction to open the channel may be appropriately designed by the position on which the groove is provided.

The chip of the present invention may include the substrate on the surface of which is provided with the channel and the lid covering the channel, and the groove may be provided on at least either of the substrate and the lid. By doing so, it becomes possible to fracture the chip along the notch and allow the channel formed on the surface of the substrate to be exposed from a notch side. Therefore, it is possible to surely open a minute space and directly perform an operation to the sample. And, it is possible to separately fabricate the substrate on the surface of which is provided with the channel and the lid, and combine them. Consequently, a flexibility of a chip design may be improved. And the chip may be stably fabricated. In the present invention, the notch may be provided on a surface horizontal to the surface on which the channel is provided.

The chip of the present invention may be structured such that the lid covers the channel by being joined to the substrate, the notch running from a non-contacting surface with the substrate to a contacting surface with the substrate along a forming direction of the channel is provided on the non-contacting surface, and the channel is opened when being fractured along the notch. By doing so, the channel may be easily opened also when the lid is fractured from the notch. And the contamination of the channel when opening may be inhibited.

In the chip of the present invention, the notch may further be provided on the bottom surface of the substrate along the forming direction of the channel. By doing so, the substrate and the lid may be surely fractured by a smaller force, thereby opening the channel.

In the present invention, the lid may be fractured from the notch by freeze-expanding the sample in the channel. By freezing the sample, the channel may be easily opened without adding an external force.

In the chip of the present invention, a porous layer may be provided on the surface of the lid contacting with the substrate. By doing so, the contamination of the sample in the channel when detaching the substrate and the lid is inhibited, and on the other hand, it becomes possible to surely transfer the sample in the channel to pores in the porous layer to transcribe the same to the lid, when adding the external force in a direction perpendicular to the surface of the substrate. Therefore, it becomes possible to easily take the sample in the channel out of the channel. In the chip of the present invention, the external force added in the direction perpendicular to the surface of the substrate may be, for example, a voltage.

In the chip of the present invention, the substrate may be composed of the porous material. By doing so, the sample in the channel may be easily transferred to the lid by adding an air pressure in the direction perpendicular to the substrate.

In the chip of the present invention, the sample in the channel may be in a frozen state. By doing so, the contamination such as mixture of the components of the sample in the channel may be inhibited. Especially, the mixture of the components spatially separated in the sample by performing the process such as separation to the sample in the channel is inhibited. And when removing the lid, the sample may be prevented from leaking through the minute clearance generated between the lid and the substrate.

A device using the chip of the present invention may include at least the chip and a mechanism which fixes the sample in the channel in the channel. By doing so, an operation for fixing the sample in the channel becomes easier.

The device using the chip of the present invention may be provided with the chip, the mechanism which fixes the sample in the channel in the channel, and a mechanism which opens a region including the contents of the channel sealed by the lid. By doing so, the operations to fix the sample in the channel and to open the channel become easier.

The device using the chip of the present invention may be provided with the chip, the mechanism which fixes the sample in the channel in the channel, the mechanism which opens the region including the sample in the channel sealed by the lid, and a solvent drying mechanism. By doing so, the operations to fix the sample in the channel, to open the channel, and to dry the sample in the channel are performed by the device, so that the operation becomes easier.

The device using the chip of the present invention may include the chip and the mechanism which fixes the sample in the channel in the channel. And the mechanism which fixes, may fix by causing a loss of fluidity of the sample in the channel. By doing so, it becomes possible to fix by causing a loss of fluidity of the sample in the channel, so that the operation becomes easier.

The device using the chip of the present invention may include the chip and the mechanism, which fixes the sample in the channel in the channel. And the mechanism, which fixes, may especially be a chip cooling mechanism in which the solution in the channel is frozen. By doing so, it becomes possible to freeze the sample in the channel, thereby loosing the fluidity of the sample in the channel. Therefore, the operation for fixing becomes easier.

The device using the chip of the present invention may include the chip, the mechanism, which fixes the sample in the channel in the channel, the mechanism, which opens the region including the sample in the channel sealed by the lid, and the solvent drying mechanism. And the solvent drying mechanism is composed of a sealed vessel and a mechanism, which especially depressurizes an inside of the sealed vessel to a pressure at which the solvent may be sublimed. By doing so, the operation for subliming the solvent of the sample in the channel in a state in which the sample in the channel is fixed and the channel is opened.

The device using the chip of the present invention may include the chip, the mechanism, which fixes the sample in the channel in the channel, the mechanism, which opens the region including the sample in the channel sealed by the lid, and the solvent drying mechanism. And the solvent drying mechanism may especially be a mechanism for heating the chip up to a temperature at which the solvent may be evaporated. By doing so, the operation for evaporating the solvent of the sample in the channel in a state in which the sample in the channel is fixed and the channel is opened.

According to the present invention, there is provided the method of using the chip in which the channel is opened after fixing the sample in the channel. By doing so, a movement of the sample in the minute space when detaching the lid from the substrate may be inhibited. Therefore, the contamination of the sample may be further preferably inhibited. And the present invention may include the groove-like channel formed on the surface of the substrate and a removable lid covering the channel, in which the channel may be opened after fixing the sample in the channel in a state in which the channel is covered.

In the method of using the chip of the present invention, the sample in the channel may be solidified by being frozen. By doing so, the sample in the channel may be easily immobilized. Therefore, the contamination of the sample may be easily inhibited.

Meanwhile, in the chip according to the present invention, when adding a predetermined operation to the sample in the channel, although this may function by adding an external force, it is preferable that predetermined components automatically transfer according to a flow of the sample. By doing so, operations such as separation and analysis of the sample may be performed by the structure of the chip itself, without using an external driving device. Such a structure may be realized by utilizing the capillary phenomenon or the like as a driving power to transfer the liquid.

According to the present invention, there is provided the method of using the chip in which the sample in the channel is dried naturally after opening the channel. According to the structure, the sample in the channel may be dried without being contaminated, so that a handling of the chip may be improved.

According to the present invention, there is provided the method of using the chip in which the sample in the channel is freeze-dried after opening the channel. According to the structure, the sample in the channel may be dried without being contaminated, even if the sample in the channel is large in amount, so that a handling of the chip may be improved.

In the method of using the chip of the present invention, when adding the external force in the direction perpendicular to the surface of the substrate, it becomes possible to surely transfer the sample in the channel to the pores in the porous layer to transcribe the same to the lid. By doing so, the sample in the channel may be easily immobilized. Therefore, the contamination of the sample may be inhibited easily. And, the sample in the channel may be taken out of the channel easily.

As described above, according to the present invention, there is provided the technology to open the channel without contaminating the sample in the channel formed on the chip.

BRIEF DESCRIPTION OF THE DRAWINGS

The above-described object, and other object, characteristic and advantage may be more apparent by the preferred embodiments to be described below, and the following attached drawings.

BEST MODE FOR CARRYING OUT THE INVENTION

Figure 1:
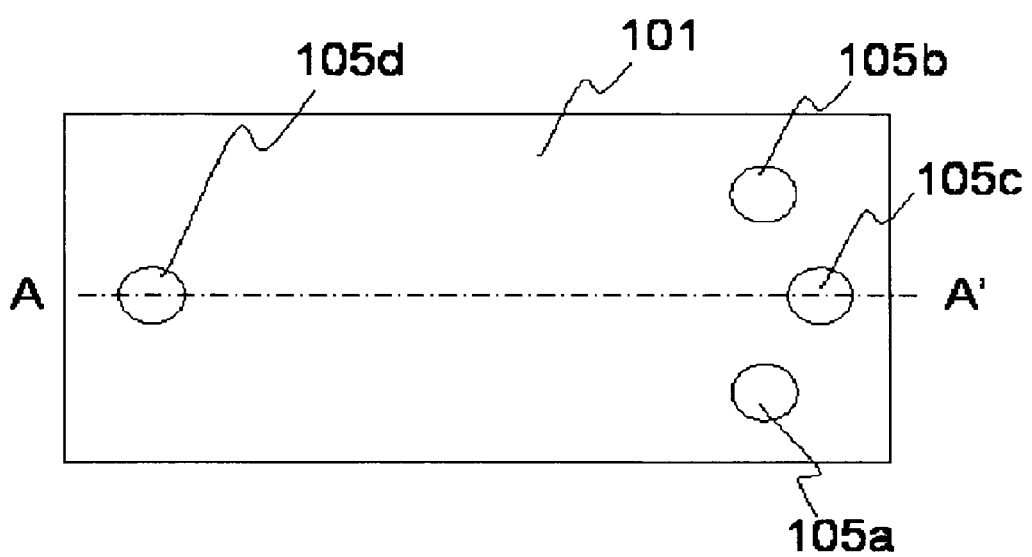
FIG. 1 is a top view showing components of a chip according to an embodiment.

Hereinafter, an embodiment of the present invention will be described with reference to the drawings. Meanwhile, same reference numeral is given to a common component, and a description thereof will not be appropriately repeated.

In the present invention, a chip has a channel, and the channel may be opened. And it is structured such that a contamination of a sample in the channel is inhibited when the channel is opened. Hereinafter, in the chip of the present invention, a case in which the channel is a channel groove provided on a surface of a substrate will be described as an example. A use of the channel is not limited to the channel in an aspect in which the groove is formed on the surface of the substrate. For example, the channel may be a reservoir, such as a reaction reservoir in which a predetermined reaction is performed to the sample and a detection reservoir in which a component in the sample is detected, or may be in another aspect. And, an extended zone may be provided on a portion of a groove-like channel. At this time, the extended zone may be the above-described reaction reservoir and detection reservoir, and the other zone may be the channel.

Although the chip of the present invention may be applied to various sorts of operations such as separating, analyzing, dispensing, diluting, and the like, hereinafter, a case in which components in the sample are separated in the channel of the chip will be described as an example unless especially indicated otherwise. Hereinafter, embodiments of the present invention will be described with reference to the drawings. And in all the drawings, same reference numeral is given to a same component, and a description thereof is not appropriately repeated.

First Embodiment

Figure 2:
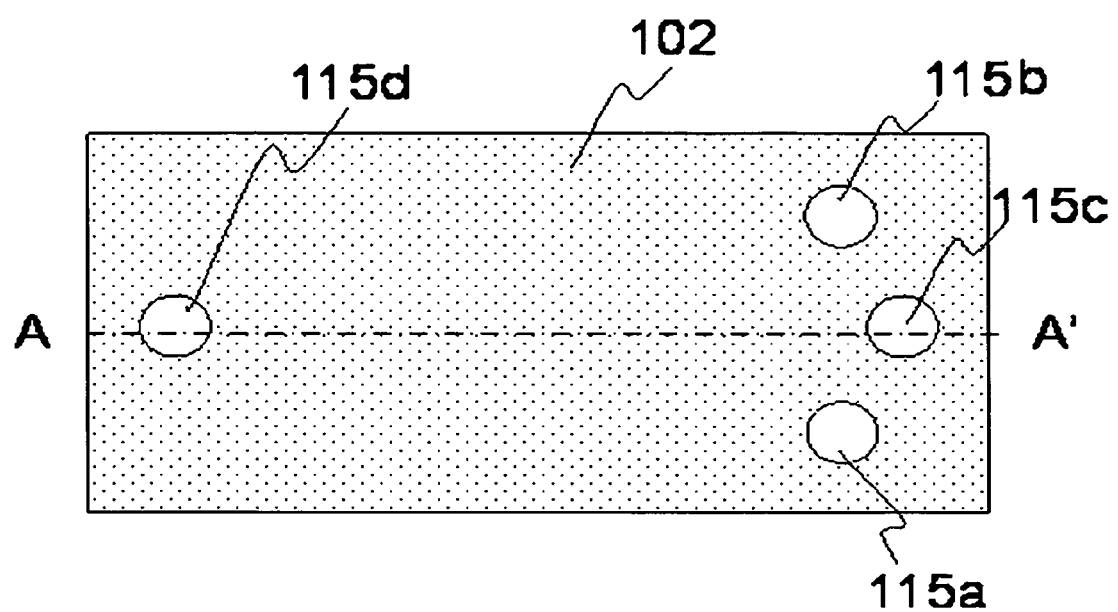
FIG. 2 is a top view showing components of a chip according to an embodiment.
Figure 3:
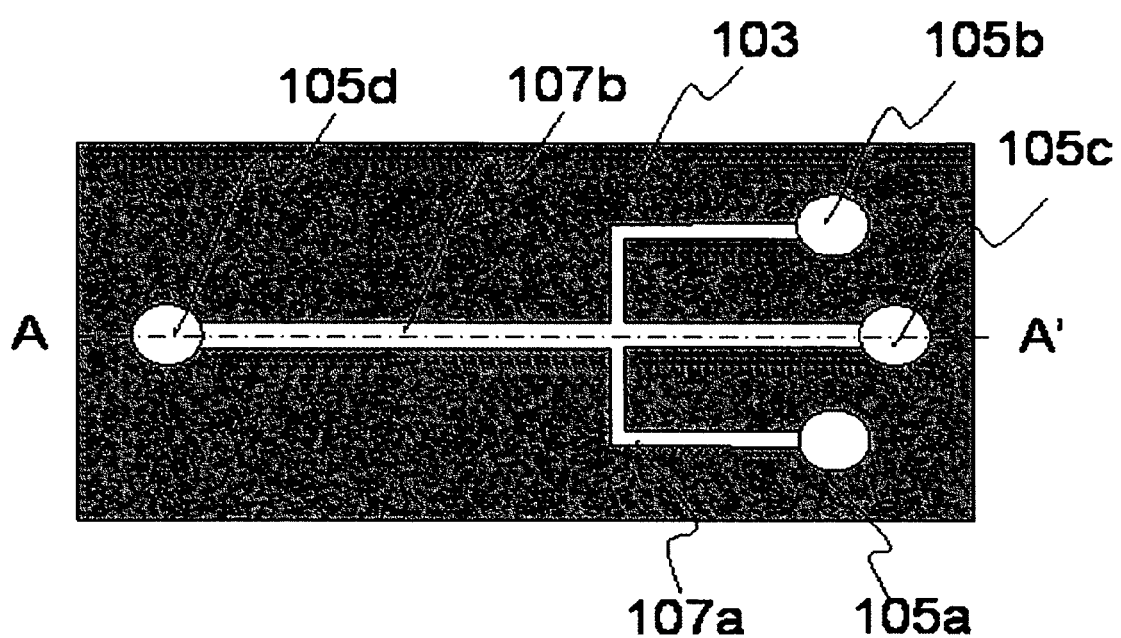
FIG. 3 is a top view showing components of a chip according to an embodiment.
Figure 4:
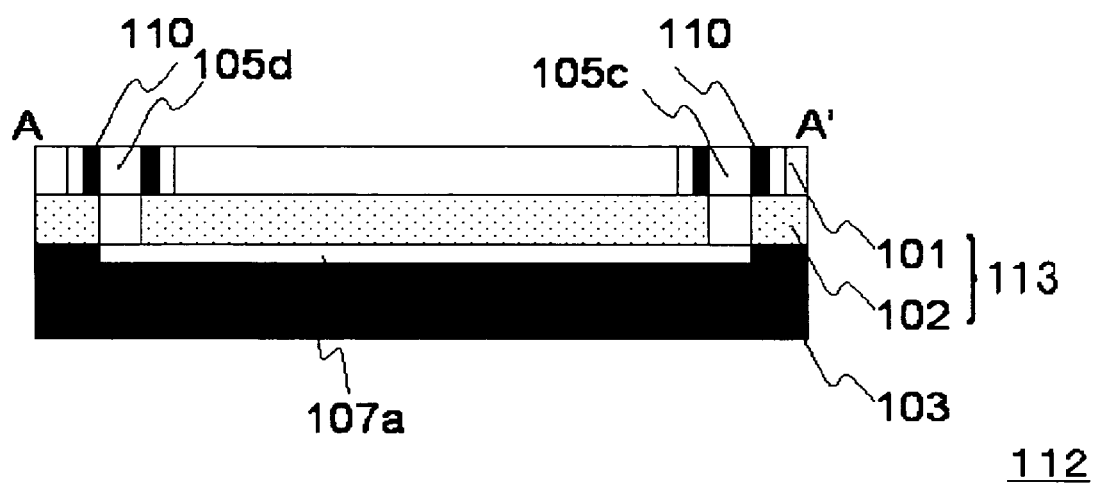
FIG. 4 is a cross-sectional view showing components of a chip according to an embodiment.
Figure 5:
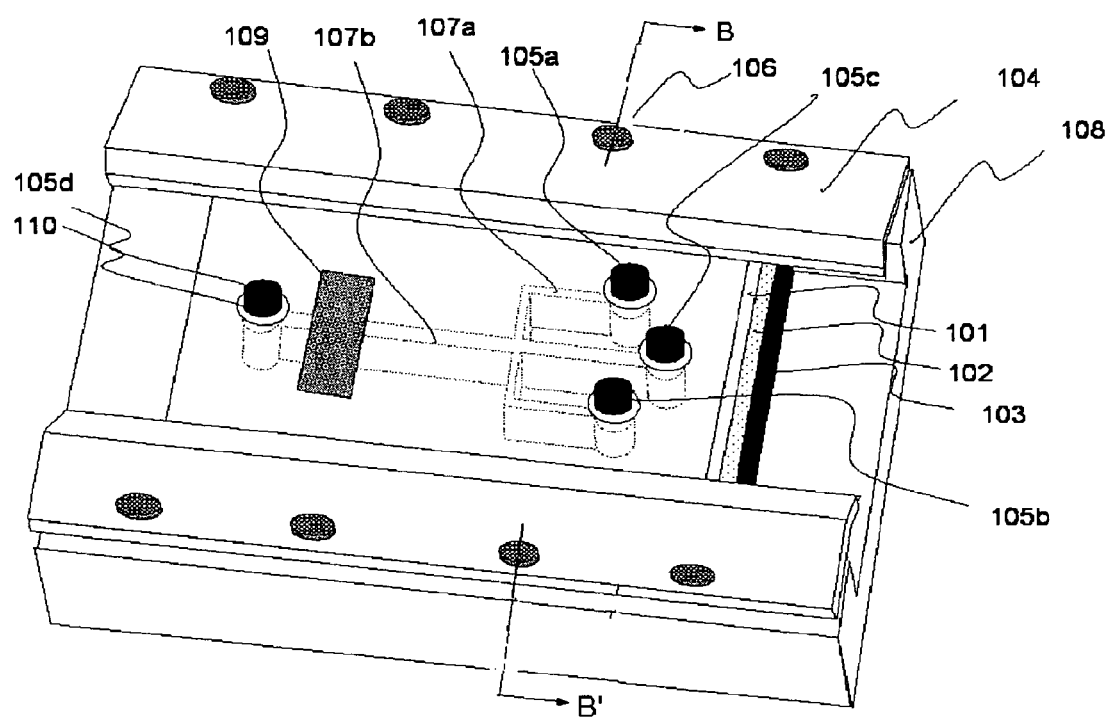
FIG. 5 is a perspective view showing a state in which a chip according to an embodiment is fixed to a fixing device.
Figure 6:
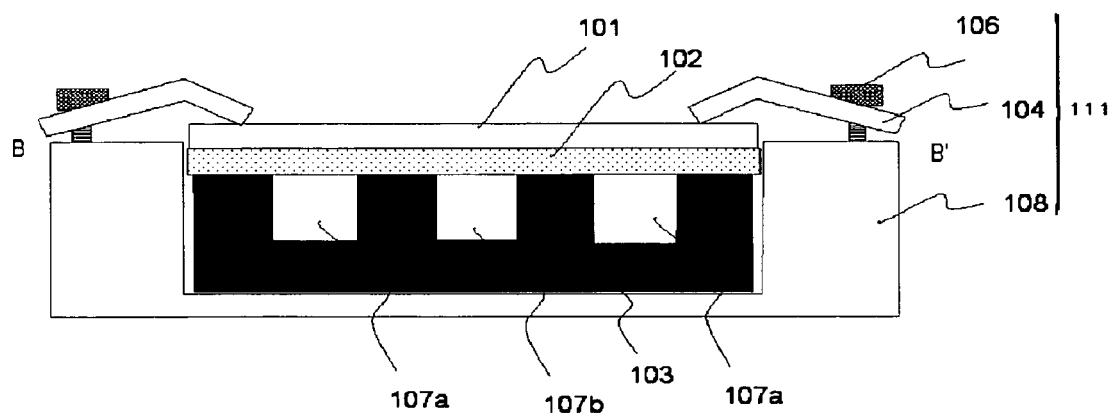
FIG. 6 is a cross-sectional view taken along line B-B' in FIG. 5.
Figure 48:
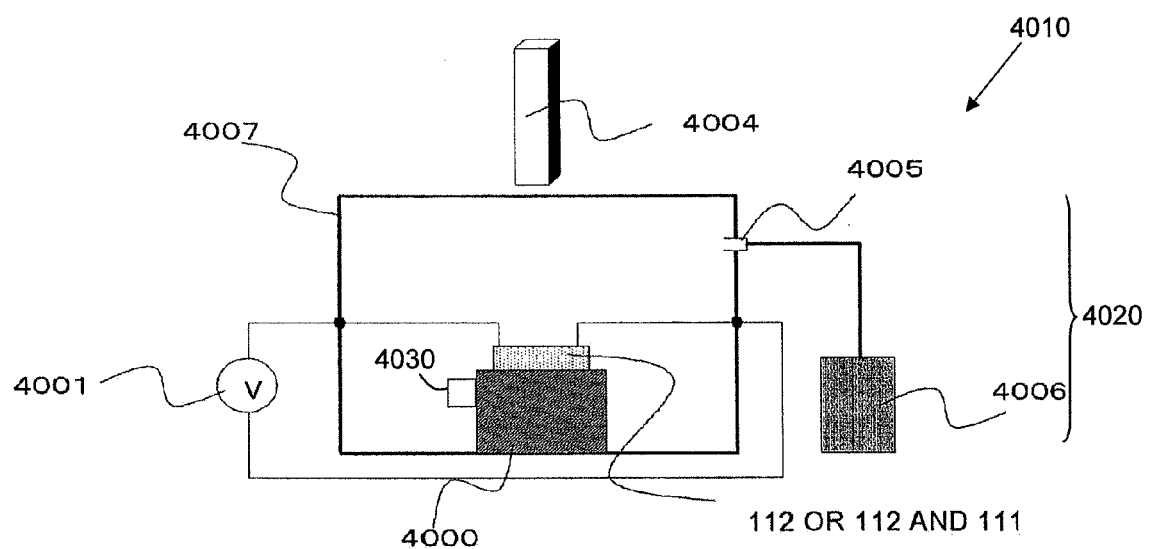
FIG. 48 is a view showing a structure of a device using a chip according to an embodiment.
Figure 49:
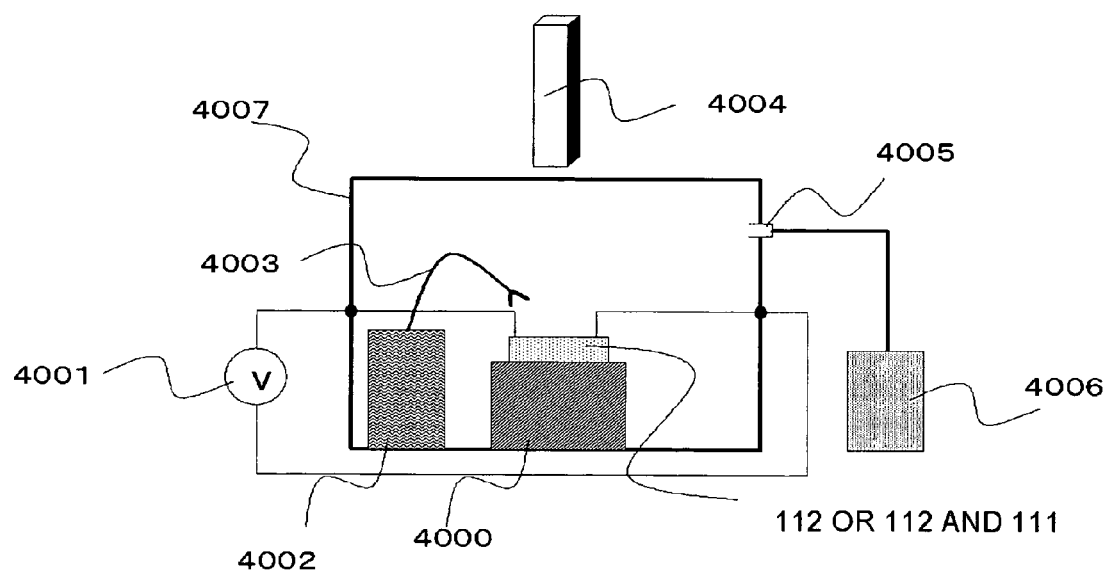
FIG. 49 is a view showing a structure of a device using a chip according to an embodiment.

This embodiment relates to a chip, in which a lid covering a channel provided on a surface of a substrate is mounted on the surface of the substrate. FIGS. 1 to 3 are top views each showing components of the chip of this embodiment. FIG. 4 is a cross-sectional view taken along line A-A' in FIGS. 1 to 3, showing a state in which a chip 112 of this embodiment is assembled. FIG. 5 is a perspective view showing a state in which the chip 112 of this embodiment is fixed to a fixing device, and FIG. 6 is a cross-sectional view taken along line B-B' in FIG. 5. FIG. 48 is a view showing a device using the chip of this embodiment. FIG. 49 is a view showing the device using the chip of this embodiment. Hereinafter, the chip of this embodiment will be described with reference to FIGS. 1 to 6, 48, and 49.

As shown in FIG. 4, the chip 112 includes a substrate 103 and a lid 113. The lid 113 includes a resin layer 102 and a plate-like lid 101, which may be joined to each other. And the plate-like lid 101 is made of resin and may be made of the resin layer 102. Sizes of the plate-like member 101, the resin layer 102, and the substrate 103 may be made substantially equal.

As shown in FIG. 3, channels 107a and 107b are formed on the substrate 103, and reservoirs 105a and 105b, and 105c and 105d are formed on both ends of the channels, respectively. The channels 107a and 107b correspond to the above-described channels. Herein, the channel 107a is the channel for introducing, and the channel 107b is the channel for separating. Materials capable of being microfabricated such as quartz, glass and silicon are preferably used as a material of the substrate 103.

As shown in FIGS. 1 and 2, on the plate-like lid 101 and the resin layer 102, holes 115a, 115b, 115c and 115d each having a size substantially equal to that of the reservoirs 105a, 105b, 105c and 105d provided on the substrate 103, are provided on portions corresponding to the reservoirs. A running buffer can be introduced into the channels 107a and 107b on the substrate 103 through the holes 115a to 115d. And, electrodes for electrophoresis are placed.

Meanwhile, pipes 100 each having an outer diameter equal to an inner diameter of each of the holes 115a to 115d may be provided in each of the holes. By providing the tubes 110, a depth of each of the holes 115a to 115d may be easily adjusted by adjusting a length of the tube 110. For example, by projecting the tube 110 compared to an upper surface of the plate-like lid 101, holes 115a to 115d may be made enough deep. Therefore, when performing electrophoresis, a voltage may be surely applied between the electrodes, while preventing a liquid in the holes 115a to 115d from drying.

As the material of the plate-like lid 101, strong materials capable of being smoothly processed such as quartz, glass, an acrylic resin including PMMA (polymethylmethacrylate) and a silicone resin including PDMS (polydimethylsiloxane);

polyolefin including PTFE (polytetrafluoroethylene), PP (polypropylene), PE (polyethylene) and polyvinyl chloride; polyester;

or the like are preferably used. And as the material of the resin layer 102, PDMS;

polyolefin such as PTFE (polytetrafluoroethylene), PP (polypropylene), PE (polyethylene) and polyvinyl chloride;

acrylic resin;

and polyester are used, for example. As the resin layer 102, the material allowing some elastic deformation, is preferably used. By using the material allowing elastic deformation, it becomes possible to contact with the plate-like lid 101 with the surface of the substrate 103 by applying pressure, thereby surely adhere the resin layer 102 to the surface of the substrate 103. And, as the material of the resin layer 102, the material having water repellency and oil repellency, such as fluorinated resin including PTFE (polytetrafluoroethylene) is preferably used, for example. And, a main portion of the resin layer 102 may be made of another material, and water repellent process or oil repellent process by PTFE or the like may be applied on a surface thereof.

The chip 112 is fabricated as described below, for example. Grooves are formed on the substrate 103 to form the channels 107a and 107b. And the reservoirs 105a to 105d communicating with the channels are formed. The chips and reservoirs are formed by a method suitable for kinds of a material of the substrate 103, such as press-molding using a metal mold including etching and emboss forming, injection molding, molding by light curing or the like, in a case in which a plastic is used as the material of the substrate 103. A width of each of the channels 107a and 107b is set as appropriate according to an operation performed to the sample in the channel. For example, when a high-molecular weight component (DNA, RNA, protein, sugar chain) out of liquid fractionated components (cell cytoplasm) of a cell is extracted, the width may set from 5 μm to 1000 μm. And when bonding the plate-like lid 101 and the resin layer 102, they may be bonded by using an adhesive, or may be heat-sealed. The holes 115a to 115d are formed on an obtained lid 113.

As shown in FIGS. 5 and 6, the chip 112 of this embodiment may be fixed to a fixing device 111. The fixing device 111 has a retainer plate 104, a board 108 on which the substrate 103 is placed, and a screw 106 capable of adjusting a pressure to clamp the retainer plate 104.

As the material of the fixing device 111, strong materials such as aluminum, stainless steel (SUS), titan, and the like are preferably used. And in a case in which the chip 112 applied to the fixing device 111 is the chip for electrophoresis, a surface of the fixing device 111 may be covered with an insulating material such as epoxy resin.

By using the fixing device 111, the lid 113 of the chip 112 may be fixed on the substrate 103. At this time, the lid 113 is clamped against the substrate 103 to be fixed, so that they may be stably fixed by adhering them to each other, in a state in which the channels 107a and 107b are covered, while preventing the sample leaking from the channel.

Next, a method of using the chip 112 of this embodiment is described. First, in order to cover the channels 107a and 107b on the substrate 103, the lid 113 is placed on the substrate 103 while adjusting positions of the reservoirs 105a to 105d and the substrate 103 is installed on the board 108. Next, as shown in FIG. 6, the lid 113 is clamped to the substrate 103, by clamping a portion of the lid 113 by the retainer plate 104 and fastening the screw. The screw 106 is fastened until the resin layer 102 deforms to a certain degree and the channels 107a and 107b are completely covered with the lid 113 with no clearance therebetween. Thereby, the lid 113 is fixed to the substrate 103.

And, when opening the channels 107a and 107b, a pressure to clamp the lid 113 to the substrate 103 is released by loosening the screw 106 of the fixing device 111, and the lid 113 together with the retainer plate 104 are removed. Even in a case in which a small clearance is generated between the substrate 103 and the lid 113, a capillary phenomenon occurred in the clearance is inhibited by structuring the resin layer 102 by a hydrophobic material such as PTFE-based resin and PDMS, and the liquid in the channel is prevented from being contaminated.

In this manner, by using the chip 112 of this embodiment together with the fixing device 111, the lid 113 may be fixed to the substrate 103 by clamping. Thereby, the channels 107a and 107b are surely covered. And, by structuring the surface by the lid 113 of a lyophobic or liquid-repellent material, adhesion of the sample to the lid 113 may be surely inhibited. For example, the surface of the lid 113 may be made hydrophobic or water-repellent. And, since the lid 113 may be easily removed from the substrate 103, it is possible to directly approach the sample in the channels 107a and 107b.

Meanwhile, each of the plate-like lid 101 and the resin layer 102 of the lid 113 may be an independent member.

Meanwhile, the fixing device 111 may be provided with a temperature controlling function. A Peltier or the like may be provided as the temperature controlling function. Thereby, the fixing device 111 may be used when the temperature is required to be controlled in order to improve a separating function when separating the sample. Separating may be performed at a temperature suitable for the separating, by mounting the chip 112 to the fixing device.

And, the fixing device 111 may be used for fixing the sample in the channels 107a and 107b. For example, when the fixing device 111 has a cooling function, it is possible to freeze the sample in the channels 107a and 107b. Therefore, it is possible to fix spatial position of the sample together with components thereof.

Meanwhile, the device for fixing the sample in the channels 107a and 107b may be a sample-fixing device 4000 in FIG.

48. Therefore, when using the fixing device 111 for fixing the sample, this is also the sample-fixing device 4000. And the sample-fixing device 4000 may have only a mechanism for fixing the sample, for example a temperature controlling mechanism or a cooling mechanism for cooling the sample, without having a mechanism for fixing the lid 113.

And, as shown in FIGS. 48 and 49, the fixing device 111 may be provided with a sealed vessel 4007 together with the chip 112. Specifically, the sample-fixing device 4000 may be disposed in the sealed vessel 4007, and the sample-fixing device 4000 may contact only with the chip 112, or with the chip 112 and the fixing device 111.

And as shown in FIGS. 48 and 49, only the chip 112, or the chip 112 and the fixing device 111 may be disposed in the sealed vessel 4007. Specifically, the sample-fixing device 4000 may be disposed in the sealed vessel 4007, and the sample-fixing device 4000 may contact only with the chip 112, or with the chip 112 and the fixing device 111.

And, the sealed vessel 4007 is provided with a valve for vacuuming 4005, and the valve for vacuuming 4005 may be connected to a vacuum pump 4006 by means of a tube made of metal or resin. Thereby, the sealed vessel 4007 can be made into vacuumed state. And, the sealed vessel 4007 is provided with a connector for extending a conductor, which communicates with the electrode of the chip 112, to outside of the sealed vessel 4007, so that a voltage may be applied to the electrode from an external power supply 4001 through the connector.

And, a measurement mechanism 4004 for monitoring a separate state of components of the sample may be provided on outer or inner side of the sealed vessel 4007. A method of detecting the measurement mechanism 4004 may be an optical method. An optical detection may be performed, for example, by combining the components of the sample with a fluorescent material in advance, irradiating the same with a laser along the channels 107a and 107b, and observing the fluorescence emitted from the components of the sample. At this time, the measurement may be performed by using a fluorescent measurement system obtained by combining an X-Y automatic stage, a fluorescence microscope, and a photo multiplier. The X-Y automatic stage is used as a board of the fluorescence microscope. The chip is placed on a stage of the X-Y automatic stage, and an exciting light is irradiated to the channels 107a and 107b through an optical system of the fluorescence microscope. When performing the fluorescent measurement of the channels 107a and 107b, a photon counting is performed by the photo multiplier through the optical system of the fluorescence microscope.

And, the sealed vessel 4007 may be provided with an opening mechanism 4002 shown in FIG. 49, used for removing the lid 113 from the substrate 103. The opening mechanism 4002 may be further provided with a robot arm 4003 for working to remove the lid 113. Meanwhile, the opening mechanism may be provided with not only the robot arm but also a pair of vacuum tweezers. By using the robot arm 4003, the screw 106 fixing the lid 113 is taken off to remove the retainer plate 104.

Meanwhile, the structure shown in FIGS. 48 and 49 will be described later in a twelfth embodiment.

FIGS. 5 and 6 are described again. By providing predetermined channel and reservoir on the chip 112, desired operations such as separating and analyzing may be performed to the sample and the components of the sample. For example, it is possible to sequentially perform electrophoresis and a mass spectrometry by using the chip 112. In this case, the chip 112 is first mounted to the fixing device 111, and in a state in which the channels 107a and 107b are completely covered with the lid 113, a migration buffer is introduced from one of the reservoirs 105a to 105d to fill the channels 107a and 107b with the same.

Next, a migration sample is introduced into the reservoir 105a of the channels 107a. Then, platinum electrodes are inserted into the reservoir 105a to 105d. When applying a voltage between the reservoirs 105a and 105b through the platinum electrodes, the sample within the reservoir 105a flows out in a direction of the reservoir 105b, and fills the channels 107a. At this moment, a rectangular shaped, lengths of which are approximately same as widths of the channels 107a and 107b, that is to say, a narrow band-shaped sample exist on an intersection of the channels 107a and 107b. In this state, a voltage is applied between the reservoirs 105c and 105d, thereby separating the components of the sample in the channel 107b by the electrophoresis.

After a separation by the electrophoresis, the sample and the migration buffer are cooled and frozen by using the temperature controlling mechanism provided in the fixing device 111. The components of the sample are inhibited from being mixed by freezing them. At this stage, the chip 112 is frozen, and the frozen sample and the components thereof, and the frozen migration buffer are stored in the channels 107a and 107b, respectively.

The platinum electrodes are taken off, the screw 101 of the fixing device 111 is loosen, the retainer plate 104 and the lid 113 are taken off, by the robot arm 4003 of the opening mechanism 4002, while keeping the sample and the migration buffer in the channel in a freezing state by means of the temperature controlling mechanism provided in the fixing device 111, thereby making the channels 107a and 107b a opening state.

Following this, the mass spectrometry is performed to the components in the sample after migration, but since the sample frozen by cooling the substrate 103 is difficult to handle, it is preferable that solvent in the sample is dried. For example, when the frozen sample is detached from the fixing device 111, this easily melts with an increase of temperature, and the components of the sample are diffused. Therefore, a method of drying the solvent in the sample while keeping the components of the sample separated, is required.

In a case in which a volume of the sample is very small, it is possible to dry the substrate 103 without contamination, only by heating the substrate 103 by the temperature controlling function provided in the fixing device 111.

But, in many cases, by only heating the substrate 103, a portion in which the sample melts and a portion in which the sample is evaporated are generated in the frozen sample. On the substrate 103 in such state, phenomena that the portion in which the sample melts flows into the channel of the portion in which the sample is evaporated, or that the sample is mixed in the portion in which the sample is melted occur, and the separated components of the sample are diffused. In order to solve the problem, the frozen sample is not melted and the solvent thereof is sublimed.

In this embodiment, the sample after migration may be further freeze-dried, and the solvent thereof may be sublimed.

The solvent drying mechanism 4010 is composed of a sealed vessel 4007 and a mechanism 4020, which depressurizes an inside of the sealed vessel to a pressure at which the solvent may be sublimed.

In a case in which only the substrate 103, or the substrate 103 and the fixing device 111 are disposed in the sealed vessel 4007 (FIGS. 48 and 49), the substrate 103 can be kept frozen by the temperature controlling mechanism of the fixing device 111, or the cooling mechanism of the sample-fixing device 4000. After that, the valve for vacuuming 4005 is opened, and the sealed vessel 4007 is vacuumed by the vacuum pump 4006. Thereby, the solvent of the sample in the channels 107a and 107b may be sublimed. And thereby, the solvent of the sample in the channels 107a and 107b is sublimed, and is dried while keeping the positional relationship of the components of the sample, and not mixing the components to each other.

Following this, the mass spectrometry is performed to the components in the sample which is dried after the separation by the electrophoresis. To perform the mass spectrometry to the components in the channel 107b, the substrate 103, from which the plate-like lid 101 is removed, is taken out of the vessel 4007 if this is disposed in the vessel 4007, and matrix is added to the same, and after drying the substrate 103, this is set to a vacuum chamber of a mass spectrometry device, and is irradiated with a laser after adjusting an irradiating portion such that the channel 107b is irradiated with the laser. Thereby, a molecular mass of the components included in the sample may be found.

Meanwhile, in this embodiment, in addition to the above-described structure, further, the plate-like lid 101 may be made of an elastic body such as the silicone resin and butadiene rubber, and a surface of an obtained plate-like lid 101, which adheres to the substrate 103, may be processed so as to get the closest to the substrate 103 in the vicinity of a center of the plate-like lid 101, and departs farthest away from the substrate 103 in an edge portion of the plate-like lid 101. Thus structured, it becomes possible to remove the lid 113 more smoothly by a force of the elastic body to return to an original form thereof, when a pressure of the fixing device 111 is released.

According to the above structure, the chip capable of covering the channel without a space, and of easily opening without contaminating the solution or the components of the sample in the channel, and the device using the chip can be obtained.

Second Embodiment

Figure 7:
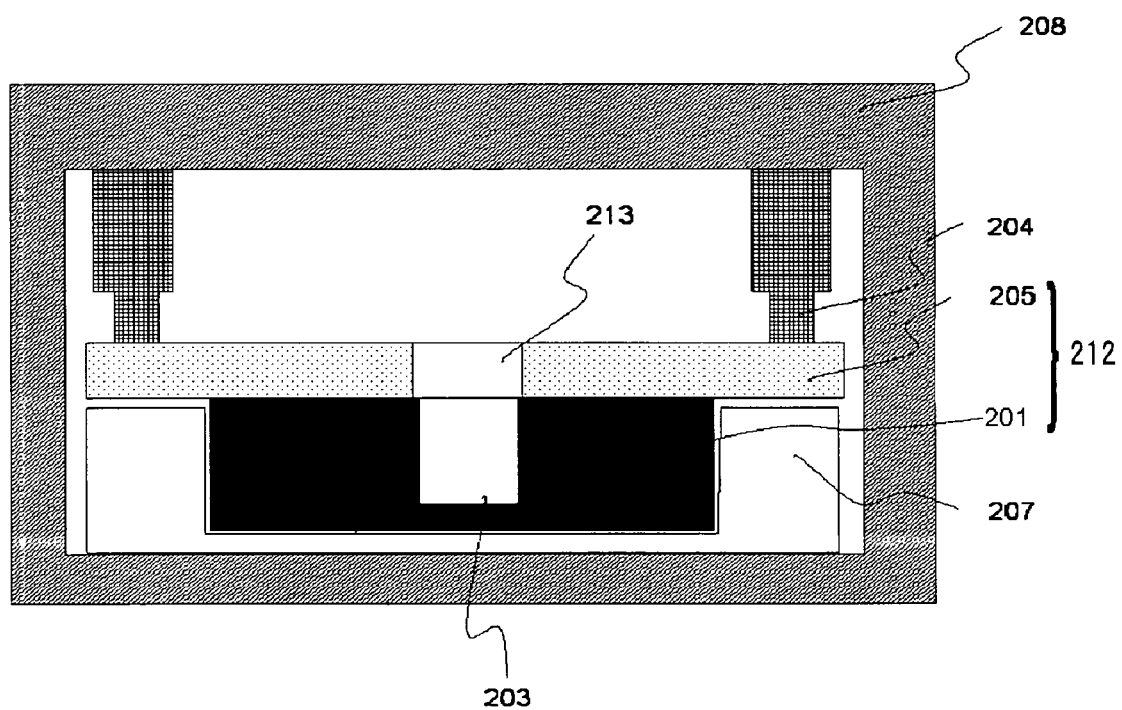
FIG. 7 is a cross-sectional view showing a state in which a chip according to an embodiment is fixed to a fixing device.
Figure 8:
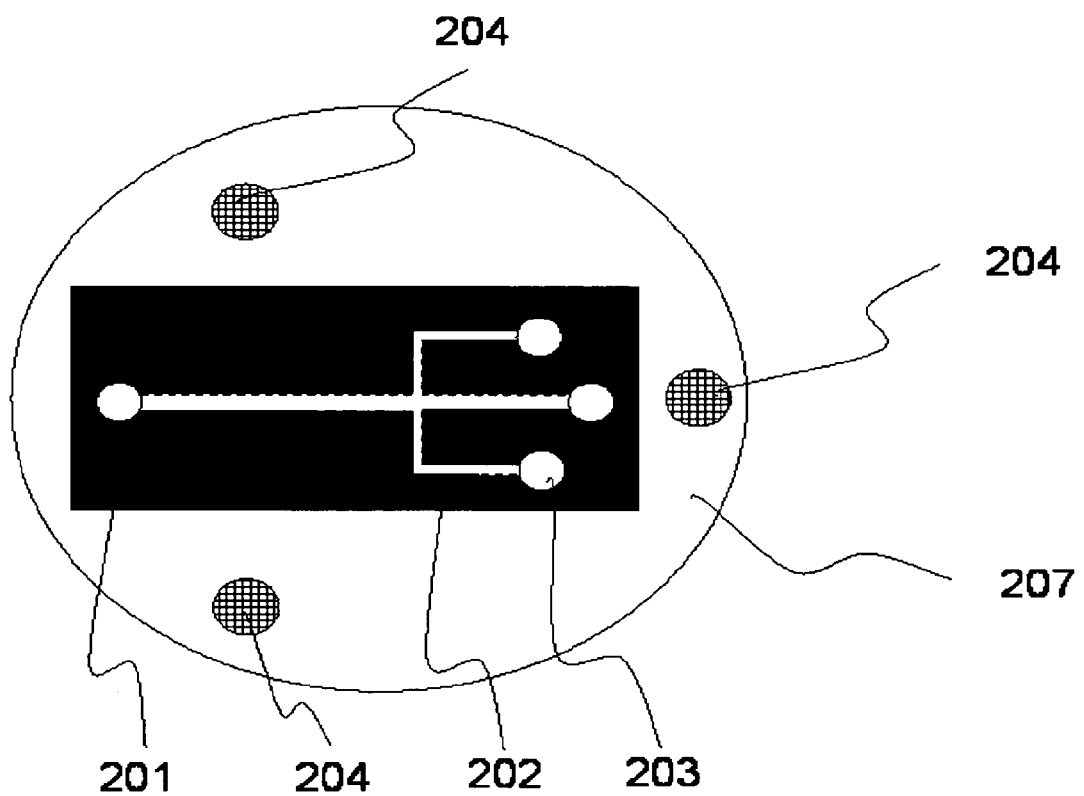
FIG. 8 is a top view showing a state in which a chip according to an embodiment and a board of a fixing device are assembled.

The fixing device for fixing the chip 112 described in the first embodiment is not limited to the above-described structure. For example, pressurization may be performed by a hydraulic pressure device or the like. FIG. 7 is a cross-sectional view showing a state in which the chip according to this embodiment is set to the fixing device. FIG. 8 is a top view showing a state in which the chip and the board of the fixing device are assembled before the lid is set on the chip.

A chip 212 of this embodiment is used by being set to a fixing device 208. The fixing device 208 is structured so as to pressure-weld a lid of the chip 212 to the surface of the substrate by clamping an upper surface thereof. The chip 212 has a substrate 201 and a plate-like lid 205. A channel 202 and a reservoir 203 are formed on the substrate 201. And, a hole 213, having an approximately same size as the reservoir 203, is provided on a reservoir 203 portion of the substrate 201. For example, when the electrophoresis is performed by using the chip 212, the migration buffer may be introduced into the channel 202 on the substrate 201 and providing an electrode (not shown) for the electrophoresis through the hole 213.

A form and a material of the substrate 201 may be set as same as those in the first embodiment. As a material of the plate-like lid 205, strong materials capable of being smoothly processed such as a quartz plate, a glass plate, and an acrylic resin plate or the like may be used. And, by applying water repellent process or oil repellent process to the surface of the plate-like lid 205 on the substrate 201 side by using PTFE-based resin or the like, a leakage is more effectively inhibited.

As the fixing device 208, for example, a desktop servo press device, an oil pressure device, and the like, may be used. As a pressurization piston 204, for example, an hydraulic piston, a water pressure piston, a pneumatic piston, and the like, are preferably used.

An upper portion of the channel in the chip 112, that is to say, the channel 202, is covered by a following process. That is, the substrate 201 is set on a board 207. And the plate-like lid 205 is set on the substrate 201. Then, the plate-like lid 205 is fixed by being held by the pressurization piston 204 and pressurized to downward and fixed. On the other hand, by releasing the pressure of the pressurization piston 204, the lid is taken out of the substrate 201, thereby opening the upper portion of the channel 202.

In this embodiment also, by pressurizing from an upper surface of the plate-like lid 205 in a state in which the substrate 201 and the plate-like lid 205 abut to each other, the upper portion of the channel 202 may be surely covered. Thereby, evaporation of a liquid in the channel 202 may be inhibited. And, by releasing the pressure of the pressurizing piston 204, the plate-like lid 205 may be easily removed from the substrate 201. Thereby, the liquid in the channel 202 after processing may be easily taken out.

The chip 212 of this embodiment is applicable to desired operations such as separating and analyzing as in the first embodiment. For example, when the electrophoresis is performed by using the chip 212, this is performed by a following method. First, the substrate 201 and the plate-like lid 205 are set on the fixing device 208, pressurized by the pressurization piston 204 so as to prevent the migration buffer from leaking, thereby fixing the plate-like lid 205 on the substrate 201. Thereby, the upper portion of the channel 202 is covered. Next, as in the first embodiment, after introducing the migration buffer and the sample from the hole 213, the platinum electrode is inserted from the hole 213 to the reservoir 203, and the electrophoresis is performed. Thereby, the components in the sample may be separated. After the electrophoresis, the electrode is taken off, the pressure of the pressurizing piston 204 is released, and the plate-like lid 205 is taken off.

Third Embodiment

This embodiment relates to a mode in which a lid of a chip having a channel is made of a porous body. In this embodiment, a sample in the channel of the chip is structured so as to be transferred in the porous body. Hereinafter, an example in which a transfer to the porous body is realized by applying a voltage will be described.

Figure 9:
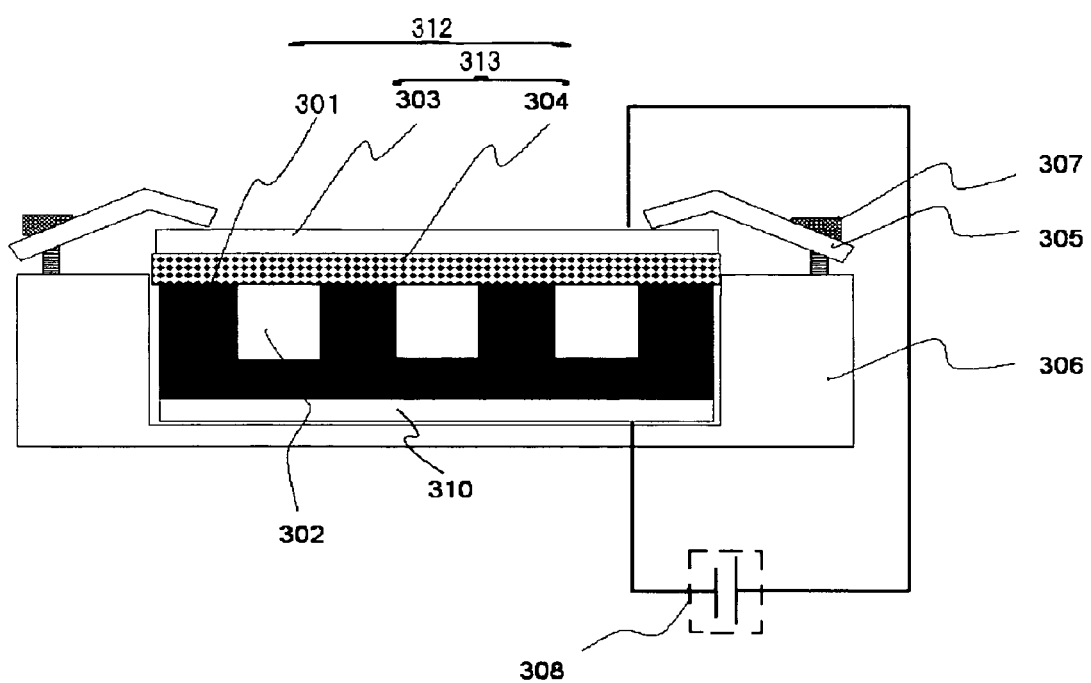
FIG. 9 is a cross-sectional view showing a state in which a chip according to an embodiment is fixed to the fixing device.

FIG. 9 is a cross-sectional view showing a state in which the chip of this embodiment is fixed to a fixing device. In FIG. 9, a chip 312 includes a substrate 301 and a lid 313. A channel 302 is provided on the substrate 301. The channel 302 provided on the substrate 301 is covered with the lid 313. The channel 302 may be the channel and a reservoir, for example. As a material of the substrate 301, a (100) silicon substrate may be used, for example. And a conductive material such as platinum, sintered carbon, or the like may be mold and used for the substrate 301.

The lid 313 is structured such that a porous layer 304 is provided on a surface of a retainer plate 303. The retainer plate 303 may be composed by a conductive material. For example, the retainer plate 303 may be made of a strong metal plate of stainless, brass, and the like with a thickness of few millimeters.

The porous layer 304 may be formed by depositing porous silicon, or by applying silica gel powder and sintering the same, on a lower surface of the retainer plate 303. A material of the porous layer 304 may be a porous material such as porous glass, porous silicon, and the like, for example. And, a thickness of the porous layer 304 may be set from several tens millimeters to several hundreds millimeters. When the material of the porous layer 304 is hydrophilic such as the porous glass, it is possible to prevent the solution in the channel 302 from entering into the porous layer 304, by capillary effect, by applying hydrophobic treatment such as silicone treatment to the surface thereof. And, when the porous layer 304 is formed by conductive porous silicon, and the thickness thereof may set enough thick from several millimeters to several tens millimeters, the retainer plate 303 may be omitted. By setting the chip 312 to the fixing device and pressurizing the same from an upper surface of the lid 313, the channel 302 may be covered with the lid 313.

The fixing device has a fixing board 306, a retainer plate 305, a screw 307 and an electrode 310. A basic structure of the fixing device is similar to the fixing device described in the first embodiment. On the fixing board 306, the electrode 310 is provided on a portion that a bottom surface of a chemical chip abuts so as to apply a voltage between the electrode 310 and the retainer plate 303, when setting the chip 312 to the same. By applying the voltage from a power supply device 308 between the electrode 310 and the retainer plate 303, material in the channel 302 may be transferred to the porous layer 304 of the lid 313. An applying direction of the voltage is different according to a charge of the material in the channel 302. When the material is positively charged, the voltage is applied such that the electrode 310 is a positive electrode and the retainer plate 303 is a negative electrode. And when the material is negatively charged, the voltage is applied in a direction opposite to the above-described direction.

Next, SDS-processed protein will be described as a component in the sample. A method of using the chip 312 is described with an example of a process in which the protein is SDS-treated and recovered. First, the lid 313 composed of the retainer plate 303 and the porous layer 304 is set on the substrate 301, and the retainer plate 303 is interposed between the substrate 301 and the retainer plate 305 of the fixing device, as shown in FIG. 9. And, by fastening the screw 307, the retainer plate 303 is clamped to the substrate 301 and covers the channel 302. In this state, the sample including the protein and SDS are introduced into the channel, the whole device is put in an oven, and the same is heated for approximately an hour at a temperature of approximately 100° C. After the device is cooled down to a room temperature, a direct voltage of approximately 1000V, for example, is applied for approximately 30 minutes, while setting the retainer plate 303 to the positive pole and the electrode 310 set on a bottom plate of the fixing device to the negative pole. Thereby, the negatively charged protein with absorbed SDS is migrated in a direction of the retainer plate 303 and transferred in the porous layer 304. Finally, the screw 307 is loosened to release the pressure of the retainer plate 305, thereby taking off the chemical chip from the fixing device, and the lid 313 is taken off. After that, a desired process such as the mass spectrometry or the like is performed to SDS adsorbed protein transfer-fixed to the porous layer 304 surface of the lid 313.

As described above, by covering the channel 302 of the chip 312 with a detachable lid 313 and by transferring the sample or the components of the sample in the channel 302 to the lid 313 made of the porous body, the chip 312 capable of easily opening the channel 302 while preventing the sample in the channel 302 from contaminating may be obtained. By the fact that the material in the channel 302 is stored in the porous body, it becomes possible to recover the materials and dry the same more quickly, while preventing the spatial position of the components of the sample generated in the channel 302 by the electrophoresis from eliminating by the diffusion or the like.

Meanwhile, although the voltage is used to transfer in the above-described case, an air pressure may be used for transferring the sample when using the chip 312 of this embodiment. In this case, the retainer plate 303 is formed by a breathable material such as a porous glass, for example. And in this case, the retainer plate 303 is not necessarily required to be a conductive material, and it is not required to place the electrode 310 on a bottom surface of the fixing board 306. The substrate 301 also is composed of the breathable material, such as the porous glass, as well as the retainer plate 303. In this case, the contamination when the lid 313 is removed from the substrate 301 may be inhibited by applying hydrophobic treatment to the surfaces of the substrate 301 and the porous layer 304.

When transferring the material by using the air pressure, an end of a pressure-proof tube connected to a suction pump is placed directly above the channel 302 instead of applying the voltage and transferring in the above-described case. Thereby, the solution or material in the channel 302 are sucked in the porous layer 304 and kept there associated with a suction of air through the substrate 301, the porous layer 304 and the retainer plate 303.

Fourth Embodiment

Figure 10:
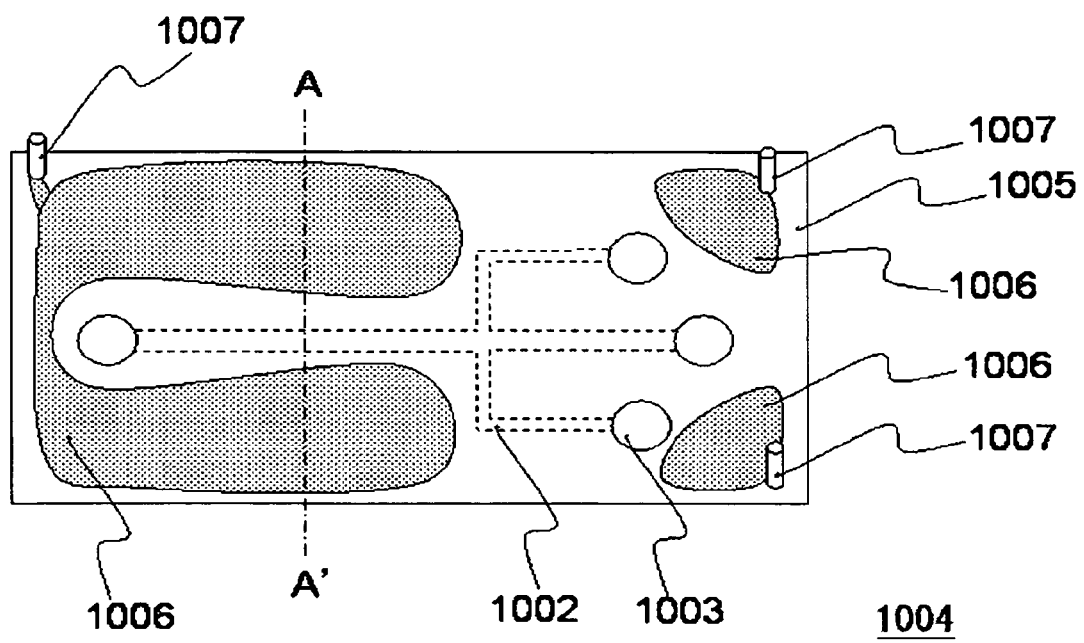
FIG. 10 is a top view showing a structure of a lid of a chip according to an embodiment.
Figure 11:
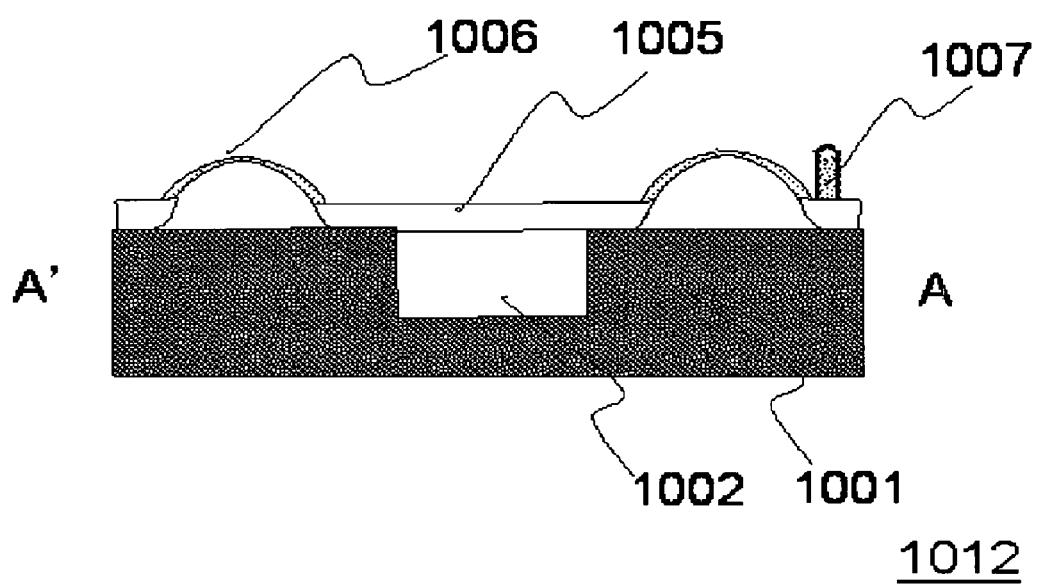
FIG. 11 is a cross-sectional view showing a structure of a chip according to an embodiment.
Figure 12:
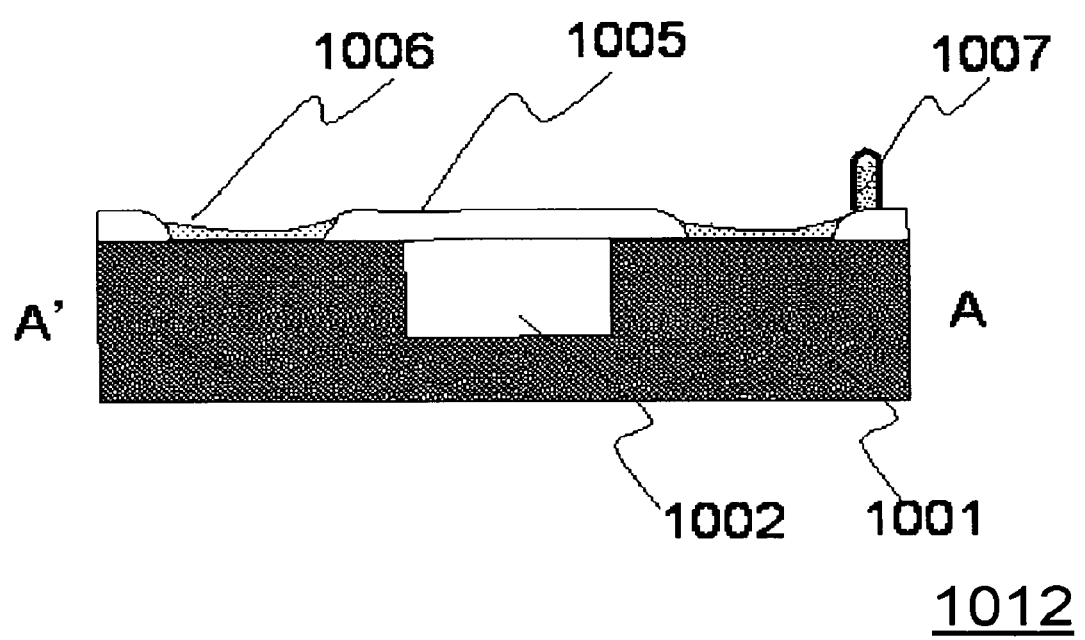
FIG. 12 is a cross-sectional view showing a structure of a chip according to an embodiment.

This embodiment relates to a chip having a lid, which is adsorbed to a surface of a substrate. Hereinafter, the chip of this embodiment will be described with reference to FIGS. 10 to 12. FIG. 10 is a plain view showing a structure of the lid of this embodiment. FIG. 11 is a cross-sectional view showing a state before the lid in FIG. 10 is adsorbed to the substrate. FIG. 12 is a cross-sectional view showing a state in which the lid of FIG. 10 is adsorbed to the substrate.

As shown in FIGS. 11 and 12, a chip 1012 includes a substrate 1001 and a lid 1004. The substrate 1001 is provided with a channel 1002 and a reservoir (not shown).

The lid 1004 is composed of a covering unit 1005 for covering the channel 1002, a sucker portion 1006 for realizing a sucker effect, and a tab 1007 as an aeration unit to the sucker portion 1006. The covering unit 1005 is smoothly shaped, the sucker portion 1006 has a floaty "concave" in a state not to be compressed, and the tab 1007 is provided in the vicinity of the concave. The sucker portion 1006 is formed on a portion other than the channel 1002 and reservoir (not shown). The tab 1007 is located in the vicinity of an edge of the covering unit 1005.

On the covering unit 1005, holes 1003 having the same size as the reservoirs (not shown) are formed on the same positions as the reservoirs of the substrate 1001. The sucker portion 1006 and the tab 1007 may be integrally molded with the covering unit 1005 by injection molding or the like by using materials such as rubber and PDMS.

Next, a method of using the chip 1012 will be described. First, the lid 1004 is placed on the substrate 1001 such that positions of the reservoir and hole 1003 coincide to each other (FIG. 11). Next, the sucker portion 1006 is pressed from above such that the covering unit 1005 is adsorbed to the substrate 1001 (FIG. 12). At this time, the sucker portion 1006 may be adsorbed to the surface of the substrate 1001 by compressing the covering unit 1005 to the substrate 1001 above the channel 1002 so as to allow air escape to an outer peripheral side of the substrate 1001 rather than the sucker portion 1006. By doing so, the covering unit 1005 may be adhered to the upper portion of the channel 1002.

The migration buffer and the sample are introduced from the hole 1003 provided on the covering unit 1005 to the channel 1002 of the substrate 1001 to perform the process such as the electrophoresis. After that, the tab 1007 is drawn up to form a clearance between the substrate 1001 and the lid 1004. By doing so, air is introduced into the sucker portion 1006, so that the channel 1002 is opened by removing the lid 1004 after separating the lid 1004 from the substrate 1001.

Although the sucker portion 1006 is aerated by drawing up the tab 1007 in the above-described case, another aeration unit may be used. For example, the lid 1004 may be separated from the substrate 1001 by making a portion of the resin composing the sucker portion 1006 thin, and penetrating a partition film by a needle or the like to aerate, when removing the lid 1004.

In this embodiment, the channel 1002 on the substrate 1001 is surely covered with the lid 1004 and opened, by providing the salient on the lid 1004 formed by the elastic body to use as the sucker. And, the lid can be attached and detached more easily, by providing the aeration unit to introduce air in the salient in the vicinity of a peripheral portion of the substrate 1001 near the upper surface of the salient on the lid 1004. Therefore, the channel of the chip may be covered and easily opened without using the fixing device.

Meanwhile, a pattern in which the salient of the sucker portion 1006 has a groove as a component, ends of which are closed, may be formed in this embodiment. Thereby, introduction of air into the salient may be more easily. Therefore, the channel 1002 is opened and closed more easily. And, although the aeration unit in a tab-projection shape is used in the above-described case, the aeration unit may be a penetrable partition film composing a part of the lid 1004. By doing so, air is easily introduced into the salient by penetrating the partition film by needling or the like. Therefore, the channel 1002 may be easily opened.

Fifth Embodiment

This embodiment relates to a chip having a partial seal covering a channel of a substrate and silicone resin. Although the lid is completely removed when removing the lid from the substrate in the above-described embodiment, in the chip of this embodiment, the lid is removed only from a portion in the vicinity of the channel desired to be opened.

Figure 13:
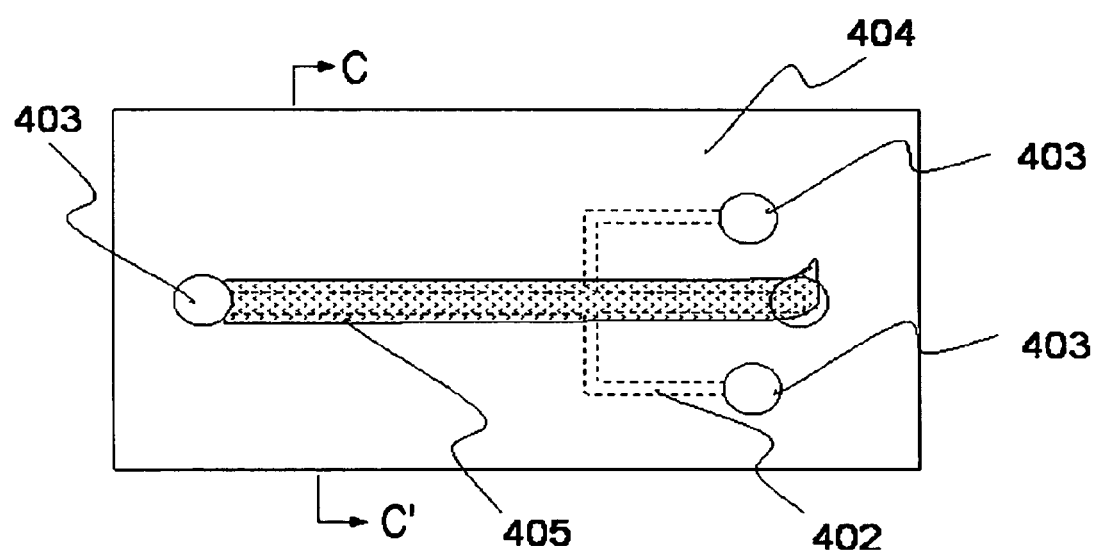
FIG. 13 is a top view showing a structure of a chip according to an embodiment.
Figure 14:
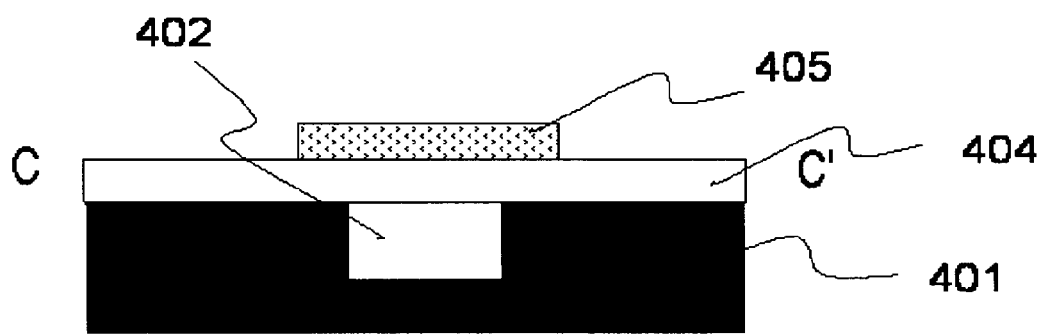
FIG. 14 is a cross-sectional view taken along line C-C' in FIG. 13.

FIGS. 13 and 14 are views showing a structure of the chip according to this embodiment. FIG. 13 is a top view of the chip, and FIG. 14 is a cross-sectional view taken along line C-C' thereof.

The substrate 401 is provided with a channel 402 and reservoirs 403 as the channels, and the channels are covered with a seal 404. The seal 404 is provided with holes 413 on positions corresponding to the reservoirs 403 of the substrate 401, further, on the seal 404 located above the channel 402 of the substrate 401, a rectangular seal 405 is attached. To bond the seal 405, a stronger adhesive than that of the seal 404 is used. And, at least one side of the seal 405 is not attached and liberated, by making a length thereof longer than that of the channel of the seal 404, such that the seal 405 may be easily detached therefrom.

As a material of the seal 404, a resin material film such as polyester and polyethylene may be used. And as a material of the seal 404, a resin film such as high-density polyethylene having a splitting characteristic in one direction may be used. In this case, the seal 404 is preferably attached in a direction in which the seal 404 splits along the channel 402 of the substrate. The seal 404 may be joined to the substrate 401 by being bonded by the adhesive, or by being heat-sealed.

And as a material of a film-shaped seal 405, silicone resin, such as PDMS or the like may be used. By adhesion of the silicone resin, the channel provided on the surface of the substrate may be precisely covered, and further, by water-repellency of the silicone resin, the capillary effect occurred when removing the seal 405 is inhibited, and the sample and the components of the sample in the channel are prevented from being contaminated. Further, a high covering effect by adhesion of the silicone resin may be realized by forming the substrate 401 by the silicone resin.

When using the chip of this embodiment, first, the seal 404 is joined to the substrate 401. At this time, the seal 405 is set to overlap with the channel 402 of the substrate. Next, the migration buffer and the sample are introduced from the reservoirs 403 into the channel 402. Then, the platinum electrodes are inserted to the reservoirs 403, and the components are separated by the electrophoresis of the sample, as in the case of the first embodiment. After the electrophoresis, the migration buffer and the sample in the channel are frozen if required, to provide immobilization of the pattern after separation, then the seal 405 is detached from the end thereof to open the channel 402.

Thus structured, the chip capable of covering and easily opening the channel of the chip while inhibiting the contamination from the channel in the vicinity, without using a special fixing device.

Sixth Embodiment

Figure 15:
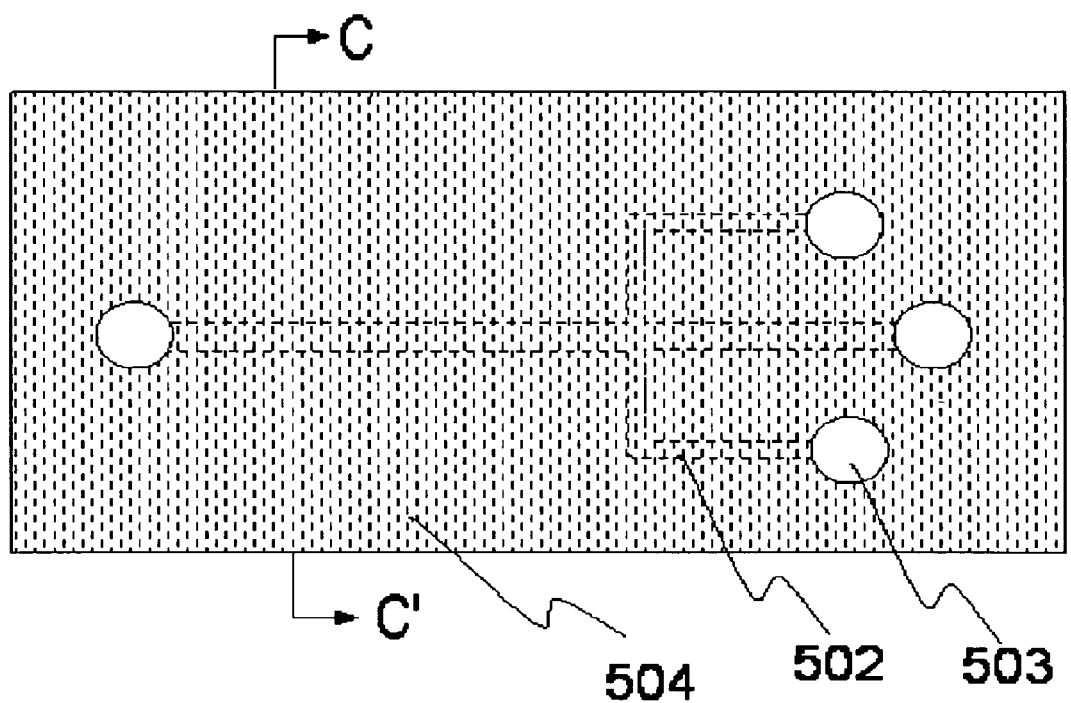
FIG. 15 is a top view showing a structure of a chip according to an embodiment.
Figure 16:
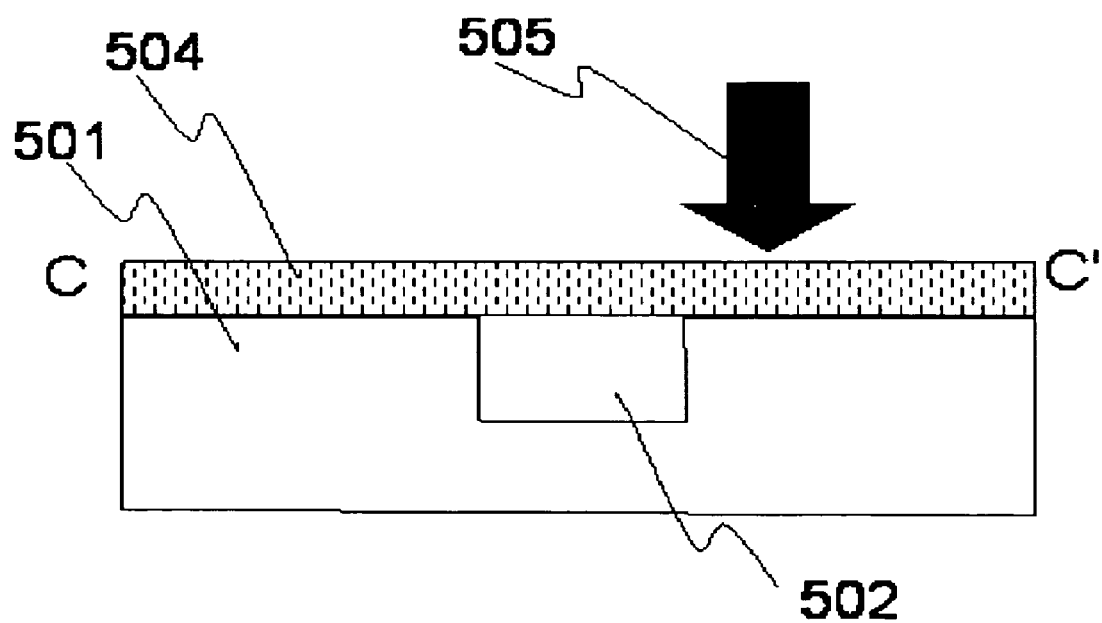
FIG. 16 is a cross-sectional view taken along line C-C' in FIG. 15.
Figure 17:
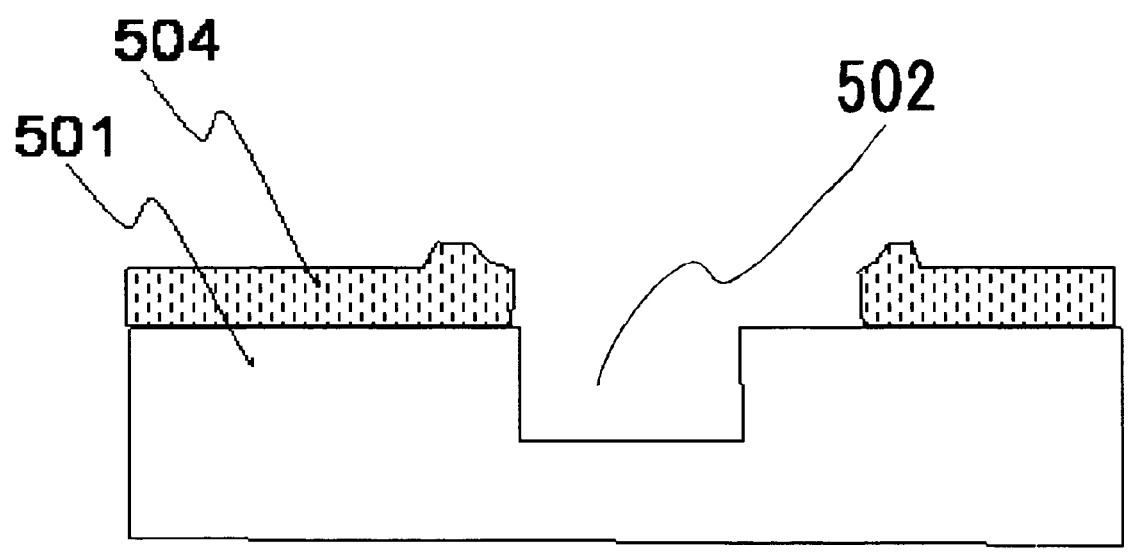
FIG. 17 is a cross-sectional view taken along line C-C' in FIG. 15.

According to the embodiment, a lid is detached from a substrate by using a difference in coefficients of thermal expansion of the lid and the substrate, after adhering the lid to the substrate. FIG. 15 is a top view showing a structure of a chip according to this embodiment. FIGS. 16 and 17 are cross-sectional views taken along line C-C' in FIG. 15. FIG. 16 shows a state in which a channel is covered with the lid and FIG. 17 shows a state in which the covering is removed.

The chip of this embodiment has a substrate 501 and a seal formed by a heat-shrinkable resin, which corresponds to a lid. The substrate 501 is provided with a channel 502 and a reservoir (not shown) as the channels. A surface of the substrate 501 is covered with a heat-shrinkable resin seal 504.

The heat-shrinkable resin seal 504 is provided with holes 503 having a size corresponding to size of the reservoirs (not shown) of the substrate 501, on a position corresponding to the reservoirs. The heat-shrinkable resin seal 504 heat-sealed to the substrate 501 while spreading as shown in FIG. 15.

The chip of this embodiment is used as follows. First, the migration buffer and the sample are introduced from the holes 503 made on the heat-shrinkable resin seal 504 into the channel 502 to perform the electrophoresis. After that, when opening the channel 502, a position slightly outer from an upper portion of the channel 502 desired to be opened is irradiated with a laser along an extending direction of the channel 502 (FIG. 16). Consequently, the heat-shrinkable resin seal 504, which has been spread, is shrunk and broken, so that an upper portion of the channel 502 is opened as shown in FIG. 16.

Meanwhile, the material used as the lid of this embodiment is not limited to the heat-shrinkable resin. For example, a plate-like lid formed by resin, glass and the like having different coefficients of expansion may be used. In this case, the plate-like lid may be bonded to the substrate 501 by an epoxy resin-based adhesive, for example. Also, the lid may be bonded by heat-sealing. When heating or cooling an entire chip, a declination is generated on an interface between the plate-like lid and the substrate 501 by a stress generated by a difference in coefficient of thermal expansion and coefficient of shrinkage, so that adhesion is released, and the plate-like lid may be removed. Further, by limiting the adhesive portion of the plate-like lid and the substrate 501 in the vicinity of the channel, it becomes possible to reduce the stress required for detaching the plate-like lid and the substrate 501, so that the plate-like lid may be more easily removed.

Thus structured, the chip capable of covering and easily opening the channel of the chip without using a special fixing device may be provided.

Seventh Embodiment

Figure 18:
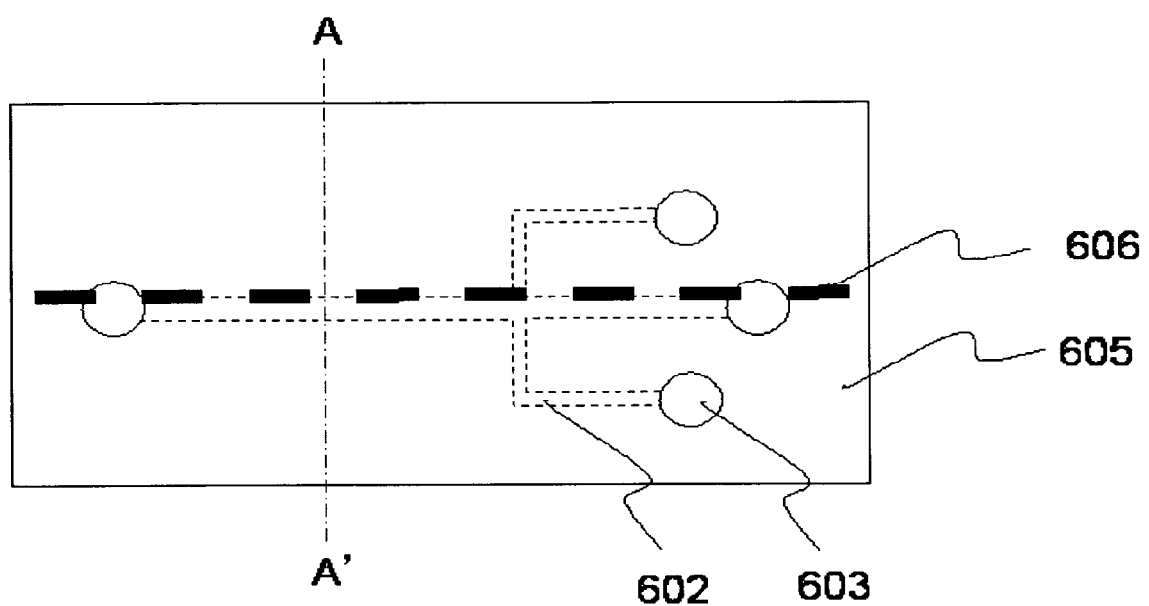
FIG. 18 is a top view showing a structure of a chip according to an embodiment.
Figure 19:
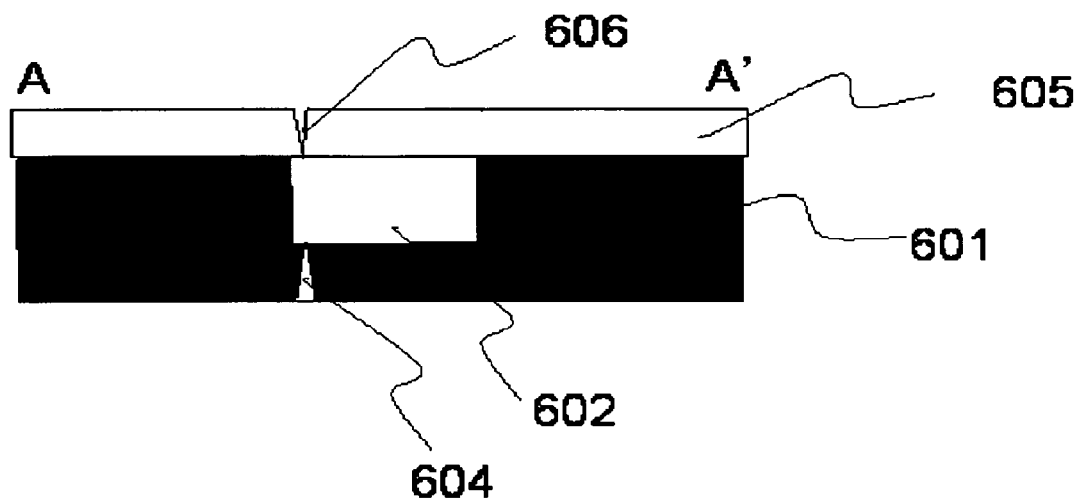
FIG. 19 is a cross-sectional view taken along line A-A' in FIG. 18.

A chip of this embodiment has a cut or a notch to open a channel. The notch is provided so as to open the channel along the same. Herein, it is described with an example in which the chip is fractured to open the channel, after a solution in the channel formed on a surface of the substrate is fixed and immobilized. FIGS. 18 and 19 are views showing a structure of the chip according to this embodiment. FIG. 18 is a top view of the chip, and FIG. 19 is a cross-sectional view taken along line A-A' in FIG. 18.

The chip of this embodiment has a substrate 601 and a lid 605. As a basic structure of the substrate 601, the structure of the substrate used in the chip according to the above-described embodiments may be used. For example, the structure of the substrate 601 may be similar to that of the substrates 103, 201 and 301. A channel 602 and a reservoir 603 are provided on the substrate 601. In this embodiment, a lid 605, which completely adhered to the substrate 601*l* is used. For example, when the substrate 601 is formed by silicon, the lid is made of a Pyrex (registered trademark) glass, and they are completely adhered to each other by electrostatic joining. But adhering method is not limited to this. The lid 605 is provided with holes (not shown) on positions corresponding to the reservoirs 603 of the substrate 601. The substrate 601 and the lid 605 which are provided with notches 604 and 605, respectively, along the channel 602 by using a dicing saw or the like, as shown in FIG. 19 are used.

A depth of a notch 606 may be set not smaller than a quarter-thickness of the lid 605, more preferably, not smaller than two-thirds thickness thereof. By doing so, the lid 605 may be easily fractured by a small force. And, the depth of the notch 606 may be set not smaller than nine-tenth of the thickness of the lid 605, more preferably five-sixth thereof. By doing so, strength of the lid 605 may be assured.

In the above-described structure, an operation of a device of this embodiment is performed as follows. The migrating buffer and the sample are introduced from the holes provided on the lid 605 through the reservoirs 603 to the channel 602 of the substrate, thereby performing the electrophoresis. Next, the migration buffer is frozen, and an external force is added, so that the channel is fractured along the notch 604 of the substrate 601 and the notch 606 of the lid 605 to open the channel 602. By freezing, the sample and the components of the sample in the channel, that is the channel 602, are fixed in the channel 602, so that the channel may be opened while preventing from being contaminated.

Although the sample in the channel is fixed by being frozen in this embodiment, the solution may be coagulated by another method. For example, by filling the channel with a thermo-coagulating polymer solution, for example, the solution having a methylcellulose solution and ovalbumin solution as a ground substance, and heating an entire chip, the solution may be coagulated and fixed.

According to the structure of the embodiment, the chip capable of easily being opened while preventing the solution and the material in the channel provided on the chip from being contaminated may be provided.

Meanwhile, in the above-described case, although the structure in which the notch 606 is provided on both of the substrate 601 and the lid 605 is described, in the chip of this embodiment, the notch 606 is sufficiently provided on at least one of the substrate 601 and the lid 605. By providing the notch 606 to both of the substrate 601 and the lid 605, the chip may be surely fractured to open the channel 602. And, although the case in which the chip is fractured in a direction perpendicular to the surface of the substrate 601 to open a side surface of the channel 602 is described as an example, the notch 606 to open an upper surface of the channel 602 may be provided.

And, although it is structured such that the lid 605 is joined to the surface of the substrate 601 so as not to be removed therefrom, it may be structured such that the lid 605 may be removably joined to the surface of the substrate 601. Thus structured, it becomes possible to appropriately select from removing of the lid 605 and fracturing of the chip, as the method of opening the channel 602. Thereby, it becomes possible to select an opening surface of the channel 602 according to an operation. Therefore, flexibility of the operation when using the chip may be increased. And, it is not limited to a case in which the substrate 601 and the lid 605 are different members, and they may be integrally formed, for example.

Eighth Embodiment

Figure 20:
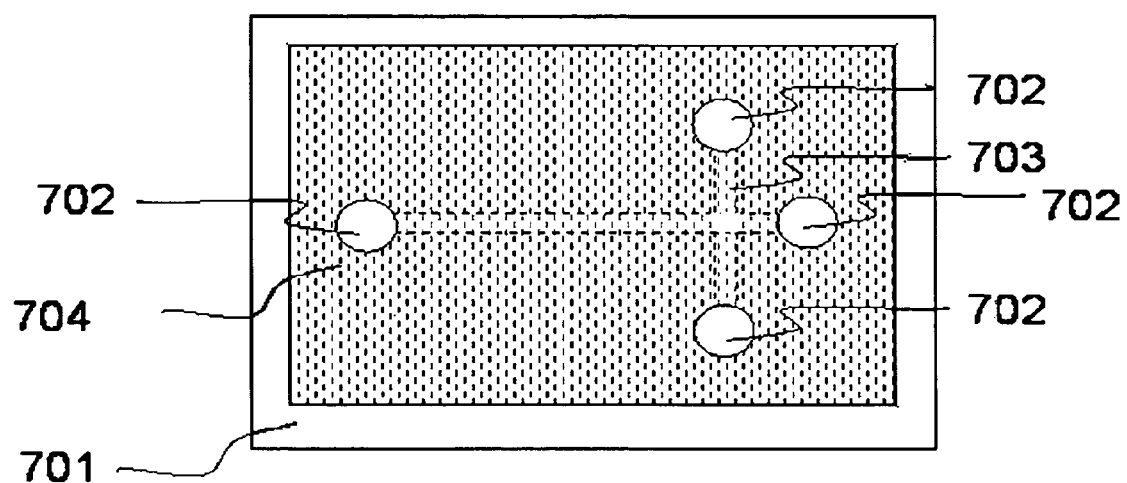
FIG. 20 is a top view showing a structure of a chip according to an embodiment.
Figure 21:
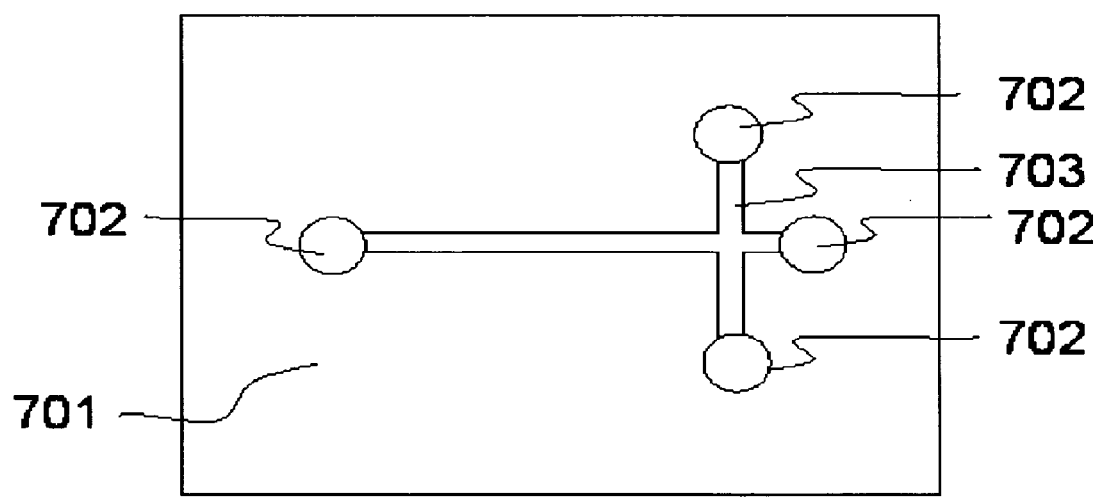
FIG. 21 is a top view showing components of a chip according to an embodiment.
Figure 22:
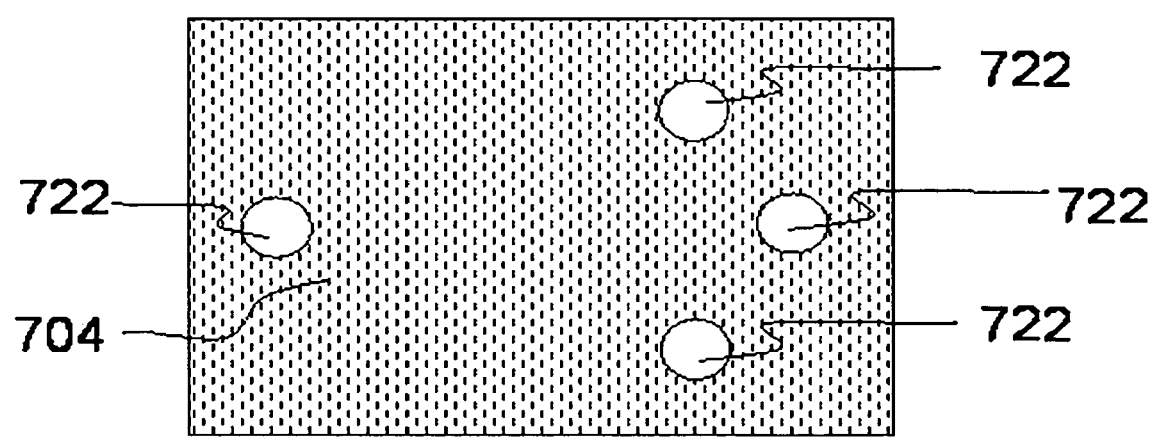
FIG. 22 is a top view showing components of a chip according to an embodiment.
Figure 26:
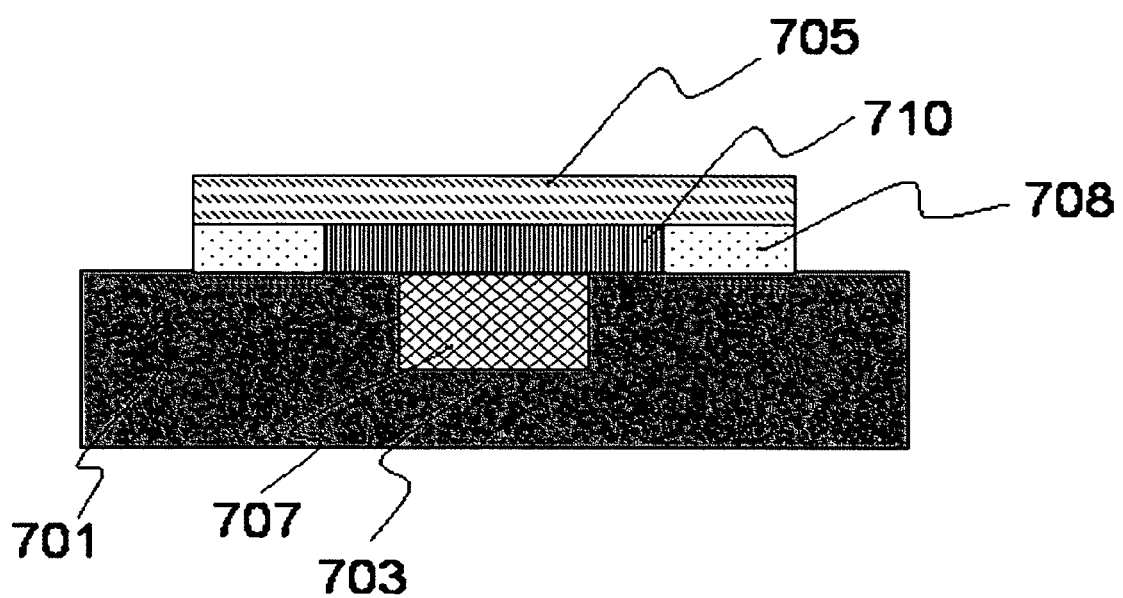
FIG. 26 is a cross-sectional view showing a procedure of using a chip according to an embodiment.
Figure 27:
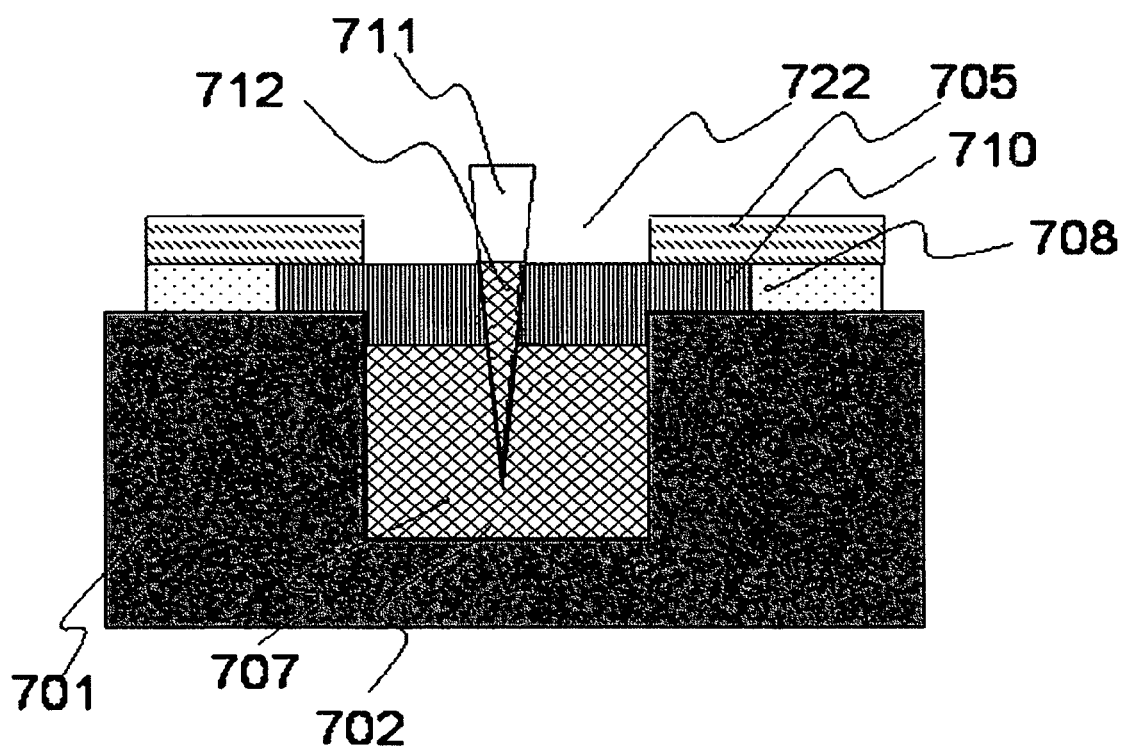
FIG. 27 is a cross-sectional view schematically showing a method of introducing a sample into a chip according to an embodiment.

FIGS. 20 to 27 are views showing a structure of a chip according to this embodiment. FIG. 20 is a top view of the chip, FIGS. 21 and 22 are top views of components of the chip. And, FIGS. 23 to 26 are cross-sectional views for illustrating a using procedure of using the chip. FIG. 27 is a cross-sectional view schematically showing a method of introducing the sample into the chip.

In the chip of this embodiment, as a basic structure of a substrate 701, the structure of the substrate used for the chip of the above-described embodiments may be used. For example, the structure of the substrate 701 may be as same as that of the substrates 103, 201 and 301. In FIG. 21, the substrate 701 is provided with a channel 703 and reservoirs 702. In this embodiment, a liquid having a smaller gravity than a liquid in the channel 703 is used as a lid. And, a seal 704 and a plate-like lid 705 are used so as to surely provide the liquid lid on the substrate 701. Each of the seal 704 and the plate-like lid 705 is provided with holes 722 (FIG. 22) having similar size and shape on a position corresponding to the reservoirs 702 of the substrate 701. A spacer 708 which is a double adhesive type is bonded to an entire circumference of a surface on the substrate 701 side of the plate-like lid 705.

Figure 23:
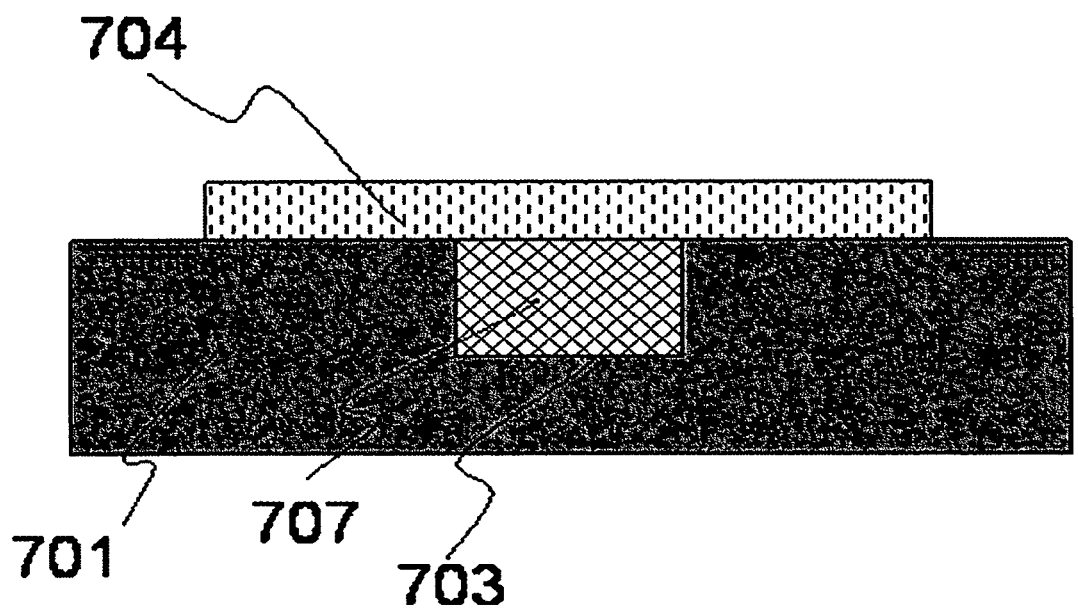
FIG. 23 is a cross-sectional view showing a procedure of using a chip according to an embodiment.
Figure 24:
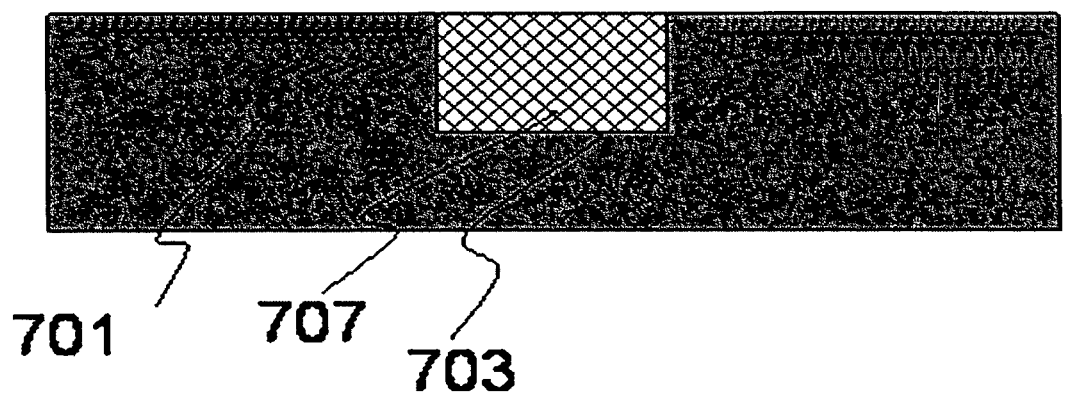
FIG. 24 is a cross-sectional view showing a procedure of using a chip according to an embodiment.
Figure 25:
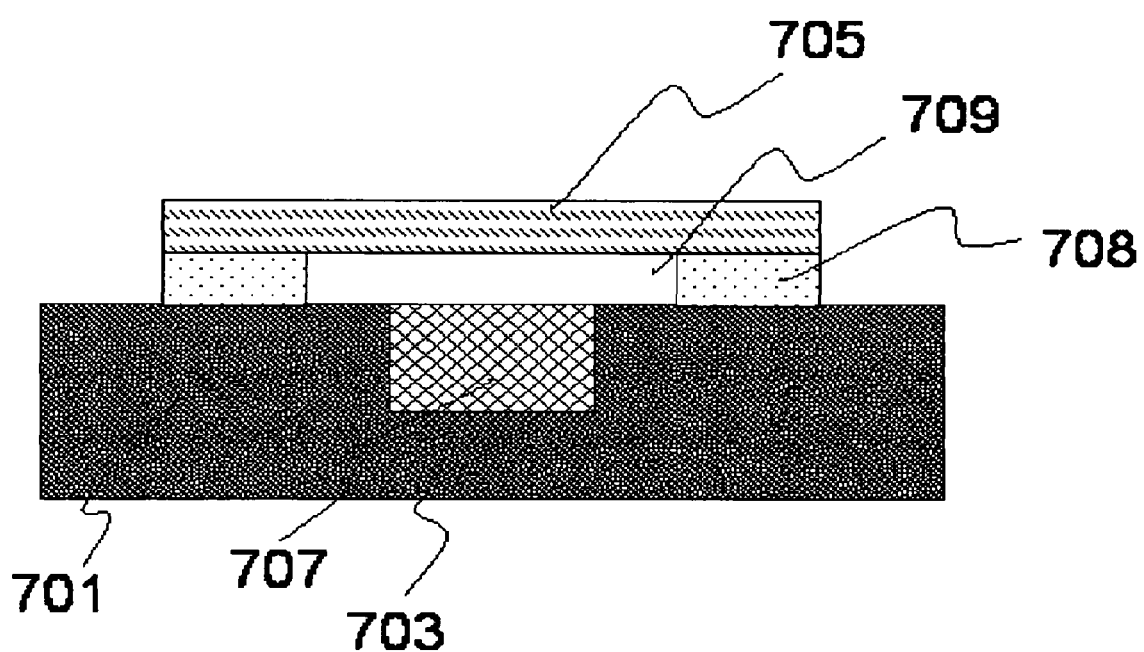
FIG. 25 is a cross-sectional view showing a procedure of using a chip according to an embodiment.

A method of using the chip of this embodiment will be described with reference to FIGS. 20 and 23 to 26. First, the seal 704 is adhered to the substrate 701 to obtain a state shown in FIG. 20. And, the migration buffer is introduced from the reservoirs 702 to fill the channel 703 (FIG. 23). Next, the migration buffer 707 is frozen and the seal 704 is detached (FIG. 24). Then, the plate-like lid 705 to which the spacer 708 is adhered is adhered to the substrate 701 to obtain a state shown in FIG. 25. In this step, the channel 703 is filled with the migration buffer 707, but there is a space 709 between the migration buffer 707 and the lid. Next, oil 710 is overlaid on the migration buffer 707 so as to fill the space 709 (FIG. 26).

An antifreeze material at a temperature of approximately 0° C. and an insulating material may be appropriately used as usage of the oil 710. For example, a material, a coagulation point of which is not lower than −100° C. and not higher than −20° C. may be used as the oil 710. Thereby, it becomes possible to obtain a state in which only the liquid in the channel 703 is frozen without freezing the oil 710. Therefore, it becomes possible to surely cover an upper portion of the channel 703 with the oil 710 in a state in which the sample in the channel 703 is frozen.

By the above-described process, a preparation for introducing the sample and the platinum electrode is completed. In this embodiment, the sample is described as a sample or a biological sample. After solving the migration buffer 707, the sample is introduced from the reservoirs 702. As shown in FIG. 27, the sample 712 is charged by inserting a pipette 711 from a hole 722 provided on the plate-like lid 705 to one of the reservoirs 702. At this moment, the sample 712 is directly injected to the migration buffer 707 by penetrating a layer of the overlaid oil 710. Next, the platinum electrodes are inserted to the reservoirs 702 to separate the components of the sample by the electrophoresis. After the electrophoresis, the electrodes are taken off, and if required, the migration buffer 707 in the channel is frozen or the like so as to prevent the separation pattern from roiling, and then the spacer 708 and the plate-like lid 705 are removed to open the channel 703. Unnecessary oil 710, which has been used as the lid, may be removed by being blown by nitrogen gas or the like.

According to this structure, the chip capable of covering the channel of the chip without making a space, and easily opening the channel without contaminating the sample or the components of the sample in the channel of the chip may be obtained.

Ninth Embodiment

This embodiment relates to a chip structured so as to preventing the sample in the channel from leaking and being contaminated when taking off the lid from the substrate. FIGS. 28 to 31 are cross-sectional views showing a structure of the chip according to this embodiment. Hereinafter, a procedure of using the chip of this embodiment will be described with reference to these drawings.

Figure 28:
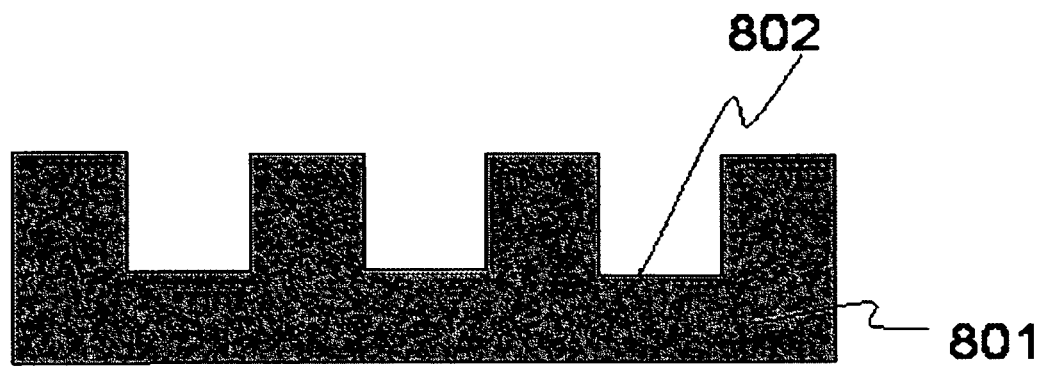
FIG. 28 is a cross-sectional view showing a procedure of using a chip according to an embodiment.
Figure 29:
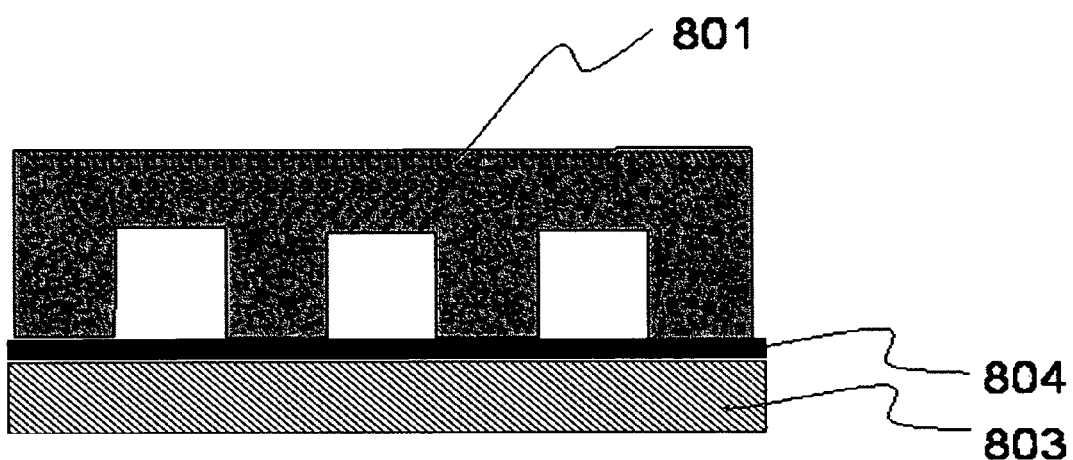
FIG. 29 is a cross-sectional view showing a procedure of using a chip according to an embodiment.

In the chip of this embodiment, as a basic structure of a substrate 801, the structure of the substrate used for the chip of the above-described embodiments may be used, for example. For example, the structure of the substrate 801 may be as same as that of the substrates 103, 201 and 301. In FIG. 28, a channel 802 and a reservoir (not shown) are provided on the substrate 801. And, as a basic structure of a lid 806, the lids described in all above-described embodiments may be applied.

Figure 30:
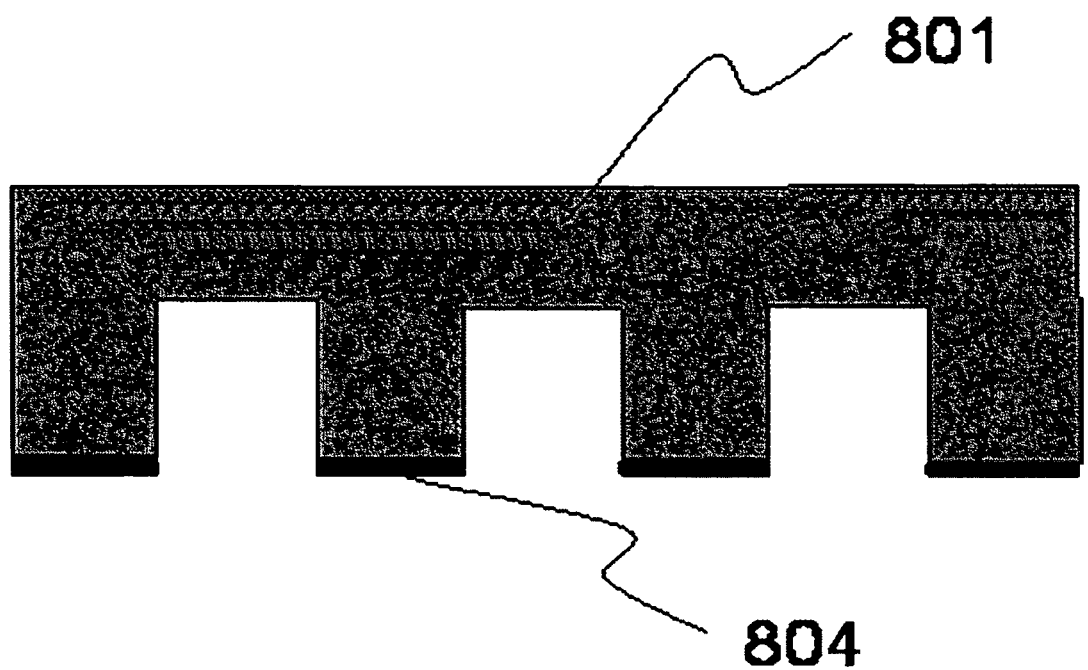
FIG. 30 is a cross-sectional view showing a procedure of using a chip according to an embodiment.

The chip of this embodiment is used as follows. Hydrophobic ink 804 is applied to a ink pad 803 and dried. As the ink pad 803, resin such as PDMS and PMMA may be used, for example, but a material is not limited to this. As the hydrophobic ink 804, oil and a hydrophobic self-assembled monolayer are applicable, but other hydrophobic or water-repellent material may also be used. The self-assembled monolayer is preferably used as the hydrophobic ink 804 from a point in which this forms a chemical bond with the substrate 801 and is not spattered to a channel portion. As a method of applying the hydrophobic ink 804, there is a spin coat method. Next, the substrate 801 is brought into contact with the ink pad 803, to which the hydrophobic ink 804 is applied, with a channel 802 side down (FIG. 29), then the substrate 801 is taken off from the ink pad 803. The substrate 801 in this stage is in a state in which the hydrophobic ink 804 is printed on only an upper surface of the chip except the channel 802 (FIG. 30).

Figure 31:
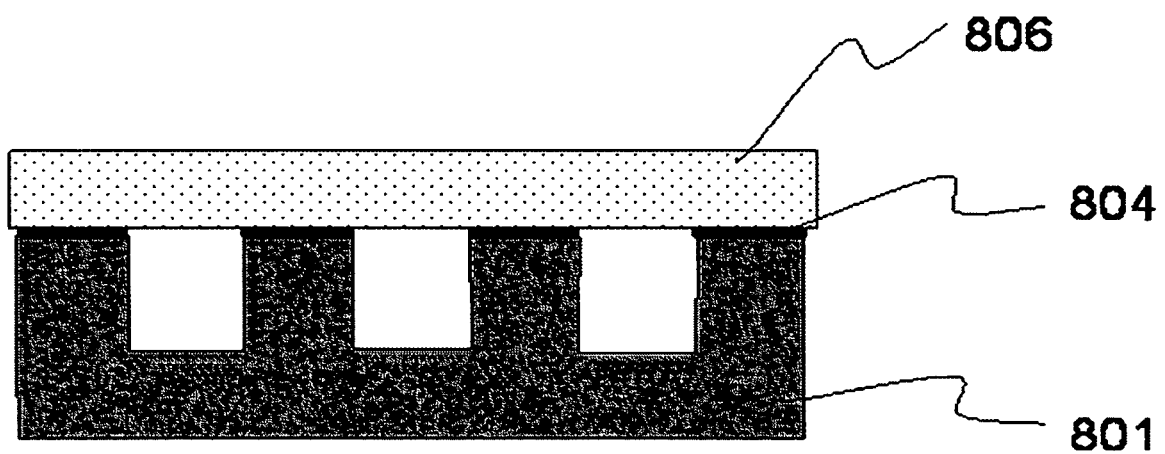
FIG. 31 is a cross-sectional view showing a procedure of using a chip according to an embodiment.

FIG. 31 is a view showing a state in which the substrate 801 to which the hydrophobic ink 804 is applied is covered with the lid 806, such that the electrophoresis may be performed. The electrophoresis of the sample is performed in the channel 802 by using the method in the first embodiment or the like. After that, the lid 806 may be removed from the substrate 801. According to this structure, the chip capable of covering the channel of the chip, and easily opening the same while preventing the solution or the components of the sample in the channel of the chip from being contaminated may be provided.

Tenth Embodiment

Figure 32:
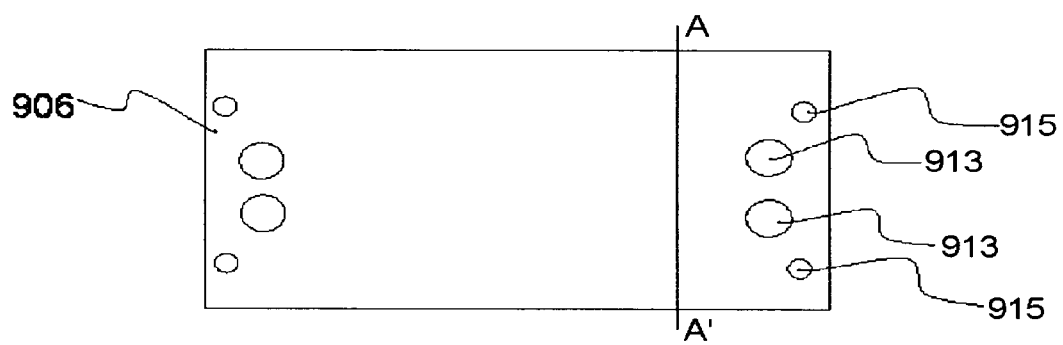
FIG. 32 is a top view showing components of a chip according to an embodiment.
Figure 33:
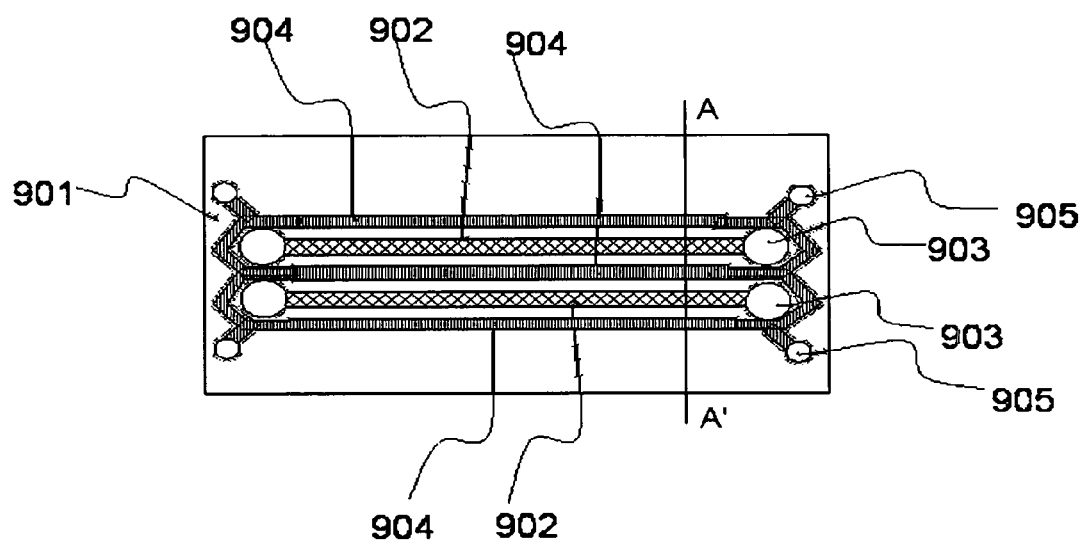
FIG. 33 is a top view showing components of a chip according to an embodiment.
Figure 34:
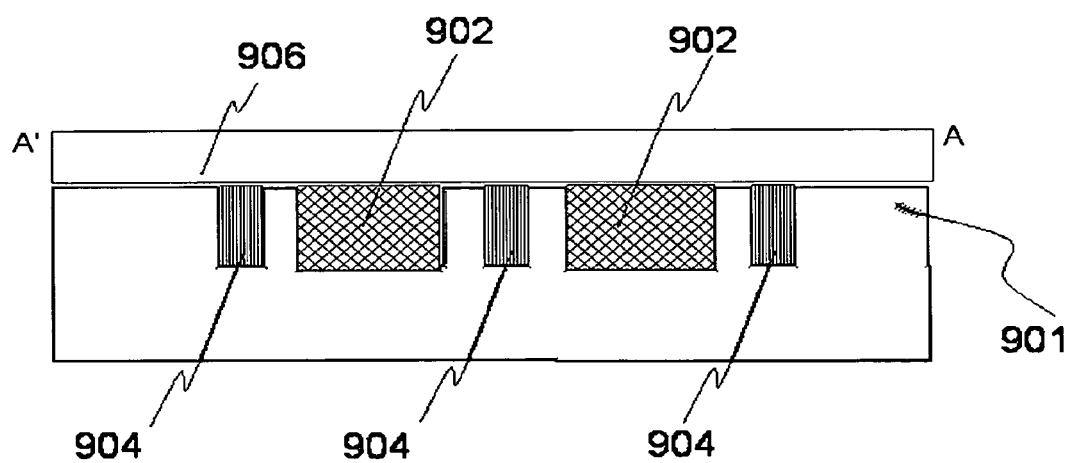
FIG. 34 is a cross-sectional view showing a structure of a chip according to an embodiment.

This embodiment relates to another aspect of the chip structured so as to prevent the sample in the channel from leaking or being contaminated, when the lid is taken off from the substrate. FIGS. 32 and 33 are top views showing components of the chip of this embodiment. And FIG. 34 is a view showing a state in which the chip of this embodiment is assembled. And FIG. 34 is a cross-sectional view taken along line A-A' in FIGS. 32 and 33.

In the chip of this embodiment, as a basic structure of a substrate 901, the structure of the substrate used in the chip of the above-described embodiment may be used. For example, the structure of the substrate 901 may be as same as that of the substrates 103, 201 and 301. And as shown in FIG. 33, two channels 902 may be formed so as to make a stripe pattern on the substrate 901 as shown in FIG. 33. The channels 902 communicate with reservoirs 903. The substrate 901 is further provided with a channel for oil 904 and reservoirs 905 for the same. A shape of the channel for oil 904 is not limited as long as this is designed so as to enclose the channels and reservoirs for the migration buffer and the sample.

All lids described in the first and second embodiments may be applied as the lid 906. As shown in FIG. 32, the lid 906 is provided with holes 913 and 915 on portions corresponding to the reservoirs 903 and 905, respectively.

The chip of this embodiment is used as follows. That is to say, the substrate 901 is covered with the lid 906. Next, the oil is introduced into the reservoirs for oil 905 to fill the channels for oil 904. The oil prevents the migration buffer or the like from leaking over the surface of the substrate.

Next, a state in which the migration buffer or the sample is introduced into the reservoirs for sample to enable the electrophoresis is shown in FIG. 34. Hereinafter, the electrophoresis is performed in the same way as in the above-described embodiments. After that, the fixing device is adjusted in a state in which the sample in the channel 902 is frozen, and the lid 906 is removed. The oil attached to the substrate 901 may be removed by introducing gas such as air and inactive gas into the channel for oil 904. Meanwhile, the antifreeze material at a temperature of approximately 0° C. and the insulating material may be used as usage of the oil. For example, the coagulation point of the oil may be not lower than −100° C. and not higher than −20° C. By thus setting, the lid 906 may be removed in a state in which only the liquid in the channel 902 is frozen.

According to this structure, the chip capable of covering the channel of the chip and of opening the same while preventing the solution or the components of the sample in the channel of the chip from being contaminated may be provided.

Eleventh Embodiment

A gas introducing path may be provided on the substrate of the chip described in the above embodiment. The gas-introducing path may be a channel for introducing air formed on the surface of the substrate. And, a groove for introducing air may be formed on the lid, when the lid is not liquid. Hereinafter, the structure of the chip of the tenth embodiment will be described as an example. In this case, the channel for oil 904 (FIG. 33) may be set to the channel for introducing air.

In this embodiment, at first, the channel for oil 904 is kept empty, and after finishing a process using the channel, the air is introduced thereinto. By doing so, it becomes possible to easily remove the lid 906 by introducing the gas into the channel for oil 904, to be used as a groove for introducing air, in use or after use of the chip. At this moment, for example, a pressure-proof tube for introducing gas introduced from a pump may be provided on an oil inlet portion of the channel for oil 904. The gas to be introduced into the channel for oil 904 may be, for example, air. And this may be nitrogen or the inactive gas such as helium.

According to this structure, the chip capable of covering the channel formed on the surface of the substrate and easily opening the same may be provided. For example, in the chip described in the above embodiment, when the substrate is formed by silicon and the plate-like lid is formed by glass, detachment of the plate-like lid might be difficult by the existence of water existing on an interface when removing the plate-like lid from the surface of the substrate. In such a case also, it becomes possible to easily detach the plate-like lid by introducing the gas from the groove for introducing air.

Twelfth Embodiment

In the chip 112 described in the first embodiment, if the resin layer 102 of the lid 113 is enough hydrophobic to inhibit leakage of the sample in the channel, and if adhesion of the lid 113 is strong, a fixing device for preventing the sample from leaking from the channel is not required to be used.

Figure 41:
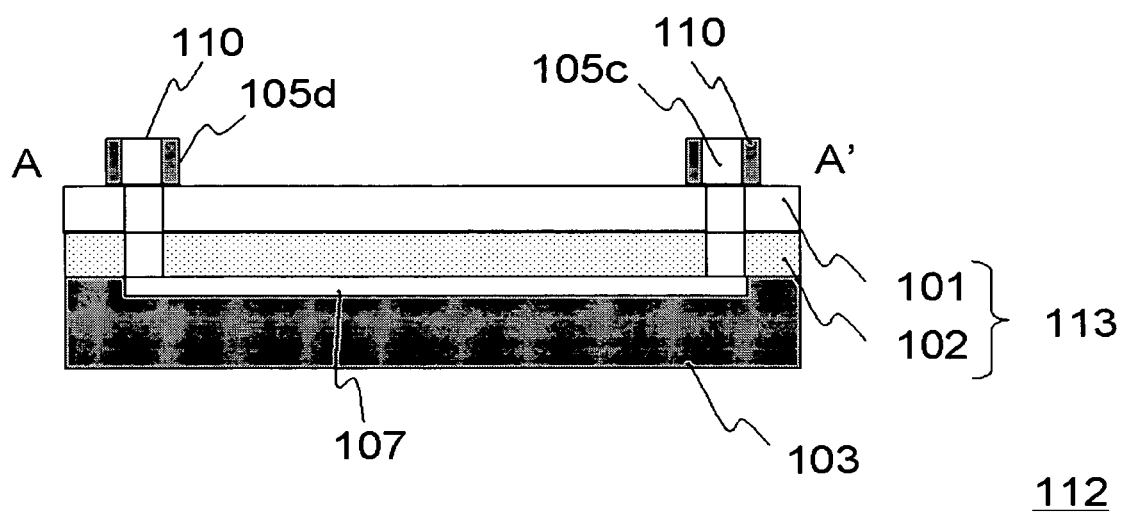
FIG. 41 is a cross-sectional view showing a structure of a chip according to an embodiment.

FIG. 41 is a view showing a state in which the chip 112 of this embodiment is assembled. FIG. 41 is a view seen from the same direction as a cross-section surface A-A' in FIGS. 1 to 3. In this embodiment also, the basic structures of the substrate 103, the resin layer 102 and the plate-like lid 101, which are components of the chip 112 may be set to the basic structures (FIGS. 1 to 3) described in the first embodiment. However, in FIG. 41, it is structured such that the tube 110 is disposed so as to protrude from the plate-like lid 101, and the reservoirs 105*d* and 105*c* are disposed above the upper surface of the plate-like lid 101. FIG. 48 is a view showing a device in which the chip of this embodiment is used. FIG. 49 is a view showing a device in which the chip of this embodiment is used.

As shown in FIG. 41, the chip 112 includes the substrate 103 and the lid 113. The lid 113 includes the resin layer 102 and the plate-like lid 101, and they may be joined to each other by heat-sealing or by an adhesive component. Sizes of the plate-like lid 101, the resin layer 102, and the substrate 103 are set approximately equal.

Although a structure of the channel may be appropriately selected, it is structured for example, only a linear channel 107*b* is formed, and the reservoirs 105*c* and 105*d* are formed on both ends of the channel on the substrate 103 shown in FIG. 3. Herein, the channel 107*b* corresponds to the above-described channel. Herein, the channel 107*b* is set to the channel for introducing and separating. In this structure also, as described with reference to FIGS. 1 and 2, the plate-like 101 and the resin layer 102 are provided with holes 115*c* and 115*d* each having a size approximately equal to that of the reservoirs 105*c* and 105*d*, respectively, provided on the substrate 103, on portions corresponding to the reservoirs 105*c* and 105*d*. A liquid to be used for the migration may be introduced into the channel 107*b* on the substrate 103 through the holes 115*c* and 115*d*. And, the electrodes for electrophoresis are placed through the holes 115*c* and 115*d*.

Meanwhile, the tube 110 having the same size as or slightly larger than inner diameters of the holes 115*c* and 115*d* may be disposed on the hole 115*c* such that the holes communicate with each other. The size of the tube 110 is appropriately selected according to a shape or a size of the hole 115*c* or 115*d*. By providing the tube 110, it becomes possible to easily adjust depths of the holes 115*c* and 115*d* by adjusting the length of the tube 110 to make the holes enough deep. Therefore, it becomes possible to prevent the liquid in the holes 115*c* and 115*d* from drying when performing the electrophoresis, thereby surely applying a voltage between the electrodes.

Figure 35:
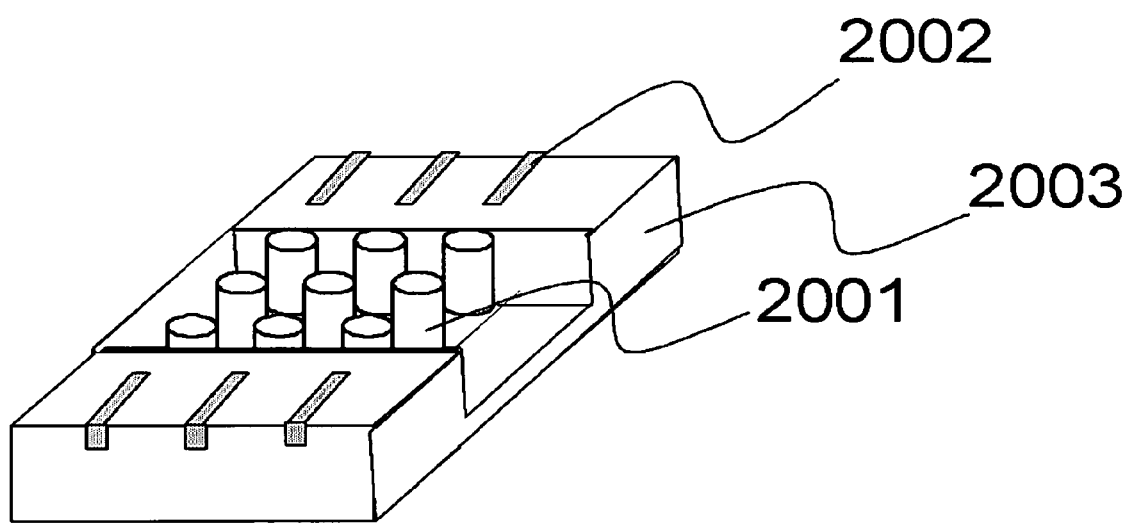
FIG. 35 is a perspective view showing a structure of a channel of a chip according to an embodiment.

In the chip 112, a convex structure supporting the lid 113 may be provided in the channel 107*b*. FIG. 35 is a perspective view showing a structure of the channel having the convex structure. In FIG. 35, a substrate 2003, which correspond to the substrate 103, is provided with a concave portion, which corresponds to the channel 107*b*, and a bottom surface of the concave portion is provided with a convex structure 2001. Meanwhile, a groove-like structure 2002 shown in FIG. 35 will be described later.

The convex structure 2001 is composed of a plurality of cylinder-shaped projections. The convex structure 2001 has an effect of preventing the channel 107*b* from being crushed by deflection of the lid 113, and an effect of keeping the sample in the channel 107*b* when removing the lid 113 and in an experimental procedure that follows.

Meanwhile, in the chip 112 of this embodiment, one or more convex structure 2001 may be formed at intervals of not larger than 80 μm in a width direction of the channel, and one or more convex structure 2001 may be formed at intervals of not larger than 80 μm in a longitudinal direction of the channel, and an upper surface of the convex structure 2001 may contact with the lid 113. Thereby, it becomes possible to surely prevent the channel 107*b* from being crushed by the deflection of the lid 113.

Meanwhile, in the chip 112, the convex structures 2001 may especially be formed such that distance between centers thereof is not larger than 20 μm. Thereby, it becomes possible to prevent the channel 107*b* from being crushed by the deflection of the lid 113. And, it becomes possible to increase a contact area, consequently friction resistance between the sample in the channel 107*b* and the convex structures 2001. Therefore, it becomes possible to keep the sample in the channel 107*b* when removing the lid 113 and in the experimental procedure that follows. First, a problem that the frozen sample is removed by attaching to a resin layer 102 side, when detaching the lid 113, is solved. And, an effect of keeping the components of the dried sample is increased. Meanwhile, although a lower limit of the distance between centers of the convex structure is not specifically limited, for example, this may be set not smaller than 1 μm.

The chip of this embodiment may be a chip in which the convex structure 2001 is such that a sum in an entire circumference of an projected area thereof to a surface perpendicular to the upper surface of the channel 107b is not less than a half of a surface area that the lid 113 contacts the sample in the channel 107b. Thereby, it becomes possible to more surely prevent the channel 107b from being crushed by the deflection of the lid 113. And, it becomes possible to increase the contact area, consequently the friction resistance between the sample in the channel 107b and the convex structure 2001. Therefore, it becomes possible to keep the sample in the channel 107b when removing the lid 113 and in the experimental procedure that follows. First, a problem that the frozen sample is removed by attaching to a resin layer 102 side, when detaching the lid 113 is solved. And, an effect of keeping the components of the dried sample is increased.

The chip of this embodiment may be the chip in which an area of an upper surface of the convex structure 2001 is larger than 0.06% of the area of the upper surface of the channel 107b. Thereby, it becomes possible to more surely prevent the channel 107b from being crushed by the deflection of the lid 113, when the convex structure 2001 is in a columnar structure which has a simple fabrication process. And, it is possible to increase the contact area, consequently the friction resistance between the sample in the channel 107b and the convex structure 2001. And, it becomes possible to keep the sample in the channel 107b when removing the lid 113 and in the experimental procedure that follows. First, a problem that the frozen sample is removed by attaching to a resin layer 102 side, when detaching the lid 113 is solved. And, an effect of keeping the components of the dried sample is increased.

The inventors of the present invention confirm from experiment that each of the channels of this embodiment has the described effect by forming the above-described convex structure.

The chip of this embodiment may be a chip in which a side surface of the channel 107b has a concave structure. For example, this may be structured such that a concave portion in a predetermined shape is formed on the side surface of the channel 107b. Thereby, it becomes possible to keep the sample in the channel 107b when removing the lid 113 and in the experimental procedure that follows.

Meanwhile, the inventors of the present invention confirm that there is an effect of keeping the sample in the channel 107b by forming the above-described side surface of the channel 107b in a concave structure.

The chip of this embodiment may have a property that the lid 113 loses a contact state of the same to the lid 103. By doing so, it becomes possible to easily remove the lid 113 by cooling the lid 113 when removing the lid 113 from the substrate 103. Further, by doing so, the contamination to the sample in the channels 107b and 107d may be inhibited. And when the sample in the channel 107b is frozen by the cooling, it becomes possible to fix the sample in a state in which the components of the sample are separated. Therefore, it is possible to easily remove the lid 113 while preventing the sample in the channel 107b from being contaminated.

Referring to FIGS. 3 and 35, in a case in which quartz is used as a material of the substrate 103, the channel 107b is fabricated by dry etching. By performing layout of a pattern for forming the convex structure 2001 in the channel 107b, in a mask herein used, it becomes possible to simultaneously form the convex structure 2001.

And, minute irregularity may be formed on a wall surface and bottom surface of the channel 107b, or on a surface of the convex structure 2001. By the minute irregularity, a surface area of the channel 107b side becomes larger than that of the lid 113 side, thereby the sample may be kept in the channel 107b. The minute irregularity may be formed by porous alumina. For example, in a case in which the substrate 103 is formed by quartz, after aluminum is vacuum-deposited on the surface of the substrate 103, this is oxidized to porous alumina by an anodic oxidation method to form the minute irregularity.

And, the surface of the convex structure 2001 in the channel 107b and the wall surface of the channel 107b may be hydrophilic. As a method of realizing the hydrophilic surface, a plasma ashing process may be performed to an entire substrate 103. And, a hydrophilic resin such as acrylamide or the like, a light curable hydroxyethyl methacrylate (HEMA), a silicone or an acrylic resin including and titanium oxide being photocatalysis, or the like may be coated on the surface of the substrate 103 or the channel 107b. Herein, it is preferable that the surface of the substrate 103 is modified to hydrophilic before a coating. The surface having the above-described hydrophilicity has a good wettability and is firmly fixed to the solution strongly frozen by an anchor effect, thereby more surely keeping the sample in the channel 107b.

Meanwhile, although a case in which a cylindrical body composing the convex structure 2001 is cylinder-shape is shown in FIG. 35 by an example, the convex structure 2001 may be a circular truncated cone shape, a doughnut shape, and a rectangular column shape such as a square pole, for example, as long as the convex structure 2001 has a shape so as to support the lid 113. And, although a structure in which the convex structure 2001 has a plurality of columnar bodies is shown in FIG. 35 as an example, the number of the columnar bodies is not specifically limited; this may be singular or plural.

The convex structure 2001 may have a structure such that the area of the upper surface of the convex structure 2001 is larger than the area of the bottom surface of the convex structure 2001. The structure in which the area of the upper surface of the convex structure 2001 is larger than the area of the bottom surface of the convex structure 2001 includes an inverted tapered shape or a hammerhead shape. By doing so, the sample may be kept in the channel 107b when removing the lid 113 and in the experimental process that follows. The inventors of the present invention have been confirmed that it is possible to open the channel 107b while surely keeping the frozen sample in the channel 107b by the convex structure 2001 (FIG. 35).

Figure 36:
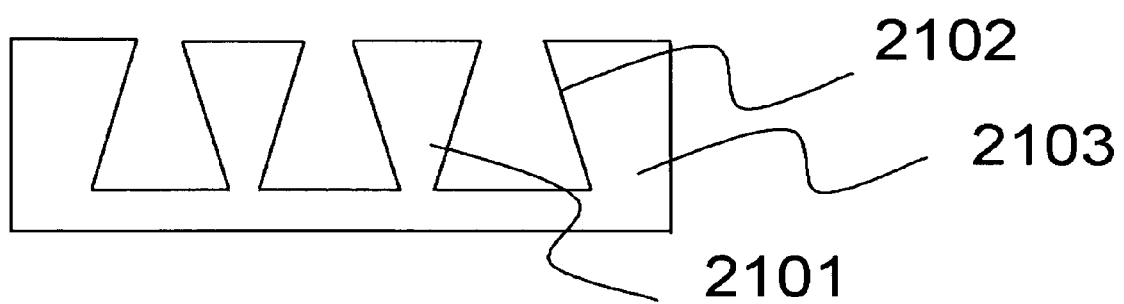
FIG. 36 is a cross-sectional view showing a structure of a channel of a chip according to an embodiment.
Figure 37:
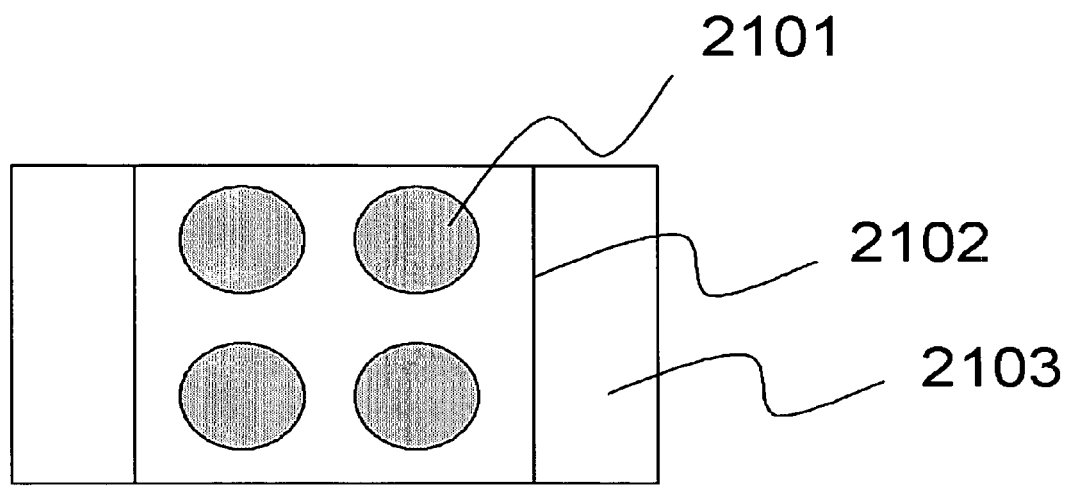
FIG. 37 is a plain view showing a structure of a channel of a chip according to an embodiment.

FIG. 36 is a cross-sectional view showing another example of the structure in the channel of the chip of this embodiment. And, FIG. 37 is a plan view showing the channel structure having a structure shown in FIG. 36. In FIGS. 36 and 37, a state in which a concave portion corresponding to the channel 107b is formed on the substrate 2103 corresponding to the substrate 103, and the convex structure 2102 is provided in the concave portion, is shown. As shown in FIG. 36, the wall surface 2101 or the convex structure 2102 of the channel 107b may be an inverted mesa structure or a concave structure or a large irregular structure.

By fabricating the wall surface 2101 or the convex structure 2102 in any of the above-described structures, the contact area and the friction resistance between the sample and the wall surface 2101 may be increased. After reviewing by the inventors using the chip having the structure shown in FIGS. 1 to 3, 42, 36 and 37, it has been confirmed that the sample may be kept in the channel 107b by fabricating the wall surface 2101 or the convex structure 2102 in any of the above-described structures. Meanwhile, the structure shown in FIGS. 36 and 37 may be realized by controlling side etching by selecting an appropriate gas mixture ratio, when performing dry etching by using a metal mask.

FIG. 35 is described again. Another groove-like structure 2002 for an air vent hole may be provided on a region other than a forming region of the concave portion, being the channel 107b on the surface of the substrate 2003. The groove-like structure 2002 extends to an end of the substrate 2003 in a region other than the channel 107b, so that air freely enters and exits. When placing the lid 113 to the substrate 2003, air enters between them, thereby a bubble tends to remain therebetween. However, by providing the groove-like structure 2002, it becomes possible to completely eliminate the bubble.

In this embodiment, although materials capable of being microfabricated easily, such as quartz, glass and silicon, for example, are preferably used as the material of the substrate 103. However resin material, for example, PDMS or PMMA may also be used.

And, as the material of the plate-like lid 101, there are the materials exemplified in the first embodiment.

And, as the material of the resin layer 102, there are materials exemplified in the first embodiment. In this embodiment also, materials allowing some elastic deformation is preferably used as the resin layer 102. By using the material having elastic deformation, it becomes possible to surely adhere the same to the surface of the substrate 103. And the resin layer 102 may have adhesion, allowing the same to surely adhere to the surface of the substrate 103. Especially, the silicone resin such as PDMS having self-adhesion is preferable.

Especially, it is preferable that the material includes the temperature range of not lower than −20° C. and not higher than 30° C. within an operating temperature range in which the deterioration of adhesion of the sheet is within 20% of the maximum value of the adhesion in the temperature range not lower than −20° C. and not higher than 30° C. Since the experiment is performed under the above described temperature at a stage in which the lid 113 is required, this sufficiently serves as the lid. And at a stage in which the lid 113 is not required, by cooling the chip 112 down to not higher than the above-described temperature range, the resin layer 102 is hardened, and the lid 113 may be detached easily without adhesive deposit.

For example, a seal 9795 (manufactured by 3M), which uses a silicone-based resin as an adhesive, includes a range from −30° C. to 30° C. in a temperature range in which the deterioration of adhesion is not more than 20%. Therefore, the seal becomes hardened at a temperature of −150° C. and is naturally separated from the substrate. Therefore, it becomes possible to easily separate the seal 9795 without adhesive deposit.

And, a seal 5564A (manufactured by 3M), which uses an acrylic resin as an adhesive, includes a temperature range from −20° C. to 30° C. in a temperature range in which the deterioration of the adhesion is not more than 20%. Therefore, the seal becomes hardened at a temperature of −100° C. and is naturally separated from the substrate. Therefore, it becomes possible to easily separate the seal 5564A without adhesive deposit.

And, the resin layer 102 may be provided with adhesion and may be separated by being hardened by UV-irradiation. Before UV-irradiating, the resin layer 102 may serve as the lid by the adhesion thereof. And, in a stage in which the lid 113 is not required, UV having an appropriate wavelength is irradiated as required, thereby hardening the resin layer 102, and the lid 113 is easily separated without adhesive deposit.

And, the plate-like lid 101 and the resin layer 102 may be joined to each other. And, only the plate-like lid 101 or the resin layer 102 may be used. And, as the resin layer 102, water-repellent or oil-repellent material such as fluorinated resin, including PTFE or the like, is preferably used. And, main portion of the resin layer 102 may be formed by another material, and the water-repellent or oil repellent process by PTFE or the like may be performed on the surface thereof.

A fabrication of the chip 112 may be performed by using a method, for example, described in the first embodiment. A groove is formed on the substrate 103 to make the channel 107b. The lid 113 is adhered to the substrate 103. And, the reservoirs 105c and 105d communicating with the channel 107b are formed. The formation thereof may be performed by a method suitable for kinds of materials of the substrate 103, such as press molding using a metal mold such as etching and embossing, injection molding, forming by light curing, when using plastic material as the substrate 103. A width of the channel 107b is appropriately set according to operations performed to the sample in the channel. For example, when performing fraction of high-molecular components (DNA, RNA, protein, sugar chain), the width may be set from 5 µm to 10 µm. And when joining the lid 101 to the resin layer 102, the junction may be performed by bonding using adhesive or by heat sealing. The holes 115c and 115d are formed on the obtained lid 113.

The handling of the chip 112 may be improved by disposing the chip 112 in the sealed vessel 4007, which is described above with reference to FIGS. 48 and 19. A sample-fixing device 4000 is disposed in the sealed vessel 4007, which may fix the sample in the channel 107b. For example, the sample-fixing device 4000 may be provided with the temperature controlling mechanism or cooling mechanism 4030. Thereby, it becomes possible to fix the sample in the channel 107b by freezing. And, the sample-fixing device 4000 may fix the sample in the channel 107b in a shorter time and by a smaller power because this contacts with the chip 112.

And, the sealed vessel 4007 is provided with the valve for vacuuming 4005, and the valve for vacuuming 4005 may be connected to the vacuum pump 4006 by means of metal or resin tube. Thereby, the sealed vessel 4007 may be vacuumed. And, the sealed vessel 4007 has a connector to extend a conductor communicating with the electrode of the chip 112 to outside of the sealed vessel 4007. A voltage is applied from the external power supply 4001 to the electrode through the connector.

And, a measurement mechanism 4004, which monitors a separating state of the components of the sample, may be provided on outer or inner side of the sealed vessel 4007. A detecting method of a measurement mechanism 4004 may be optical one. An optical detection may be performed, for example, by combining the components of the sample with a fluorescent material in advance, irradiating the same with a laser along the channel 107b, and observing the fluorescence emitted from the components of the sample. At this time, the measurement may be performed by using a fluorescent measurement system obtained by combining an X-Y automatic stage, a fluorescence microscope, and a photo multiplier. The X-Y automatic stage is used as a board of the fluorescence microscope. The chip is placed on a stage of the X-Y automatic stage, and an exciting light is irradiated to the channel 107b through an optical system of the fluorescence microscope. When performing the fluorescent measurement of the channel 107b, a photon counting is performed by the photo multiplier through the optical system of the fluorescence microscope, being the measurement mechanism 4004. And, the sealed vessel 4007 may be provided with an opening mechanism 4002 shown in FIG. 49 used for removing the lid 113 from the substrate 103. The opening mechanism 4002 may be further provided with a robot arm 4003 for performing a operation to remove the lid 113. Meanwhile, the opening mechanism may be provided with not only the robot arm but also a pair of vacuum tweezers. By using the robot arm 4003, the lid 113 may be removed.

Next, a method of using the chip 112 and the device using the chip 112 will be described. First, in order to cover the channel 107b on the substrate 103, the lid 113 is placed on the substrate 103 while adjusting positions of the reservoirs 105c and 105d. Next, the reservoirs 105c and 105d are formed on the lid 113.

On the contrary, when opening the channel 107b, first, the chip 112 is cooled, and after freezing the sample in the channel 107b, the lid 113 may be removed. By freezing the sample, it becomes possible to fix the separated components of the sample before diffusing. When removing the lid 113 from the substrate 103, by removing the lid 113 after freezing the sample, it becomes possible to prevent the components of the sample from mixing to each other, and prevent the sample from leaking and being contaminating.

In this manner, the chip 112 of this embodiment may surely cover the channel 107b. And, for example, by forming the surface of the lid 113 by the lyophobic or liquid-repellent material, the surface of the lid 113 may be lyophobic or liquid-repellent, thereby preventing the sample from attaching to the lid 113. And, by fabricating the convex structure 2001 in the channel 107b, it becomes possible to prevent the components of the sample from diffusing, and prevent the frozen sample from attaching to the lid 113.

By providing predetermined channel and reservoir on the chip 112, it becomes possible to perform a desired operation such as separating and analyzing to the components of the sample. For example, it is possible to sequentially perform the mass spectrometry after performing the electrophoresis by using the chip 112. In this case, first, a solution for migration including the components of the sample is introduced from any of the reservoirs 105c and 105d in a state in which the channel 107b of the chip 112 is completely covered with the lid 113, to fill the channel 107b.

Although the solution for the migration is appropriately selected as usage, this may be the solution for isoelectric focusing electrophoresis. The isoelectric focusing electrophoresis is one of methods of electrophoresis for separating carrier ampholytes according to an isoelectric point (pI), which is proper to the carrier ampholytes such as protein, which is component in the sample. The point pI indicates a pH at which a positive charge and a negative charge of the components of the sample are exactly equal. The components of the sample have the electrical charge according to the pH of the solution, which the components itself solves, and perform electrophoresis to each pI area. After achieving each pI, electrophoretic mobility of the components of the sample is vanished, and the electrophoresis is finished. By this phenomenon, the components of the sample may be concentrated and separated for each pI. In the solution for isoelectric focusing electrophoresis, carrier ampholytes for forming a pH gradient is included, in addition to the components of the sample to be separated. In order to form the pH gradient in the channel 107b, the solution for isoelectric focusing electrophoresis is introduced into the channel 107b, and next, an acid solution and an alkaline solution are put into the reservoirs 105c and 105d, respectively, and a voltage is applied between the electrodes disposed in the reservoirs.

In this embodiment, the components of the sample and the solution for migration including the components are described as the sample. After introducing the sample into the channel 107b, the acid solution and the alkaline solution are put into the reservoirs 105c and 105d, respectively, and the platinum electrodes are inserted to the reservoirs 105c and 105d. A voltage may be applied between the reservoirs 105c and 105d through the platinum electrodes. First, the sample is introduced into the channel 107b in this manner, and the acid solution and the alkaline solution are put into the reservoirs 105c and 105d, respectively, with respect to the chip 112.

Next, the chip 112 may be disposed in the sealed vessel 4007 shown in FIG. 49. First, a case in which the chip 112 is disposed in the sealed vessel 4007 in FIG. 49 is described. By disposing the chip 112 in the sealed vessel 4007 in FIG. 49, the sample may be fixed by using the sample fixing mechanism 4000 in the sealed vessel 4007 when opening the channel 107b. After cooling the chip 112 and freezing the sample in the channel 107b by the cooling mechanism in the sample fixing mechanism 4000, the channel 107b is opened by removing the lid 113. After separating the components of the sample, whole sample is frozen, so that the separated components of the sample, for example, protein and DNA are prevented from being diffused. By removing the lid 113 after freezing the sample, mixing of the components in the channel including the diffusion of the components of the sample, and the contamination and leakage of the sample may be inhibited. The platinum electrodes are inserted to the reservoirs 105c and 105d of the chip 112 disposed in the sealed vessel 4007, and the sealed vessel 4007 is sealed. The platinum electrodes communicate with a power supply 4001 through conductors, and by applying a voltage between the electrodes through the power supply 4001, the components of each sample are separated according to each pI in the channel 107b. In the chip of this embodiment, a detecting unit 109 extends in an entire channel. The components of the separated sample are optically detected by the measuring mechanism 4004 in the detecting unit 109 (FIG. 5). The optical detection may be performed, for example, by combining the molecule with a fluorescent material in advance, irradiating the channel 107b corresponding to the detecting unit 109 with a laser along the channel 107b, and observing the fluorescence emitted from the molecule.

In the channel 107b, as a result that the components in each sample are separated according to each pI, the components are concentrated to a portion of the channel to be a state such as a belt of the channel width (band state). After the separation by the isoelectric focusing electrophoresis is finished and apply of the voltage is stopped, the sample is fixed by using the sample fixing device 4000 in order to prevent the components of the sample concentrated in the band state from diffusing. In a case in which the sample-fixing device 4000 is provided with the cooling mechanism, whole the chip 112 is rapidly frozen to fix the sample. The components of the sample is easily diffused in the liquid by Brownian movement or the like, however, this is not diffused in the solid, so that it is preferable to fix the sample in the channel as soon as possible after separating the components of the sample.

And, the cooling mechanism of the sample-fixing device 4000 may be a stage cooled down to an appropriately selected temperature in a range of −20° C. to −200° C. by using a freezer or liquid nitrogen, that is, a cooling stage, and the chip 112 may be placed thereon. And, this may be a Peltier cooling stage. This may be the cooling stage formed by block stage of a highly thermal conductive metal such as copper and aluminum. By cooling the block stage in the refrigerator or in the liquid nitrogen, for example, and placing the chip 112 thereon, or placing the block stage on the chip 112, the chip 112 may be effectively frozen. And, the material of the block stage to be cooled is not limited to this, and a highly workable material, such as stainless steel may be used.

And when freezing from the reservoirs 105c and 105d in which a large quantity of sample exists, the sample expands when this becomes solidified, so that this freezes while pushing out the sample in the channel. Consequently, the sample transfers and the separated components of the sample are mixed. However, the inventors of the present invention minimized the transfer of the sample by placing the chip 112 on the cooling stage having a shape without reservoir portion and freezing the same from the channel 107b portion. And at this time, the transfer of the sample may further be inhibited by making a portion in which the sample is more quickly frozen, along the channel.

Figure 38:
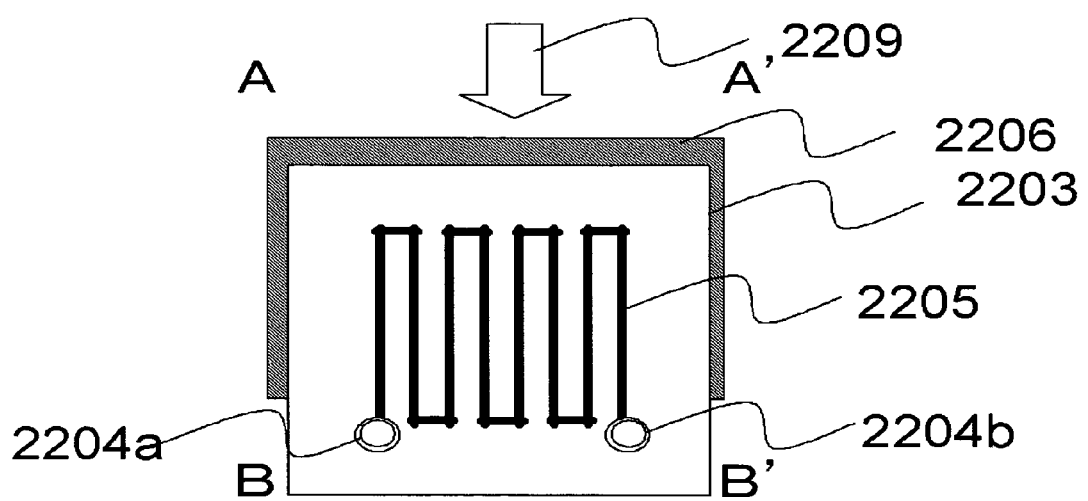
FIG. 38 is a plain view showing a structure of a substrate of a chip according to an embodiment.
Figure 39:
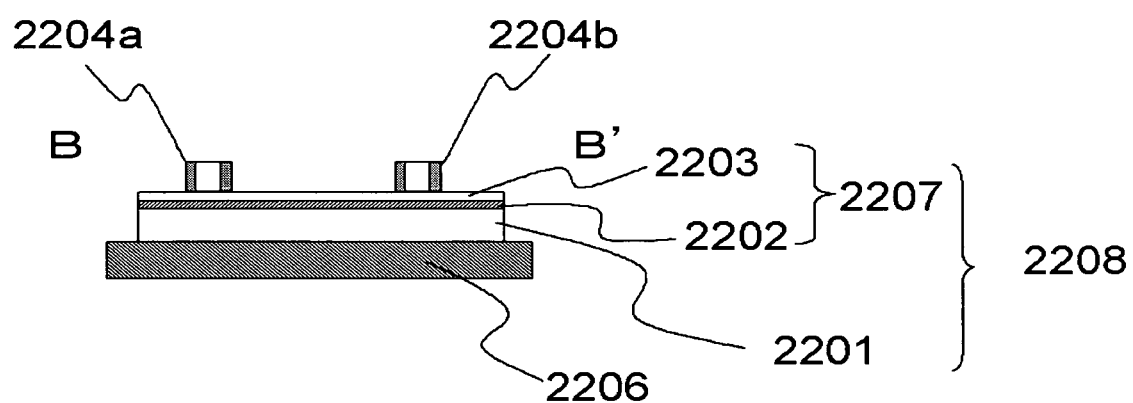
FIG. 39 is a cross-sectional view showing a structure of a chip according to an embodiment.

Although the structure in which the planer shape of the channel 107b is linear is illustrated in FIG. 3, the channel 107b may be made to have a meander structure as shown in FIG. 38. FIG. 38 is a plain view showing another structure of the substrate 103 of the chip 112. And, FIG. 39 is a cross-sectional view of a chip 2208 having the substrate 2203 shown in FIG. 38. In the chip 2208 shown in FIG. 38, a meander-shaped channel 2205 is formed on the substrate 2203 corresponding to the substrate 103. Reservoirs 2204a and 2204b are provided on both ends of the channel 2205. The reservoirs 2204a and 2204b correspond to the reservoirs 105c and 105d, respectively.

And as shown in FIG. 39, a lid 2207 corresponding to the lid 113 is structured such that a plate-like lid 2201 corresponding to the plate-like lid 101 and a resin layer 2202 corresponding to the resin layer 102 are laminated to each other.

In the chip shown in FIG. 38, the substrate 2203 is placed on a cooling stage 2206 and cooled in a direction indicated by an arrow 2209 in the drawing so as to be frozen from an A-A' side gradually to a B-B' side in the drawing.

By providing the meander-shape channel 2205, it becomes possible to solidify the sample while preventing the sample from transferring, and the band state composed by the separated components of the sample from being mixed. And, a region other than a forming region of the reservoirs 2204a and 2204b on a bottom surface of the substrate 2203 may be metal evaporated in advance. For example, by forming a deposited metal film with a sufficient film thickness, for example, a thickness not less than 100 nm by a highly thermal conductive material such as aluminum, the channel 107b cooled through the aluminum is more effectively cooled than reservoirs 2204a and 2204b portions cooled through air.

Therefore, it is possible to cool the chip 112 from the channel 2205 portion only by placing the chip 112 on the cooling stage 2206. And, by heightening the channel 2205 portion of the cooling state 2206 or by making the forming region of the reservoir 2204a of the substrate 2203 not to contact with the cooling stage 2206, so as to make a vertical interval on the surface of the cooling stage 2206, the similar effect may be realized. And, by using materials having different thermal conductivity for the cooling stage, a stage having a temperature distribution in which the channel portion is in a low temperature and the reservoir portion is in a higher temperature than the channel portion, may be realized. By using the cooling stage 2206, it is possible to cool the chip 112 from the channel portion.

In the stage shown in FIG. 41, the chip 112 is frozen and the frozen sample is held in the channel 107b. The sample in the channel 107b is in a solid state and the resin layer 102 is hardened. Next, the lid 113 is removed from the substrate 103 by using the opening mechanism 4002 and the robot arm 4003 in FIG. 49, thereby opening the channel 107b. At this time, in a case in which an adhesive having high adhesion is used as the resin layer 102, for example, when the lid 113 is removed at a room temperature, there is a problem that a part of the resin layer 102 remains on the substrate 103 side. The remained part may cause a contamination of the channel 107b. However, if the resin layer 102 is hardened by cooling the chip 112 down to a temperature not higher than an operating temperature range, in which the adhesion is within 20% of the maximum value thereof in a temperature range from −20° C. to 30° C., before removing the lid 113, the lid 113 may be removed without adhesive deposit generated by difficulty in detachability. In this stage, the chip 112 is cooled, and the frozen sample is held in the channel 107b from which the lid 113 is removed.

Continuously, the mass spectrometry is performed to the components of the sample after the migration. It is preferable that the sample is dried, because the handling may be difficult with the substrate 103 frozen. For example, if the frozen sample is taken off from the cooling stage, this melts easily with an increase of a temperature and the components of the sample are diffused. Therefore, it is required a method in which the sample is dried while keeping the components in the sample separated. In many cases, if only the components in the sample are heated, a portion in which the frozen sample is melt and a portion in which the same are evaporated are generated. On the substrate 103 in such a condition, the separated sample is diffused, by phenomena in which the melted sample flows into the channel in which the sample is evaporated or the sample is mixed in the melted portion. In order to solve the problem, the sample may be sublimed without being melted.

In this embodiment, the sample after migration may further be freeze-dried. At this time, if the chip 112 is disposed in the sealed vessel 4007, the substrate 103 from which the lid 113 is removed is kept frozen by the temperature controlling mechanism of the fixing device 111 or the cooling mechanism of the sample-fixing device 4000, and the sealed vessel 4007 is vacuumed by the vacuuming pump 4006 by opening the valve for vacuuming 4005. Thereby, the solvent of the sample in the channel 107b may be sublimed. And thereby, it is possible to sublime the solvent of the sample in the channel 107b, keep the positional relationship of the components in the sample, and dry the same without mixing the components.

Furthermore, it is possible to perform the mass spectrometry to the sample in the channel 107b in a state in which the frozen sample or the dried sample is kept on the substrate 103. The vacuuming pump 4006 is stopped and an inside of the sealed vessel 4007 is returned back to an atmospheric state at a speed in which the sample is not diffused. After that, the substrate 103 is taken out of the sealed vessel 4007, and the mass spectrometry may be continuously performed.

Figure 40:
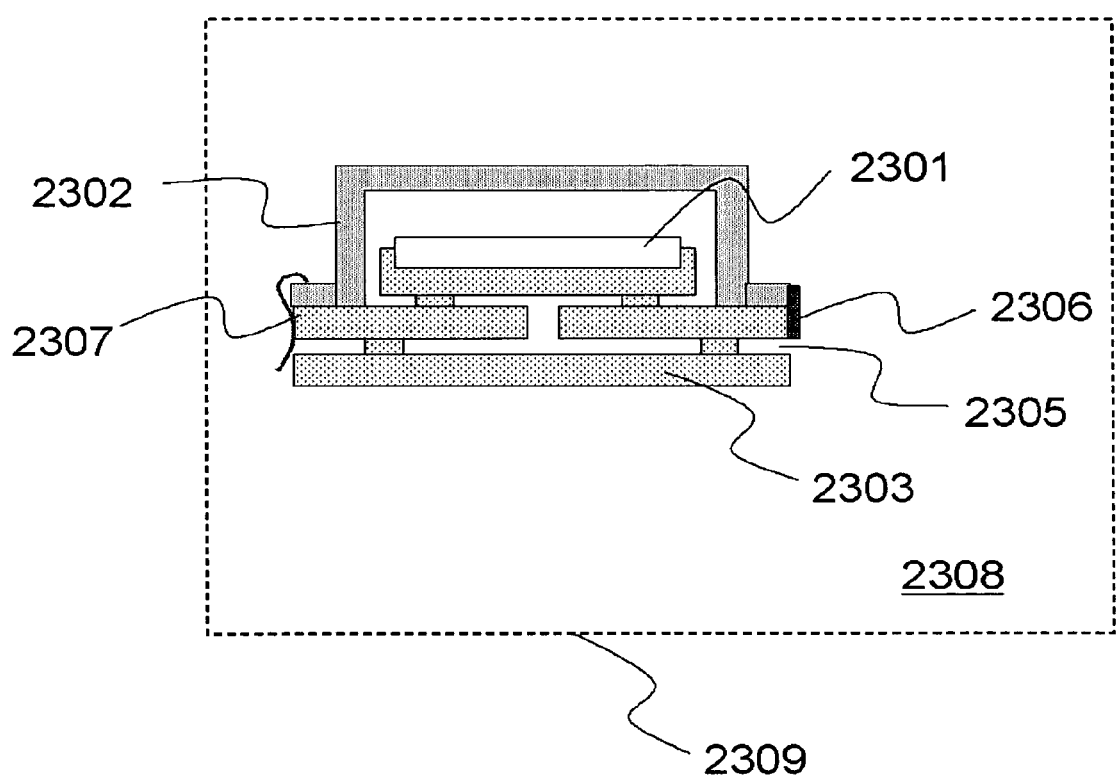
FIG. 40 is a cross-sectional view showing a structure of an attachment for freeze-drying according to an embodiment.

At this time, if the separation is performed without disposing the chip 112 in the sealed vessel 4007, it is possible to place the substrate 103, in which the sample is frozen, on an attachment for freeze-drying, and further the same is freeze-dried in a sealed case. FIG. 40 is a cross-sectional view showing a structure of the attachment. The attachment 2308 shown in FIG. 40 is composed of a lid 2302 and a board 2303, and is freely opened and closed by means of a hinge 2306. The board 2303 is provided with a gas-introducing path 2305 designed such that the substrate 2301 corresponding to the substrate 103 is not directly exposed to air.

When freeze-drying the sample in the chip 112, the substrate 2301 is placed on an attachment 2308 which is cooled in advance, and a stopper 2307 for fixing the lid 2302 in a closing state is put. And the attachment 2308 is placed in a vacuum chamber 2309 and the chamber is sealed. By cooling the attachment 2308 before freeze-drying, it becomes possible to keep the substrate 2301, having a small size and small heat capacity, in a frozen state until the vacuum chamber 2309 is enough vacuumed.

It is preferable that a material of the attachment is metal having a high heat capacity. For example, stainless steel or the like is preferably used. However, there is a case in which the lid 2302 formed by a transparent material is easy to use, and in such a case, the lid can be formed by acrylic, quartz, or the like. After placing the substrate 103 in which the sample in the channel is frozen, this may be freeze-dried in the case (vacuum chamber 2309). After freeze-drying, air is introduced in the vacuum chamber 2309. At this time, the sample is prevented from being diffused by using the attachment 2308.

Furthermore, it is possible to perform the mass spectrometry to the sample in the channel 2205, in a state in which the frozen or dried sample is kept on the substrate 2301.

In the substrate of this embodiment, a matrix solution is added to the frozen or dried sample in the channel. The matrix is appropriately selected, and sinapic acid is preferable to protein. An adding method is appropriately selected from a spraying method by using an ink-jet, a neblizing method to the chip by using a nebulizer, or the like.

For example, when spraying to the chip by using the nebulizer, if there is a worry that the frozen sample is melt and the frozen sample in the channel 107b is diffused due to a large spraying amount of the matrix solution, the substrate 103 may be cooled in advance. By spraying the matrix solution to the substrate 103, which is kept cool, it becomes possible to prevent the frozen sample from being solved. After that, the sample may be sublimed by the above-described method. Consequently, the matrix may be added while preventing the sample in the channel from being diffused.

At this stage, the channel 107b of the substrate 103, which keeps a mixture of the matrix and the sample, is exposed, and the sample may be analyzed by performing the mass spectrometry to an exposing portion by using the method described in the first embodiment.

Thirteenth Embodiment

The freeze-drying method described in the twelfth embodiment may be easily realized by using a dried gas and a device to be described below.

The dried gas means a gas dried at an extremely low temperature, generated by vaporization of the liquid nitrogen, liquid helium, or the like, which are inert gas, and is used by controlling a pressure, a flow rate, and a temperature thereof. The control of the pressure and the flow rate may be generally realized by a regulator attached to a liquid nitrogen tank and a liquid helium tank. Since the dried gas just flown from the tank keeps a low temperature approximately the boiling point of the original liquid gas, this may be applied to freeze small amount of liquid developed on the chip, and to make the seal covering the chip easily stripped by making a temperature not higher than an applicable temperature thereof. Further, the dried gas may make an extremely dried state in which a partial water vapor pressure is low, and it is possible to dry the small amount of liquid on the chip in a short time by exposing the same to the dried gas. Further, by gradually approximating the temperature of the dried gas to the room temperature, it is possible to take the chip out by keeping a dry state thereof in a room temperature condition.

A freeze-drying device of the chip utilizing the below described dried gas is used to fix the small amount of liquid sample developed on the chip by using the dried gas, by freezing and drying the same.

Figure 42:
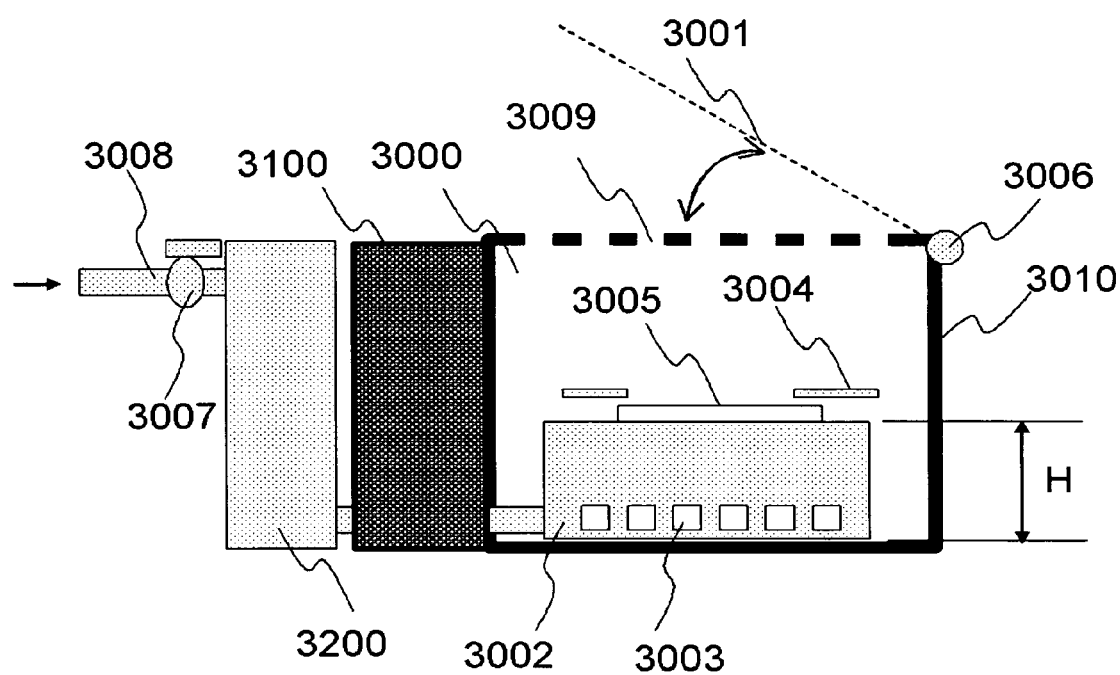
FIG. 42 is a view showing a freeze-drying device of a chip according to an embodiment.
Figure 43:
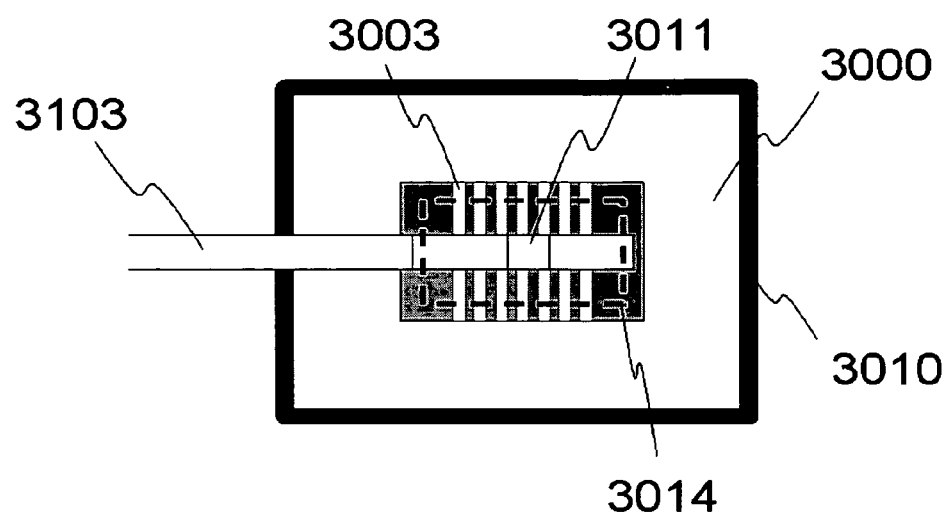
FIG. 43 is a view showing a structure of a drying chamber and a chip stage of the freeze-drying device shown in FIG. 42.
Figure 43:
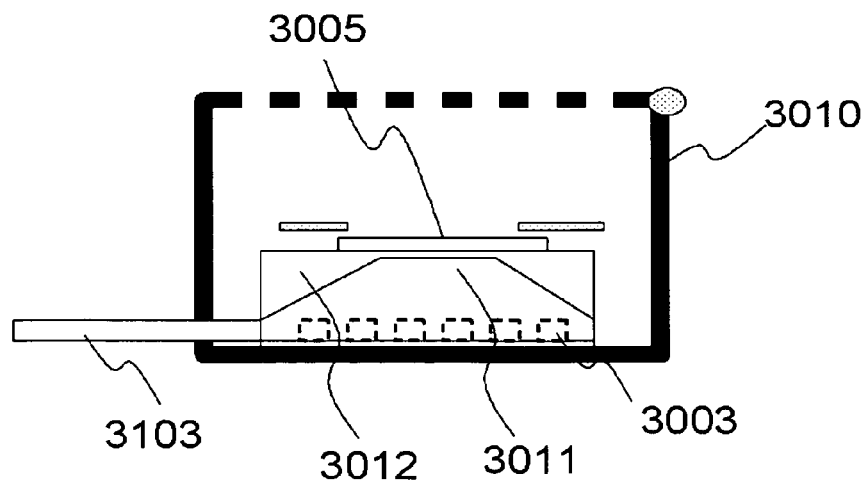
Figure 44:
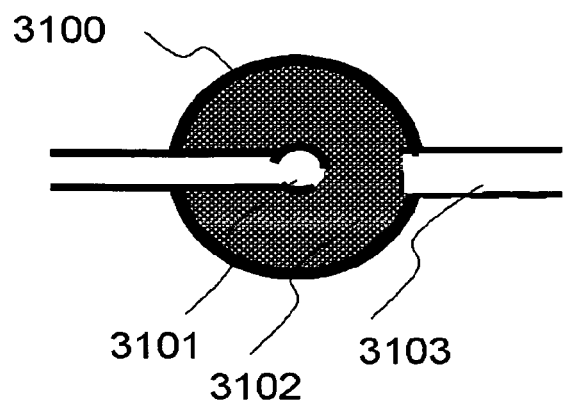
FIG. 44 is a view showing a structure of a dry filter of the freeze-drying device shown in FIG. 42.
Figure 44:
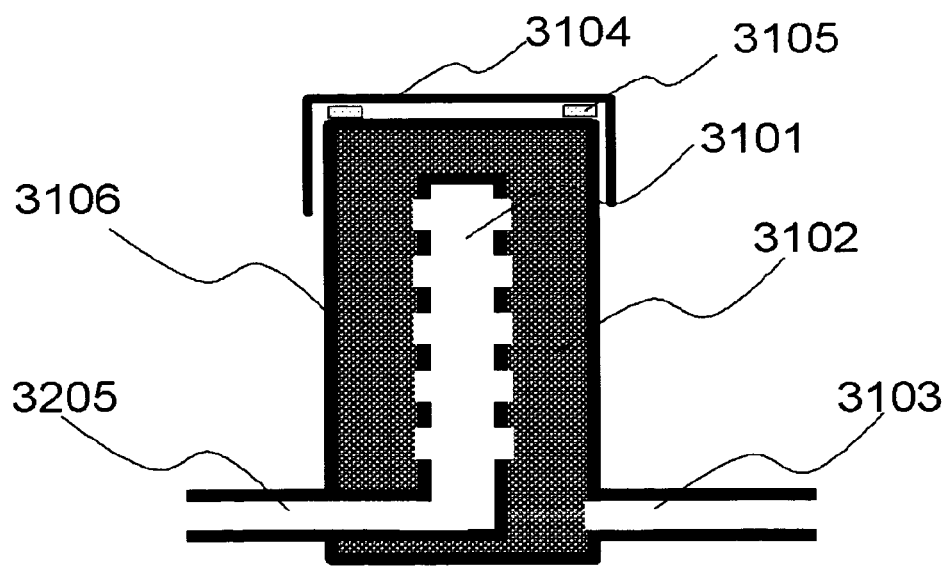
Figure 45:
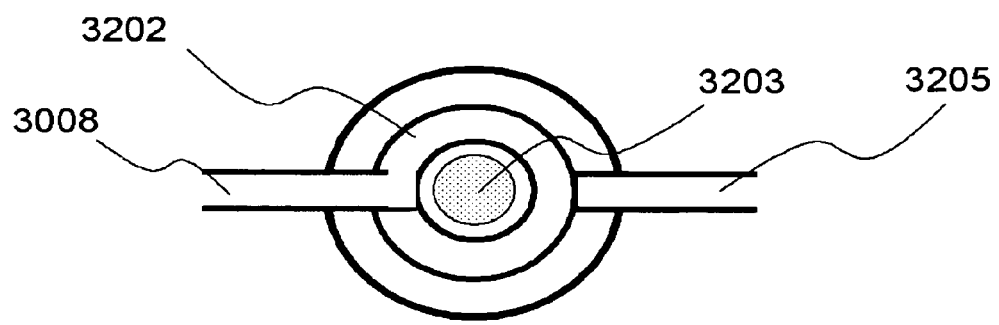
FIG. 45 is a view showing a structure of a heater unit of the freeze-drying device shown in FIG. 42.
Figure 45:
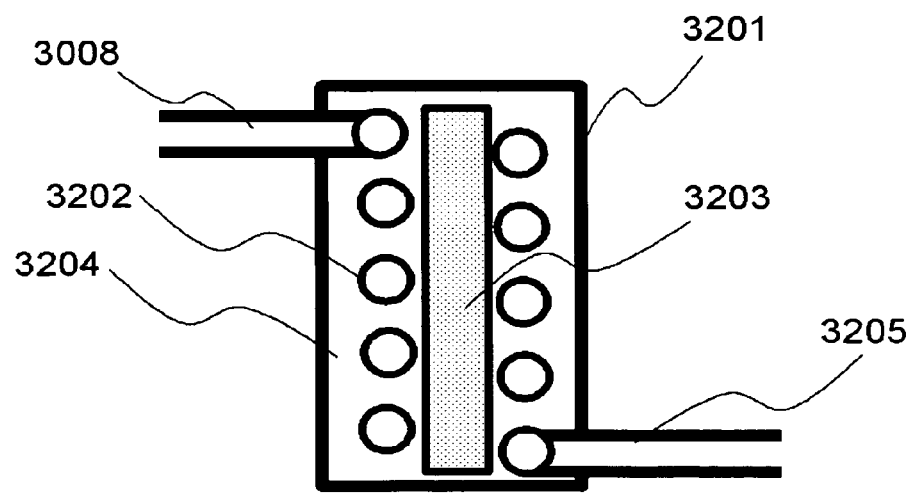

FIG. 42 is an elevation view showing an example of the freeze-drying device of the chip using the dried gas. FIGS. 43(*a*) and 43(*b*) are a plain view and an elevation view each showing a structure of a drying chamber 3000 and a chip stage 3002 of the freeze-drying device shown in FIG. 42, respectively. FIGS. 44(*a*) and 44(*b*) are a plain view and an elevation view showing a structure of a dry filter 3100 of the freeze-drying device shown in FIG. 42, respectively. FIGS. 45(*a*) and 45(*b*) are a plain view and an elevation view showing a structure of a heater unit 3200 of the freeze-drying device shown in FIG. 42, respectively.

Hereinafter, a structure of the freeze-drying device of the chip, utilizing the dried gas will be described with reference to FIGS. 42 to 45.

The freeze-drying device of the chip utilizing the dried gas shown in FIG. 42 is provided with a conduit tube 3008, a cock 3007 provided on the conduit tube 3008, a heater unit 3200 connected to the conduit tube 3008, a dry filter 3100 connected to the heater unit, a chip chamber 3010 connected to the dry filter, and a chip stage 3002 provided in the chip chamber 3010.

An end of the conduit tube 3008 is connected to a tank (not shown), which supplies the dried gas through the cock 3007. A temperature of the dried gas flown through the conduit tube 3008 is controlled when the dried gas passes through the heater unit 3200, and water vapor component of the dried gas is absorbed when the gas passes through the dry filter 3100 to be a further dried state, and after that, the dried gas is introduced into the chip stage 3002 placed in the chip chamber 3010.

The dried gas introduced into the chip stage 3002 is discharged from a plurality of gas outlets 3003 provided on a side surface of the chip stage 3002 to fill the drying chamber 3000, which is a lumen of the chip chamber 3010. And the dried gas is discharged out of the drying chamber 3000 through an air inlet 3009 provided on a cover 3001 which is provided on an upper portion of the chip chamber 3010. The chip 3005 is held on the chip stage 3002 by means of the chip holder 3004, and is freeze-dried by the dried gas filling the drying chamber 3000. A structure of the chip 3005 may be the structure as described in the twelfth embodiment, for example.

The cover 3001 is connected to the chip chamber 3010 by means of the hinge 3006 so as to be opened and closed. The chip 3005 may be set on and taken from the chip stage 3002 from the upper portion of the chip chamber 3010, by opening the cover 3001. An upper end of the chip stage 3002 holding the chip 3005 is raised by a height H from a bottom surface of the chip chamber 3010, such that the chip 3005 is not directly exposed to a jet of the dried gas emitted from the gas outlets 3003. Thereby, the sample developed on the chip 3005 is prevented from being blown by an emission of the dried air. The height H is set to, for example, from 5 cm to 20 cm according to the flow rate and momentum of the dried gas emitted from the gas outlets 3003.

The conduit tube 3008 is formed by a material, strength deterioration of which is small even in a low temperature condition or with an extreme temperature change, for example, a metal such as copper or stainless, and a circumference thereof is covered with a thermal insulating material such as urethane foam, and is connected to a tank (not shown). As the cock 3007, a screw-type valve formed by the same material as the capillary tube or the like is used.

The chip chamber 3010 and the cover 3001 are also obtained by fabricating a material such as metal, deterioration of which is small under a low temperature condition or with a temperature change, in a box-shape. Inner and outer faces thereof are covered with the thermal insulating material with an appropriate thickness (from few millimeters to few centimeters), except the air inlet 3009 portion and the hinge 3006 portion.

A material having resistance to a low temperature condition and with an extreme temperature change and having a high thermal conductivity, for example, metal such as copper, nickel, brass, iron and stainless, is used as the material of the chip stage 3002. An upper end surface of the chip stage 3002 on which the chip 3005 is placed may be applied a coating of a thin Teflon (registered trademark) resin in order to prevent the chip 3005 from adhering to the chip stage 3002. The chip holder 3004 may be realized such that an end of a plate spring formed by an elastic material such as steel or stainless is joined on the surface of the chip stage 3002 by a hinge or by welding, and the other end is kept in a release state so as to nip the chip.

Next, structures of the drying chamber and the chip stage of the freeze-drying device shown in FIG. 42 will be described in more detail with reference to FIGS. 43(*a*) and 43(*b*). As shown in FIGS. 43(*a*) and 43(*b*), a void space 3011 communicating with a conduit tube 3013 is provided within the chip stage 3002, and a portion of the void space 3011 communicates with the plurality of gas outlets 3003. The void space 3011 and the portion of the void space 3011, which communicates with the gas outlets 3003 may be realized by cutting the material of the chip stage 3002 from a bottom surface thereof by using a milling cutter or the like, and then sealing the bottom surface with a plate formed by the same material by welding or by means of the hinge. The chip 3005 is placed on a placing region 3014, and is fixed on the chip stage 3002 with a portion thereof is nipped by the chip holder 3004.

A thickness 3012 from an upper surface of the void space 3011 to a surface of the chip stage 3002 is inhomogeneously selected so as to make a portion desired to lower the temperature at first thin, to make a portion desired to lower the temperature at last thick. A time in which the low temperature of the dried gas flowing into the void space 3011 transmits to the upper surface of the chip stage 3002 is shorter as the thickness 3012 from the void space 3011 to the surface is thinner, and the chip stage 3002 is cooled in order of thin to thick, so that a desired portion on the chip 3005 may be first frozen by selecting the thickness thereof.

Next, a structure of a dry filter of the freeze-drying device shown in FIG. 42 will be described in more detail with reference to FIGS. 44(*a*) and 44(*b*). As shown in FIGS. 44(*a*) and 44(*b*), the dry filter 3100 is composed of an air-pipe 3101 with a hole communicating with a conduit tube 3205 of a heater unit 3200, a desiccant agent 3102 filled around the same, an outer casing 3106 to hold the desiccant agent, an outer casing lid 3104 to seal an inside of the outer casing 3106, a packing 3105 to increase shelter density, and a conduit tube 3103 welded so as to communicate with inside of the chip stage 3002 and the outer casing 3106.

An inner surface of the outer casing lid 3104 and a portion of the casing 3106 abutting the inner surface of the outer casing lid 3104 are threaded, and the desiccant agent 3102 may be changed by releasing the inside of the outer casing 3106 by rotating the outer casing lid 3104. And the inside of the outer casing 3106 can be sealed by fastening the outer casing lid 3104 with the packing 3105 interposed therebetween.

A dust and water vapor of the dried gas flown into the air-pipe 3101 are removed while the dried gas flows through a clearance in the desiccant agent 3102, and the dried gas, which is in a drier state, is introduced into the chip stage 3002 through the conduit tube 3103.

The outer casing 3106, the air-pipe 3101, the conduit tube 3103, and the outer casing lid 3104 also are made of a material, which is tolerant of the low temperature condition and the extreme temperature change and pressure, and is resistant to chemicals, such as copper, nickel, brass and stainless. The inner surface thereof may be coated with Teflon (registered trademark) or the like so as to improve an anticorrosion property. The packing 3105 may be formed by an O-ring, obtained by forming metal having high-flexibility such as copper and aluminum in a plate-ring shape. The desiccant agent 3102 may be made of a soda lime or a highly hygroscopic agent, such as calcium chloride, silica gel or the like, formed in a granular shape.

Next, a structure of the heater unit of the freeze-drying device shown in FIG. 42 will be described in more detail, with reference to FIGS. 45(*a*) and 45(*b*). As shown in FIGS. 45(*a*) and 45(*b*), the heater unit 3200 is made of a protective casing 3201, a spiral tube 3202, a heater 3203, a thermal insulating material 3204, and a conduit tube 3205.

The spiral tube 3202 communicates with a conduit 3008, and twists around the heater 3203 in a spiral manner. An outlet of the spiral tube 3202 communicates with the capillary tube 3205. As the heater 3202, an electrical heater and an oil heater may be used, and a surface thereof is protected by a highly thermal conductive metal such as copper. The spiral tube 3202 is resistant to the low temperature condition and the temperature change. Since the spiral tube 3202 is made of highly thermal conductive metal, such as copper, brass, nickel, and stainless, and is heated by the heater 3203, and the dried gas is heated while flowing through the spiral tube 3202 up to a desired temperature.

As the thermal insulating material 3204, the material having resistance to low temperature, high temperature and with temperature change, which hardly expands or contracts, for example, diatom earth, is preferably used. The protective casing 3201 is made of a material resistant to low temperature, and high temperature and with temperature change, for example, metal such as copper, nickel, iron, and stainless, and, an outer wall thereof is covered with the thermal insulating material such as flame resistance urethane foam.

In order to improve a temperature controlling accuracy, the temperature may be monitored by providing a thermistor-thermometer within the spiral tube 3202 or the conduit tube 3205. And further, it can be improved so as to automatically control to a preset temperature by giving a negative feedback a temperature measurement result to an output of the heater 3203.

Next, a process of freeze-drying the sample developed on the chip by using the freeze-drying device utilizing the dried gas will be described.

First, the cover 3001 is opened, and the chip 3005 on which the sample is developed is nipped by the chip holder 3004 and is fixed on the chip stage 3002. Next, after the cover 3001 is closed, the cock 3007 is released and the drying chamber 3000 is filled with the dried gas through the chip stage 3002. At this time, the heater 3202 is not heated. At this time, since a thinner portion of the chip stage 3002 is first cooled, it is possible to freeze the chip from a desired portion thereof. In parallel with the freezing, the adhesion of the resin layer 102 (seal lid) of the lid 113 covering the chip is lowered and the resin layer 102 is stripped, so that the cover 3001 is opened in a short time to remove the lid 113 (seal).

If the low-temperature dried gas is further continuously infused, moisture in the sample is evaporated in the dried gas, and the sample is dried and becomes solidified. Time elapsed for the drying and solidification varies according to a size of the channel of the chip, so that an appropriate freeze-drying time is experimentally determined in advance.

At the last, the heater 3203 is heated to gradually increase the temperature of the dried gas flowing through the spiral tube 3202, finally up to a room temperature (around 25° C.).

By maintaining this state in a predetermined time, the temperature of the drying chamber 3000, the chip stage 3002, and the chip is returned to approximately the room temperature, then at this stage, the cover 3001 is opened, and the chip on which the sample is dried and become solidified, is taken out.

By doing so, the sample separated in the chip is easily freeze-dried by using the dried gas and a following device.

Although the embodiments of the present invention has been described above, the present invention is not limited to these, and the structures used in each of the embodiments may be optionally combined.

For example, the present invention may be structured as follows.
(1) The chip introducing a fluid into the channel.
(2) The chip introducing the solution into the channel.
(3) The chip introducing the solution including protein into the channel.
(4) The chip according to (3), making protein perform the electrophoresis.
(5) The chip according to (3), separating protein.
(6) The chip according to (2), separating by the electrophoresis.
(7) The chip according to (2), separating by the isoelectric focusing electrophoresis.
(8) The chip according to (2), separating by affinity.
(9) A method of using the chip according to (3), having a freeze-drying process.
(10) The electrophoresis system, including the freezing mechanism.
(11) The electrophoresis system, including the freeze-drying mechanism.
(12) The electrophoresis system, including a chip conveying mechanism.
(13) The electrophoresis system, including a drying mechanism.
(14) The electrophoresis system, including a vacuuming mechanism.
(15) The chip according to (3), going through a freeze state.
(16) The chip according to (2), analyzing by the mass spectrometry device.

The present invention may independently include each of the above-described structures (1) through (16), or may simultaneously include two or more structures.

And, the present invention may include following structures.
(17) A channel structure, including a convex structure or a wall surface having minute irregularity on the surface thereof.
(18) The channel structure, including the convex structure or the wall surface, each having a hydrophilic surface.
(19) The channel structure including the convex structure having a portion, a diameter of which is smaller than that of a top portion.
(20) An angle of the wall surface and the bottom surface of the convex portion, and an angle of the wall surface and the bottom surface of the channel are not larger than 90°.
(21) The channel structure, including the convex structure or the wall surface of the inverted mesa structure or the concave.
(22) A lateral groove structure formed on the surface of the substrate other than the channel. The lateral groove structure runs from an end to the other end of the substrate.
(23) A seal chip, wherein a seal has a lid made of silicone resin, the seal chip having a temperature range from −20° C. to 30° C. within an operating temperature range in which the deterioration of adhesion is within 20% of the maximum value of the adhesion in the temperature range not lower than −20° C. and not higher than 30° C.
(24) The seal chip, wherein the seal has a lid made of acrylic resin, the seal chip having the temperature range from −20° C. to 30° C. within the operating temperature range in which the deterioration of the adhesion is within 20% of the maximum value of the adhesion in the temperature range not lower than −20° C. and not higher than 30° C.
(25) The chip, holding the frozen solution in the channel.

The present invention may independently include each of the above-described structures (17) through (25), or may simultaneously include two or more structures.

And, the present invention may have structures as follows.
(26) A chip cooling stage, including a mechanism for making a temperature gradient such that the reservoir is frozen later than the channel.
(27) The chip cooling stage, including portions having different thermal conductivity, for making the temperature gradient such that the reservoir is frozen later than the channel.
(28) The bottom surface of the chip, specifically, the bottom surface other than the reservoir is metal evaporated.
(29) A meander channel structure.

The chip cooling stage having a temperature distribution, using materials having different thermal conductivity.
(31) The chip cooling stage, having a vertical interval on the surface thereof, and a contact portion with the chip is limited to a portion other than the reservoir.
(32) The chip cooling stage, having a shape in which the reservoir portion of the chip is removed. (32) An attachment to vacuum freeze-dry, including the gas-introducing path, using a material having a large heat capacity.

The present invention may independently include each of the above-described structures (26) through (33), or may simultaneously include two or more structures.

Example 1

In this embodiment, the chip 112 and the fixing device 111 as described in the first embodiment (FIGS. 5 and 6) were fabricated. The substrate 103 was formed by a silicon substrate. The plate-like lid 101 was made of the glass plate, and the resin layer 102 was made of polyolefin. The retainer plate 104 and the board 108 were made of SUS and aluminum, respectively. An outer dimension of the surface of the substrate 103 is appropriately selected as usage, and in this example, it was set 20 cm by 70 mm.

On the substrate 103, as shown in FIG. 3, the channel 107*b* was formed, and the channel 107*a*, which may be the channel for inputting, was formed so as to intersect with the channel 107*b*. The reservoirs 105*a* and 105*b*, and the reservoirs 105*c* and 105*d* were formed on both ends of the channels 107*a* and 107*b*, respectively. The channels 107*a* and 107*b* were formed by dry etching. Each of the channels was set 0.4 µm to 2 µm in depth, and 40 µm to 100 µm in width.

Next, the resin layer 102 was placed on the substrate 103 by adjusting positions of the reservoirs 105*a* to 105*d* to positions of the holes 115*a* to 115*d*, respectively. In this state, a glass tube 110 with an inner diameter of 1.8 mm, an outer diameter of 3.0 mm, and a height of 3.0 mm was bonded on each reservoir position of the resin layer 102 by epoxy resin. Next, the plate-like lid 101 was placed in a similar way by adjusting the positions of holes corresponding to each of the reservoirs. After that, the substrate 103, the resin layer 102, and the plate-like lid 101, which were layered, were placed on the board 108 of the fixing device 111. Then, a pressure was applied by the retainer plate 104 fastened by the screw 106.

The pressure applied by the fixing device 111 was set to 10 to 20N/cm². Further, the electrode is provided on each of the reservoirs. By using this, it becomes possible to apply an electrical field on both ends of the channels 107a and 107b.

As the migration buffer, 1M tris-borate-EDTA buffer of pH7 was introduced into the reservoirs 105a, 105b, 105c and 105d, and it was confirmed that there was no leakage from the channel structure. It was proven that the migration buffer was prevented from leaking by pressure welding the lid 113 including the plate-like lid 101 and the resin layer 102 to the substrate 103 by a pressure device.

Further, a DNA solution was introduced into the reservoir 105b as a sample, and the voltage of 100V was applied to the electrode provided in the reservoirs 105b. As a result, it was proven that the chip 112 is resistant to the high voltage and the DNA may perform the electrophoresis in the channel 107b by a following method. A method of performing the electrophoresis of the components of the sample by using the device of this embodiment will be described with reference to FIG. 5. First, the DNA solution was infused to the reservoir 105a as the sample. Next, the voltage of 100V was applied such that the sample flows in a direction toward the reservoir 105b. Thereby, the sample flows into the channel 107a, and accordingly fills the entire channel 107a. At this time, on the channel 107b, the sample exists only on an intersecting point with the same and the channel 107a.

Next, the application of the voltage between the reservoirs 105a and 105b was stopped, and the voltage of 100V was applied between the reservoirs 105c and 105d for five minutes such that the sample flows in a direction toward the reservoir 105d. Thereby, the sample passed through the channel 107b.

Meanwhile, in the chip of this example, the components of the sample are optically detected in the detecting unit 109. The optical detection may be performed, for example, by combining the molecule with a fluorescent material in advance, irradiating the same at the detecting unit 109 with a laser, and observing the fluorescence emitted from the molecule.

Next, by freezing the sample by leaving the same for one hour at a temperature of −20° C., the sample in the channels 107a and 107b was prevented from leaking when removing the lid 113. After that, the retainer plate 104 was taken off by loosing the screw 106 of the fixing device 111, and the plate-like lid 101 was taken away from the substrate 103. Then, the resin layer 102 was removed in a state in which the substrate 103 was fixed. Consequently, the channels 107a and 107b were opened, and it was confirmed that the sample was held in the channel structure.

In this example, the channels 107a and 107b were opened by removing the lid 113. The sample in the channels was not leaked. At this stage, on the substrate 103, the channel 107b holding the sample was exposed, and by performing the mass spectrometry to this portion by using the method described in the first embodiment, the DNA was analyzed.

Example 2

In this example, the substrate 103 was fabricated by using the same method as in the example 1. Materials of the plate-like lid 101, the retainer plate 104, the screw 106, the stage 108, and the tube 110 also were identical to those of the example 1. But, the resin layer 102 was made of polyolefin, to which an acrylic adhesive is applied. When placing the resin layer 102 on the substrate 103, this was placed such that the surface with adhesive faces to the substrate 103 side, and the glass tube 110 was bonded by epoxy resin in similar way.

The electrophoresis was performed with the DNA in a similar way as in the example 1, by using the obtained device. Next, by freezing the sample by leaving the same at a temperature of −20° C. for one hour, the sample in the channel was prevented from leaking when removing the lid 113. After that, the retainer plate 104 was taken off by loosing the screw 106 of the pressure device, and the plate-like lid 101 was taken away from the upper portion of the substrate 103. Then, the resin layer 102 was removed in a state in which the substrate 103 was fixed. Consequently, the channels 107a and 107b were opened, and it was confirmed that the sample was held in the channel.

As described above, by the device of this example, leakage of the sample from the channel structure was prevented, and the channels 107a and 107b were opened by removing the lid 113. At this stage, the channel 107b holding the sample of the substrate 103 was exposed, and by performing mass spectrometry to this portion in the same way as in the example 1, the DNA was analyzed.

Example 3

In this embodiment, in the chip 112 (FIG. 41) described in the twelfth embodiment, the chip having only a straight channel of the channel 107b out of the channel shape shown in FIG. 3 was fabricated. The substrate 103 was formed by a quartz glass substrate. The plate-like lid 101 was made of polyolefin, and the resin layer 102 was formed by the silicone resin. The lid 113 is a sheet obtained by joining the plate-like lid 101 and the resin layer 102. The outside dimension of the surface of the substrate 103 is appropriately selected as usage, and in this example, it was set 20 cm by 70 mm.

On the substrate 103, the straight channel 107b, shown in FIG. 3 was formed as the channel for separating, and the reservoirs 105c and 105d were formed on both ends thereof. The channel 107b was formed by dry etching. A depth, a width, and a length of the channel were set 10 μm, 100 μm, and 60 mm, respectively. The convex structure with a pitch of 10 μm and a diameter of 4 μm was formed on the channel 107b. By this convex structure, the lid 113 was prevented from bending, and it was confirmed that the frozen solution was held in the channel.

Next, the lid 113 was placed on the substrate 103 by adjusting the positions of the reservoirs 105c and 105d to the positions of the holes 115c and 115d. In this state, the glass tube 110 having the inner diameter of 1.8 mm, the outer diameter of 3.0 mm, and the height of 3.0 mm was bonded to each of the reservoir positions of the lid 113 by epoxy resin. Further, the electrode was provided in each of the reservoirs. By using the electrodes, electrical field may be applied to both ends of the channel 107b.

By using thus obtained chip, protein was separated by isoelectric focusing electrophoresis. The protein is ampholyte and has a proper isoelectric point (pI). Consequently, the sample such as protein is separated by migrating to a position at which the pH corresponds to each of the isoelectric points on the pH gradient, and simultaneously concentrated.

The channel was filled with the sample by introducing a carrier ampholytes solution including protein as a liquid to be used for migration, that is, as the sample, into the reservoir 105c, and vacuuming the channel through the reservoir 105d. After that, it was confirmed that there is no leakage from the channel structure. Two kinds of Myoglobin (1 μg/μl, pI 7.2) and β-LactoglbulinA (1 μg/μl, pI 5.1) were used as protein. These proteins were stained in advance by using fluorescent dye Cy3.

Next, 0.02M of sodium hydroxide solution and 0.1M of phosphoric acid solution were introduced into the reservoirs 105c and 105d, respectively, the electrodes were set to each of the reservoirs, and a voltage of 1.8 kV was applied between the electrodes. Consequently, it was confirmed that the chip 112 could be used without leakage of the sample even when the high-voltage was applied to the same.

The protein migrates in the channel 107b to concentrate on a position at which the pH corresponds to each isoelectric point on the pH gradient. As a result, the protein was separated according to each isoelectric point pI, and was concentrated in a band-shape.

In the chip of this embodiment, the detecting unit 109 extends to an entire channel 107b. The separated protein is optically detected at the detecting unit 109. The optical detection may be performed, for example, by combining the molecule with the fluorescent material in advance, irradiating the same at the detecting unit 109 with a laser, and observing the fluorescence emitted from the molecule.

In this example, the X-Y automatic stage was used as the stage of the fluorescence microscope, on which the measurement was performed, by using the fluorescent measurement system in which the X-Y automatic stage, the fluorescence microscope, and the photo multiplier are combined. The chip was placed on the stage of the X-Y automatic stage, and the detecting unit is irradiated with an exciting light through the optical system of the fluorescence microscope. When performing the fluorescent measurement of the detecting unit, a photon counting is performed by the photo multiplier through the optical system of the fluorescence microscope.

Figure 46:
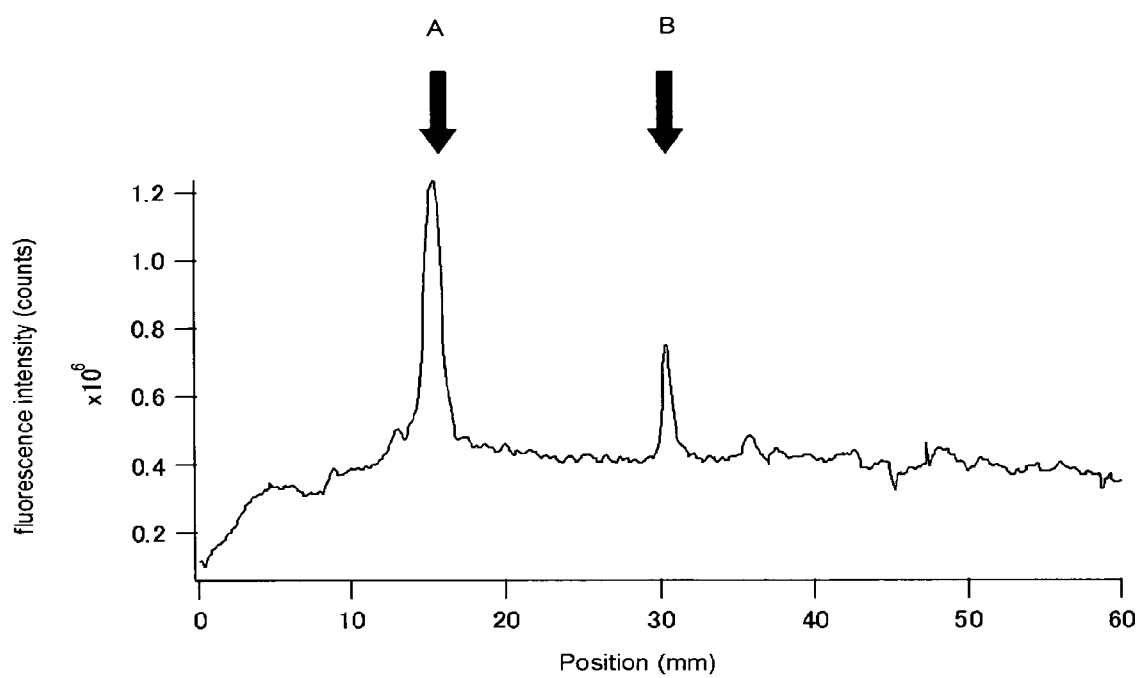
FIG. 46 is a graph showing a result of performing a photon counting of protein after an isoelectric separation according to an example.

FIG. 46 shows a result of performing the photon counting after separating the proteins. The horizontal axis represents a transferring distance of the stage along the channel, in which the right side is acid pI and the left side is alkaline pI. The vertical axis represents the number of photon counts. A portion on which the fluorescently stained protein is concentrated is large in the number of the photon counts, and is observed as a peak. In FIG. 46, arrows A and B indicate the peaks of Myoglobin and β-LactoglobulinA, respectively. From FIG. 46, it has been found that the proteins could be separated according to their isoelectric points pI, by using the chip of this example.

Next, the chip 112 was cooled quickly in order to prevent the separated and concentrated protein from diffusing. The cooling temperature is appropriately selected according to the kind of the sample and the lid 113, and as usage. In this example, the block stage of aluminum was cooled down to −150° C. by using liquid nitrogen, and the chip was placed on the block stage as the cooling stage, thereby cooling the same quickly. At this time, the sample in the channel first became solidified, and next, the adhesive layer of the sheet was hardened. By freezing the sample, the lid 113 was removed without leakage of the sample in the channel 107b.

After that, the resin layer 102, which became easy to be detached by being hardened, was removed from the substrate 103 without adhesive deposit. At this time, it was confirmed that the frozen sample was held in the channel without attaching to the resin layer 102, if the convex structure was formed in the channel with a pitch of 10 μm and a diameter of 4 μm. As a result, the channel 107b was opened and the frozen sample was held in the channel structure.

Next step is to perform the mass spectrometry to the chip holding the separated protein. However, the frozen chip is very difficult to handle. If the frozen sample is taken away from the cooling stage, this melts easily with an increase of a temperature and the separated protein is diffused. Therefore, in this example, the protein in the channel 107b was freeze-dried by using the attachment 2308 cooled down to a temperature of −80° C. in advance by the method described in the twelfth embodiment.

As a result of freeze-drying by using the attachment 2308, it was confirmed that, on the substrate 103, the components of the sample were separated out in the channel 107b, and the separated sample was held in a drying state.

Figure 47:
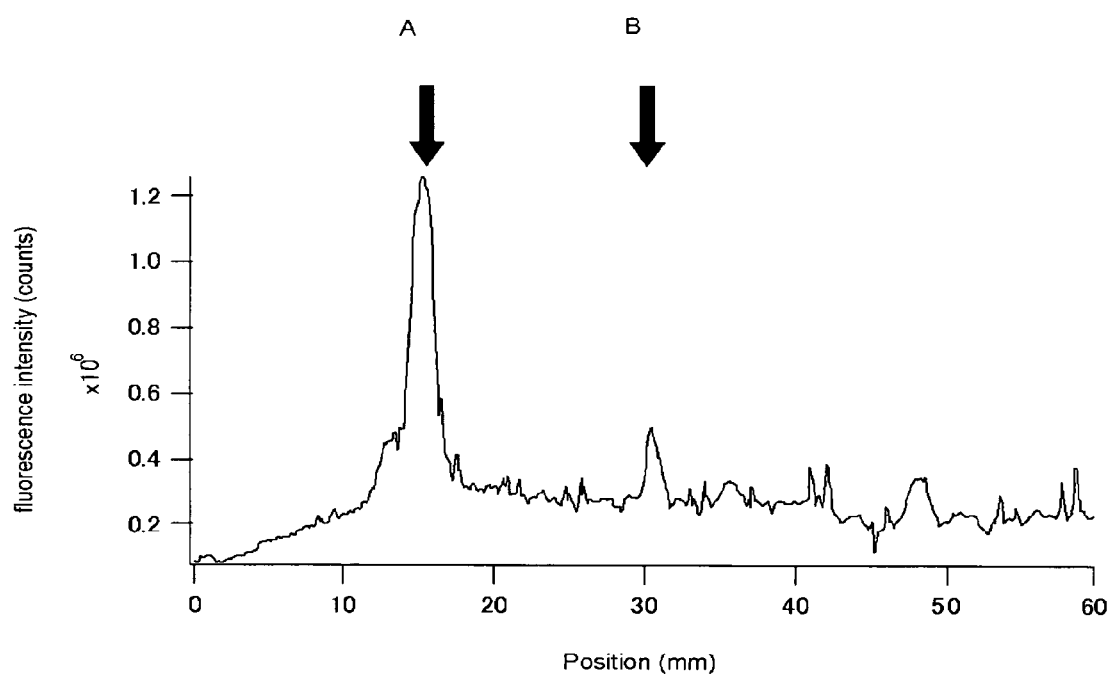
FIG. 47 is a graph showing a result of performing a photon counting of protein after an isoelectric separation and freeze-drying according to an example.

FIG. 47 is a graph showing a result in which the protein is freeze-dried after separating the same according to the isoelectric points and is the photon counting performed on the protein. The arrows A and B indicate peaks of Myoglobin and β-LactoglobulinA, respectively. The peaks A and B in FIGS. 46 and 47 correspond to each other. From FIG. 47, it was confirmed that the protein was held in the channel 107b while keeping the peaks of the separated protein, separated.

Next, a matrix solution (sinapic acid 10 mg/ml) was added to the protein in the dry state in the channel 107b. Method of adding the same was a nebulizing method using the nebulizer. After that, the matrix solution on the substrate 103 was naturally dried.

At this stage, on the substrate 103, the channel 107b holding the mixture of the matrix and the protein was exposed, and by performing the mass spectrometry by using the method described in the first embodiment, the protein was analyzed. The mass spectrometry was performed to the channel 107b portion corresponding to the portions indicated by the arrow A and B in FIG. 47. From the mass spectrometry result of the portions indicated by the arrow A and B, Myoglobin and β-LactoglobulinA were restored.

In this example, the channel 107b could be opened by removing the lid 113. The sample in the channel did not leak, and the contamination was not generated. And next, the freeze-drying was performed by using the attachment 2308, thereby subliming the solvent component while keeping the peaks of the separated proteins, separated. At this stage, on the substrate 103, the channel 107b holding the proteins was exposed, and by adding the matrix solution to the portion and performing the mass spectrometry described in the first embodiment, the protein was analyzed.

The invention claimed is:

1. A chip, wherein a groove-like minute space formed on a surface of a substrate is a channel, the chip having a removable lid covering the minute space,
wherein said lid is composed of a heat-shrinkable member, and a portion to be fractured easier than other portion of said lid is formed along said channel.

2. The chip according to claim 1, further comprising a through hole provided in the lid, the through hole extending from an upper surface of the lid to the groove-like minute space and communicating with the groove-like minute space.

3. The chip according to claim 1, wherein said lid is a plate-like member.

4. The chip according to claim 2, wherein a portion of the surface of said lid contacting with said substrate or an entire surface of said lid is hydrophobic or water-repellent.

5. The chip according to claim 2, wherein at least one of a wall surface of a groove forming said channel and a surface of said lid is hydrophobic or water-repellent.

6. The chip according to claim 1, wherein an elastic member having viscoelasticy to adhere to said substrate is disposed on at least a portion of said lid.

7. The chip according to claim 2, wherein said lid has a sucker portion which adsorbs to the surface of said substrate, and
a detach tab, which aids detachment of said lid.

8. The chip according to claim 2, wherein said lid has
a strip portion provided only in the vicinity of said channel, and
said strip portion includes a detach tab, which aids detachment of said lid.

9. The chip according to claim 8, wherein said strip portion includes
a film for removing comprised of a material different from a material of other portion of said lid, wherein said film for removing is provided only a range in the vicinity of said channel to be detached from.

10. The chip according to claim 1, wherein said substrate or said lid is formed by a silicone resin including polydimethylsiloxane.

11. A chip, comprising:
a substrate;
a groove formed on said substrate as a channel;
a lid covering an opening portion of said groove, which lid includes a heat-shrinkable member and a portion to be fractured easier than other portion of the lid is formed along the channel; and
a through hole provided on said lid and communicating with said groove,
wherein said lid includes an elastic member, and
a surface of said lid contacting with said substrate is formed so as to project from a peripheral portion to a center portion of said lid.

12. The chip according to claim 11, wherein said substrate or said lid is formed by an acrylic resin.

13. The chip according to claim 11, wherein said groove forms a gas-introducing groove, at least a portion of which is exposed to an outer air is provided, wherein said gas-introducing groove is formed on a surface of said substrate contacting with said lid or on a surface of said lid contacting with said substrate so as not to contact with said channel.

14. The chip according to claim 11, wherein:
a convex structure smaller than a width of said channel is provided on at least a portion having said lid in said channel, and
a surface of said convex structure has an irregularity.

15. The chip according to claim 14, wherein:
one or more of said convex structures are formed at intervals of not greater than 80 μm in a width direction of said channel,
one or more of said convex structures are formed at intervals of not greater than 80 μm in a longitudinal direction of said channel, and
an upper surface of said convex structure contacts with said lid.

16. The chip according to claim 14, wherein a distance between centers of said convex structures is not greater than 20 μm.

17. The chip according to claim 14, wherein a sum of a projecting area in an entire circumference of said convex structure to a surface perpendicular to an upper surface of said channel is not smaller than a half of a surface area of said lid contacting with contents of said channel.

18. The chip according to claim 14, wherein an area of an upper surface of said convex structure is greater than 0.06% of an area of an upper surface of said channel.

19. The chip according to claim 14, wherein an area of an upper surface of said convex structure is greater than an area of a bottom surface of said convex structure.

20. The chip according to claim 11, wherein at least a portion of said lid contacting with said substrate is a porous layer, which includes a liquid from said channel and the lid further includes a lyophobic member.

21. The chip according to claim 11, wherein at least a portion of the surface of said lid contacting with said substrate is a porous layer, and a void of said porous layer communicates with both surfaces of said lid.

22. The chip according to claim 11, wherein said substrate is formed by a porous material.

23. A chip, wherein a groove-like minute space formed on a surface of a substrate is a channel, the chip having a removable lid covering the minute space, said lid including: a partition wall structured so as to cover said channel, and
a liquid, which fills a space formed between a solution in said channel and said partition wall.

24. The chip according to claim 23, wherein a gravity of said liquid is smaller than a gravity of said solution in said channel.

25. The chip according to claim 23, wherein a coagulation point of said liquid is lower than a coagulation point of said solution in said channel.

26. A device, comprising
at least the chip according to claim 2; and
a sample fixing mechanism, which fixes contents of said channel in said channel.

27. The device according to claim 26, further comprising:
an opening mechanism, which opens a region including the contents of said channel sealed with said lid.

28. The device according to claim 27, further comprising:
a solvent drying mechanism which dries a solvent.

29. The device according to claim 26, wherein said sample fixing mechanism fixes the contents by causing a loss of fluidity of the contents of said channel.

30. The device according to claim 28, wherein said solvent drying mechanism is composed of a sealed vessel and a mechanism which depressurizes an inside of said sealed vessel to a pressure at which the solvent may be sublimed.

31. The device according to claim 28, wherein said solvent drying mechanism comprises heating means for heating said chip up to a temperature at which the solvent is evaporated.

32. A device comprising:
a chip, wherein a groove-like minute space formed on a surface of a substrate is a channel, the chip having a removable lid covering the minute space, which lid includes a heat-shrinkable member and a portion to be fractured easier than other portion of the lid is formed along the channel; and
a sample fixing mechanism, which fixes contents of the channel in the channel by causing a loss of fluidity of the contents of the channel,
wherein said sample fixing mechanism comprises a cooling mechanism which freezes a solution in said channel.

33. A method of using a device, which comprises a chip including a channel comprised of a groove-like minute space formed on a surface of a substrate, a removable lid which covers the minute space, and a through hole provided in the lid, the through hole extending from an upper surface of the lid to the groove-like minute space and communicating with the groove-like minute space, wherein the lid includes a heat-shrinkable member, and a portion to be fractured easier than other portion of the lid is formed along the channel, the method comprising:
fixing contents of the channel in the channel; and
opening a region including the contents of the channel sealed with the removable lid after fixing the contents of said channel.

34. The method of using the device according to claim 33, further comprising:
drying the contents of said channel naturally after opening the region of said channel.

35. A method of using a device which comprises a chip, wherein a groove-like minute space formed on a surface of a substrate is a channel, the chip having a removable lid covering the minute space, the method comprising:

fixing contents of the channel in the channel by freezing the contents of said channel; and opening a region including the contents of the channel sealed with the lid after fixing the contents of the channel.

36. A method of using a device which comprises a chip, wherein a groove-like minute space formed on a surface of a substrate is a channel, the chip having a removable lid covering the minute space, the method comprising:

fixing contents of the channel in the channel;

opening a region including the contents of the channel sealed with the lid after fixing the contents of the channel; and freeze-drying the contents of said channel after opening the region of said channel.

37. A method of using the chip of claim 20, the method comprising:

fixing contents of said channel by transcribing the contents to the porous layer.

* * * * *

UNITED STATES PATENT AND TRADEMARK OFFICE
CERTIFICATE OF CORRECTION

| | | |
|---|---|---|
| PATENT NO. | : 7,785,533 B2 | Page 1 of 1 |
| APPLICATION NO. | : 10/571585 | |
| DATED | : August 31, 2010 | |
| INVENTOR(S) | : Machiko Fujita et al. | |

It is certified that error appears in the above-identified patent and that said Letters Patent is hereby corrected as shown below:

Column 16, Line 25: Delete "101" and insert -- 106 --

Column 23, Line 31: Delete "6011" and insert -- 601, --

Column 47, Line 24: In Claim 11, after "member," delete "and"

Column 47, Line 26: In Claim 11, before "to project" delete "so as"

Signed and Sealed this
Fifteenth Day of March, 2011

David J. Kappos
*Director of the United States Patent and Trademark Office*